US010576125B2

(12) United States Patent
Kopke et al.

(10) Patent No.: US 10,576,125 B2
(45) Date of Patent: Mar. 3, 2020

(54) METHODS FOR ENHANCING SYNAPTOGENESIS AND NEURITOGENESIS

(71) Applicant: HOUGH EAR INSTITUTE, Oklahoma City, OK (US)

(72) Inventors: Richard D. Kopke, Oklahoma City, OK (US); Wei Li, Edmond, OK (US)

(73) Assignee: Hough Ear Institute, Oklahoma City, OK (US)

( * ) Notice: Subject to any disclaimer, the term of this patent is extended or adjusted under 35 U.S.C. 154(b) by 0 days.

(21) Appl. No.: 15/796,522

(22) Filed: Oct. 27, 2017

(65) Prior Publication Data

US 2018/0117115 A1 May 3, 2018

Related U.S. Application Data

(60) Provisional application No. 62/415,101, filed on Oct. 31, 2016, provisional application No. 62/510,596, filed on May 24, 2017, provisional application No. 62/488,740, filed on Apr. 22, 2017, provisional application No. 62/550,345, filed on Aug. 25, 2017.

(51) Int. Cl.
| | |
|---|---|
| A61K 38/10 | (2006.01) |
| C07K 14/475 | (2006.01) |
| A61K 38/07 | (2006.01) |
| A61K 31/185 | (2006.01) |
| A61K 31/198 | (2006.01) |
| A61K 31/41 | (2006.01) |
| A61K 38/06 | (2006.01) |
| A61K 31/221 | (2006.01) |
| A61K 38/08 | (2019.01) |

(52) U.S. Cl.
CPC ............ *A61K 38/10* (2013.01); *A61K 31/185* (2013.01); *A61K 31/198* (2013.01); *A61K 31/221* (2013.01); *A61K 31/41* (2013.01); *A61K 38/063* (2013.01); *A61K 38/07* (2013.01); *C07K 14/475* (2013.01); *A61K 38/085* (2013.01)

(58) Field of Classification Search
CPC ....... A61K 38/10; A61K 31/00; A61K 38/063
See application file for complete search history.

(56) References Cited

U.S. PATENT DOCUMENTS

| | | | |
|---|---|---|---|
| 5,488,145 A | 1/1996 | Carney | |
| 9,289,404 B2 * | 3/2016 | Kopke | ................... A61K 31/15 |
| 10,022,346 B2 * | 7/2018 | Kopke | ................... A61K 31/15 |
| 2002/0115706 A1 | 8/2002 | Ylikoski et al. | |
| 2009/0306225 A1 | 12/2009 | Lichter et al. | |
| 2012/0070407 A1 | 3/2012 | Lazdunski et al. | |
| 2012/0172435 A1 * | 7/2012 | Kopke | ................... A61K 31/15 |
| | | | 514/556 |
| 2014/0187631 A1 * | 7/2014 | Kpoke | ................... A61K 31/15 |
| | | | 514/547 |
| 2015/0209367 A1 | 7/2015 | Edge et al. | |
| 2016/0158173 A1 | 6/2016 | Kopke et al. | |

FOREIGN PATENT DOCUMENTS

| | | |
|---|---|---|
| WO | WO 2014/014828 A1 | 1/2014 |
| WO | WO 2014/195322 A1 | 12/2014 |

OTHER PUBLICATIONS

Kobel (hearing Research, 349, (2017) 148e154; 148-154).*
Ewert, et al., Antioxidant Treatment Reduces Blast-Induced Cochlear Damage and Hearing Loss; *Hearing Research*, vol. 285, pp. 29-39 (2012).
Du, et al., "Effects of Antioxidant Treatment on Blast-Induced Brain Injury," *Plos One*, vol. 8, No. 11, e80138, 17 pages (Nov. 2013).
Lin, et al., "Primary Neural Degeneration in the Guinea Pig Cochlea After Reversible Noise-Induced Threshold Shift," *JARO*, vol. 12, pp. 605-616 (Jun. 2011).
Makary, et al., "Age-Related Primary Cochlear Neuronal Degeneration in Human Temporal Bones," *JARO*, vol. 12, pp. 711-717 (Jul. 2011).
Viana, et al., "Cochlear neuropathy in human presbycusis: confocal analysis of hidden hearing loss in post-mortem tissue," *Hearing Research*, vol. 327, pp. 78-88 (Sep. 2015).
Schaette, et al., "Tinnitus with a Normal Audiogram: Physiological Evidence for Hidden Hearing Loss and Computational Model," *The Journ. Of Neuroscience*, vol. 31, No. 38, pp. 13452-13457 (Sep. 2011).
Wan, et al., "No longer falling on deaf ears: mechanisms of degeneration and regeneration of cochlear ribbon synapses," *Hearing Research*, vol. 329, 24 pages (Nov. 2015).
Liberman, et al., "Toward a Differential Diagnosis of Hidden Hearing Loss in Humans," *Plos One*, vol. 11, No. 9, e0162726, 15 pages (Sep. 2016).
Kujawa, et al., "Adding Insult to Injury: Cochlear Nerve Degeneration after "Temporary" Noise-Induced Hearing Loss," *J. Neurosci.*, vol. 29, No. 45, pp. 14077-14085 (Nov. 2009).
Sergeyenko, et al., "Age-Related Cochlear Synaptopathy: An Early-Onset Contributor to Auditory Functional Decline," *The Journ. Of Neuroscience*, vol. 33, No. 34, pp. 13686-13694 (Aug. 2013).
Selkoe, "Alzheimer's disease is a synaptic failure," *Science*, vol. 298(5594), pp. 789-791 (Oct. 2002). [Abstract].
Goldstein, et al., "Chronic Traumatic Encephalopathy in Blast-Exposed Military Veterans and a Blast Neurotrauma Mouse Model," *Sci. Transl. Med.*, vol. 4, No. 134, 34 pages (May 2012).

(Continued)

*Primary Examiner* — Pancham Bakshi
(74) *Attorney, Agent, or Firm* — Gilberto M. Villacorta; Tianran Yan; Foley & Lardner LLP

(57) ABSTRACT

Disclosed here is a method for enhancing synaptogenesis and/or neuritogenesis, reducing neurodegeneration, and/or reducing accumulation or aggregation of Tau proteins in a subject suffering from cochlear synaptopathy or vestibular synaptopathy or a central nervous system disease or condition, comprising administering to said subject in need thereof an effective amount of 2,4-disulfonyl α-phenyl tertiary butyl nitrone (2,4-DSPBN) or a pharmaceutically acceptable salt thereof. The method may further comprise administrating N-acetylcysteine (NAC) to the subject.

26 Claims, 40 Drawing Sheets

(56) References Cited

OTHER PUBLICATIONS

Sheng, et al., "Synapses and Alzheimer's Disease," *Cold Spring Harbor Perspectives in Biology*, vol. 4, a005777, 18 pages, (2012).
Jensen, et al., "Immediate and Delayed Cochlear Neuropathy after Noise Exposure in Pubescent Mice," *Plos One*, DOI: 10.1371/journal.pone.0125160, 17 pages (May 2015).
Buée, et al., "Tau protein isoforms, phosphorylation and role in neurodegenerative disorders," *Brain Research*, vol. 33, No. 1, pp. 95-130 (Aug. 2000).
Gao, et al., "Vibration of the organ of Corti within the cochlear apex in mice," *Journ. Of Neurophysiology*, vol. 112, No. 5, pp. 1192-1204 (Jun. 2014).
International Search Report issued in corresponding PCT Application No. PCT/US2017/58834, dated Jan. 9, 2018.

\* cited by examiner

METHODS FOR ENHANCING SYNAPTOGENESIS AND NEURITOGENESIS

CROSS REFERENCE TO RELATED APPLICATIONS

This application claims priority to U.S. Provisional Application No. 62/415,101 filed Oct. 31, 2016, U.S. Provisional Application No. 62/488,740 filed Apr. 22, 2017, U.S. Provisional Application No. 62/510,596 filed May 24, 2017, and U.S. Provisional Application No. 62/550,345 filed Aug. 25, 2017, each of which is incorporated herein by reference in its entirety.

BACKGROUND

Chronic diseases such as chronic hearing loss, tinnitus, hyperacusis, presbycusis, or balance disorders are often associated with noise- and/or age-related cochlear synaptopathy and vestibular synaptopathy in the patients that is independent of hair cell loss. For example, Kujawa et al., *J. Neurosci.*, 29:14077-14085 (2009) and Lin et al., *JARO*, 12:605-616 (2011) demonstrated that noise-induced inner hair cell neurite loss (e.g., synaptopathy) can be extensive despite a normal hair cell complement in mouse and guinea pig models of mild noise trauma. This mechanism likely contributes to hearing disorders caused by noise injuries or cumulative age-related hearing loss (e.g., presbycusis).

Sergeyenko et al., *J. Neurosci.*, 33:13686-13694 (2013) demonstrated that cochlear synapse loss progresses from youth to old age and is seen throughout the cochlea long before age-related changes in thresholds or hair cell counts in a mouse model of presbycusis. Moreover, Makary et al., *JARO*, 12:711-717 (2011) demonstrated that, in aging human ears with full complements of hair cells, mean spiral ganglion cell losses (SGCs, i.e., cochlear neurons) reach about 30% at 95 years, indicating that neurodegeneration can precede and/or occur independently of hair cell loss. Furthermore, in a related study in humans, Viana et al., *Hear Res.*, 327:78-88 (2015) provided evidence that cochlear synaptopathy and the degeneration of peripheral nerve axons occur independently of hair cell loss and likely contribute to presbycusis. These types of diffuse synapse or SGC loss, although they may not necessarily affect hearing thresholds, contribute to processing difficulties and hearing in a noisy environment or lead to related maladaptive sequelae such as tinnitus or hyperacusis. Cochlear synaptopathy and the functional consequences thereof are also described in Schaette et al., *J. Neurosci.*, 31:13452-13457 (2011); Wan et al., *Hear Res.*, 329:1-10 (2015); and Liberman et al., *PLoS One*, 11(9):e0162726 (2016).

Blast injuries to the ear are very common in modern military operations due to improvised explosive devices (IEDs), which can cause sensorineural hearing loss and tinnitus. Tinnitus and hearing loss are the most prevalent adverse medical conditions reported among veterans with service-connected disabilities. Blast exposures can also induce injuries to the central auditory system, and persistent oxidative stress is believed to play a fundamental role in this pathophysiological response.

Tauopathies and cochlear neurodegeneration share oxidative stress as a common pathophysiological correlate and potential propagator of ongoing damage. More specifically, several studies have revealed that oxidative stress acts as a direct catalyst for inducing both hyperphosphorylation and aggregation of Tau. This correlation is further supported by work in superoxide dismutase 2 null mice, which exhibit constitutive hyperphosphorylation of Tau under conditions of chronic oxidative stress as an early postnatal pathological event that can be efficiently mitigated by high-dose catalytic antioxidant treatment. Consistent with this mechanistic vantage point, therapeutically-targeting oxidative stress using antioxidants has proven to be ameliorative among a broad spectrum of Tauopathies.

Further, Selkoe, *Science*, 198:789-791 (2002) observed that Alzheimer's disease begins with hippocampal synaptic dysfunction prior to neuronal degeneration, that the synaptic dysfunction is caused by diffusible oligomeric assemblies of the amyloid beta protein, and that at least one mouse line had shown the impairment to be caused by a significant reduction in synaptic number. Sheng et al., *Cold Spring Harb Perspect Biol*, 4:a005777 (2012) discussed two major themes of pathogenesis of Alzheimer's disease. First, oligomeric Ab species have strong detrimental effects on synapse function and structure, particularly on the postsynaptic side; and second, decreased presenilin function impairs synaptic transmission and promotes neurodegeneration. In addition, Goldstein et al., *Sci. Transl. Med.*, 4(134):doi: 10.1126/scitranslmed.3003716 (2012) reported evidence of chronic traumatic encephalopathy (CTE) in wild-type C57BL/6 mice 2 weeks after exposure to a single blast, that was similar to the CTE neuropathology observed in American football players, and disclosed that blast-induced persistent hippocampal-dependent learning and memory deficits correlated with impaired axonal conduction and defective activity-dependent long-term potentiation of synaptic transmission. These observations highlight the importance of synaptogenesis and neuritogenesis for treatment of Alzheimer's disease, CTE and other central nervous system diseases.

Therefore, a need exists for methods of enhancing synaptogenesis and neuritogenesis in patients suffering from cochlear synaptopathy or vestibular synaptopathy or a central nervous system disease or condition, in particular cochlear synaptopathy or vestibular synaptopathy associated with chronic hearing loss, tinnitus, hyperacusis, presbycusis, or balance disorders. Also, the neurodegeneration and Tau protein aggregation (e.g., caused by blast exposure) highlights another need for methods of reducing neurodegeneration and Tau protein accumulation or aggregation.

SUMMARY

The present inventors successfully met the aforementioned medical need by providing methods and compositions for enhancing synaptogenesis and neuritogenesis in patients suffering from cochlear synaptopathy or vestibular synaptopathy. Accordingly, at least one aspect of the invention described herein relates to a method for enhancing synaptogenesis and neuritogenesis in a subject suffering from cochlear synaptopathy or vestibular synaptopathy, comprising administering to said subject in need thereof an effective amount of 2,4-disulfonyl α-phenyl tertiary butyl nitrone (2,4-DSPBN) or a pharmaceutically acceptable salt thereof. The disclosure also provides a method of reducing neurodegeneration or accumulation of Tau proteins in a subject, comprising administering to said subject an effective 2,4-DSPBN or a pharmaceutical acceptable salt thereof.

In some embodiments, the 2,4-DSPBN or pharmaceutically acceptable salt thereof is administered as a pharmaceutical composition, including a pharmaceutically acceptable carrier.

In some embodiments, the 2,4-DSPBN or pharmaceutically acceptable salt thereof is administered to the subject orally, intravenously, subcutaneously, sublingually, subdermally, intrathecally, by inhalation, or locally within an ear.

In some embodiments, the method further comprises administering one or more compounds selected from the group consisting of N-acetylcysteine (NAC), Acetyl-L-Carnitine, glutathione monoethylester, ebselen, D-methionine, carbamathione and Szeto-Schiller peptides and their functional analogs.

In some embodiments, the method further comprises administering NAC.

In some embodiments, the subject suffers from a chronic auditory injury or chronic hearing loss. In some embodiments, the chronic auditory injury or chronic hearing loss is caused by aging.

In some embodiments, the chronic auditory injury or chronic hearing loss is caused by exposure to blast or noise, either acute or chronic. In some embodiments, the 2,4-DSPBN or pharmaceutically acceptable salt thereof is administered to the subject at least one month after the exposure to blast or noise. In some embodiments, the 2,4-DSPBN or pharmaceutically acceptable salt thereof is administered to the subject at least one year after the exposure to blast or noise.

In some embodiments, the chronic auditory injury or chronic hearing loss is caused by infection. In some embodiments, the 2,4-DSPBN or pharmaceutically acceptable salt thereof is administered to the subject at least one month after the infection. In some embodiments, the 2,4-DSPBN or pharmaceutically acceptable salt thereof is administered to the subject at least one year after the infection.

In some embodiments, the chronic auditory injury or chronic hearing loss is caused by exposure to toxin. In some embodiments, the 2,4-DSPBN or pharmaceutically acceptable salt thereof is administered to the subject at least one month after the exposure to toxin. In some embodiments, the 2,4-DSPBN or pharmaceutically acceptable salt thereof is administered to the subject at least one year after the exposure to toxin.

In some embodiments, the subject suffers from tinnitus.

In some embodiments, the subject suffers from hyperacusis.

In some embodiments, the subject suffers from presbycusis.

In some embodiments, the subject suffers from a balance disorder. In some embodiments, the subject suffers from Meniere's disease with synapse loss.

In some embodiments, the administration of the 2,4-DSPBN or pharmaceutically acceptable salt thereof leads to regeneration of cochlear neurites or vestibular neurites in the subject. In some embodiments, the number of viable nerve connections on inner hair cells is increased. In some embodiments, the number of synapses in tonotopic regions in the organ of Corti is increased.

In some embodiments, the patient has not suffered a substantial loss of cochlear hair cells or vestibular hair cells.

At least another aspect of the invention described herein relates to a method for enhancing synaptogenesis and neuritogenesis in a subject suffering from a central nervous system disease or condition, comprising administering to said subject in need thereof an effective amount of 2,4-disulfonyl α-phenyl tertiary butyl nitrone (2,4-DSPBN) or a pharmaceutically acceptable salt thereof.

In some embodiments, the 2,4-DSPBN or pharmaceutically acceptable salt thereof is administered as a pharmaceutical composition, including a pharmaceutically acceptable carrier. In some embodiments, the 2,4-DSPBN or pharmaceutically acceptable salt thereof is administered to the subject orally, intravenously, subcutaneously, sublingually, subdermally, intrathecally, by inhalation, or locally within an ear. In some embodiments, the method further comprises co-administering NAC to said subject.

In some embodiments, the subject suffers from a central nervous system disease or condition selected from Alzheimer's disease, Parkinson's disease, progressive supranuclear palsy, frontotemporal dementia, Pick's disease, Argyrophilic grain dementia, corticobasal degeneration, progressive subcortical gliosis, amyotrophic lateral sclerosis, diffuse neurofibrillary tangles with calcification, chronic traumatic encephalopathy, dementia pugilistica, tangle-only dementia, Down's syndrome, Gerstmann-Straussler-Scheinker disease, Hallervorden-Spatz disease, Creutzfeldt-Jakob disease, multiple system atrophy, Niemann-Pick disease type C, prion protein cerebral amyloid angiopathy, subacute sclerosing panencephalitis, myotonic dystrophy, non-Guamanian motor neuron disease with neurofibrillary tangles, and postencephalitic parkinsonism.

These and other features, together with the organization and manner of operation thereof, will become apparent from the following detailed description when taken in conjunction with the accompanying drawings.

, * indicate p<0.01 and 0.001 between treated and untreated blast-exposed animals. ### indicates p<0.001 comparing HPN-07/NAC-mediated reductions in ABR threshold shift at 7-days (7D) or 21-days (21D) post-blast with that observed at 24 hour (24H) post-blast. Error bars indicate SEM.

Figure 21:
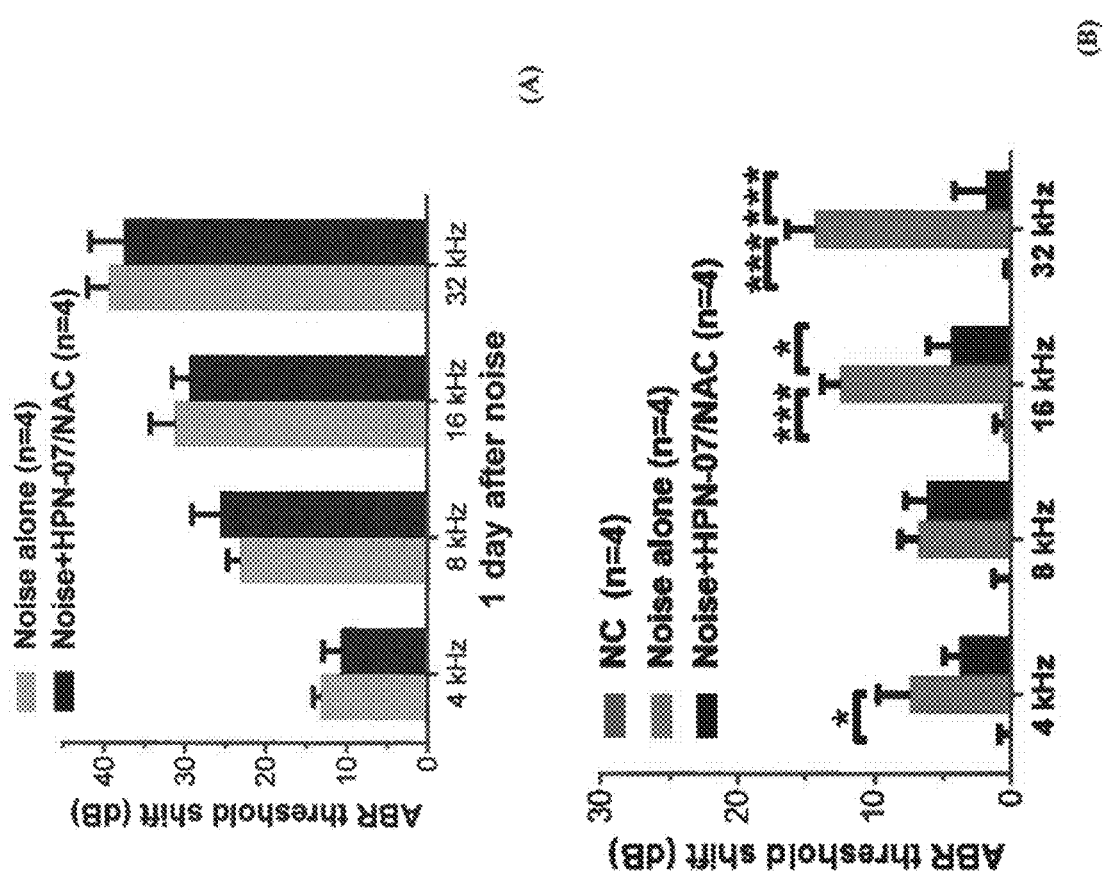

FIG. 21 shows HPN-07 and NAC attenuated noise-induced hearing loss. (A) ABR threshold shifts 1 day after noise; (B) ABR threshold shifts 15 days after noise. Hearing loss caused by noise was attenuated with the HPN-07/NAC treatment. * and *** represent p<0.05 and 0.001, respectively, significant sample effects at any given frequency for the two-way ANOVA followed by the Bonferroni post-test.

Figure 22:
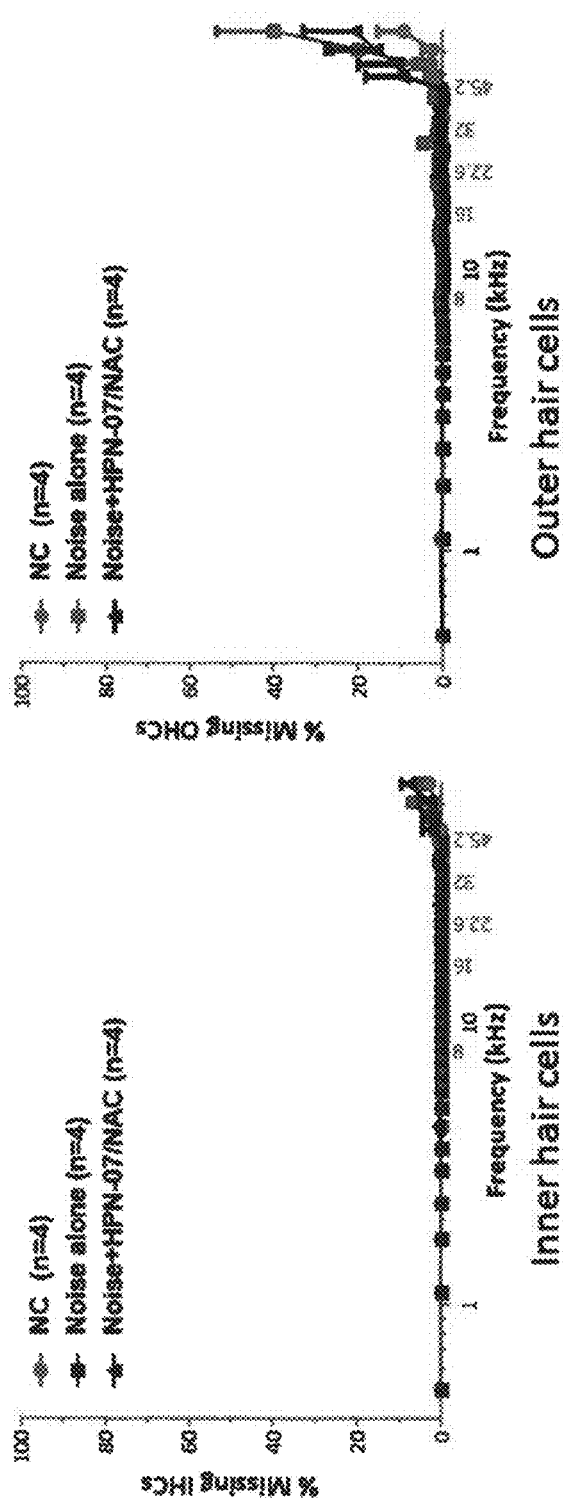

FIG. 22 shows that hair cell loss after noise exposure was minimal and only appeared in the basal region of the cochleae.

Figure 23:
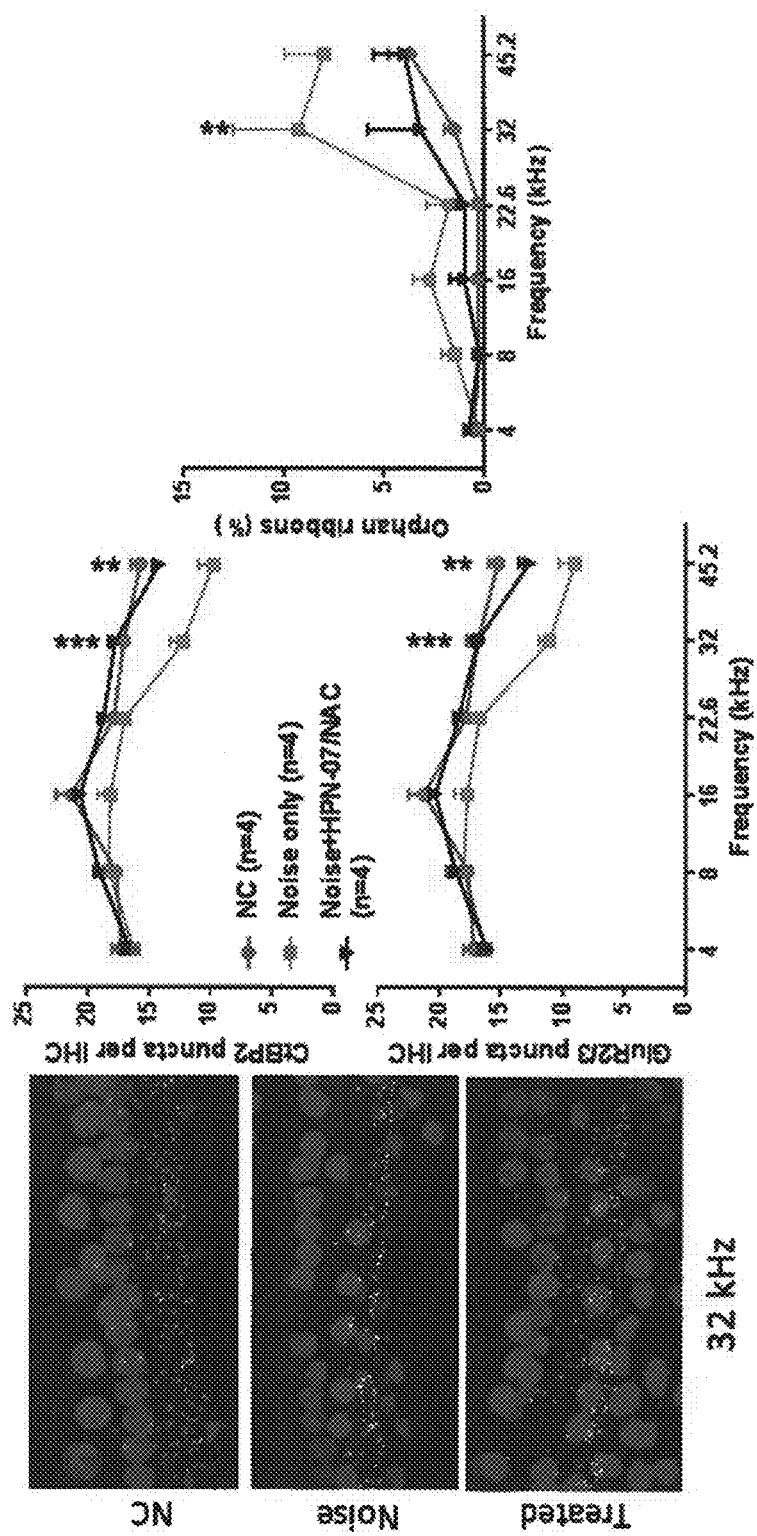

FIG. 23 shows HPN-07 and NAC reversed noise-induced excitotoxic loss of IHC ribbon synapses in vivo. A one-time noise (8-16 kHz for 2 hours at 110 dB) caused 30%-40% loss of synapses at higher frequencies in Sprague Dawley rats. HPN-07/NAC treatment reversed the damage. Comparisons were made between Noise alone group and Noise+HPN-07/NAC group.  and * represent p<0.01 and 0.001, respectively. Twenty-four hours post injury ribbon synapse loss is permanent so recovery must be regenerative.

Figure 24:
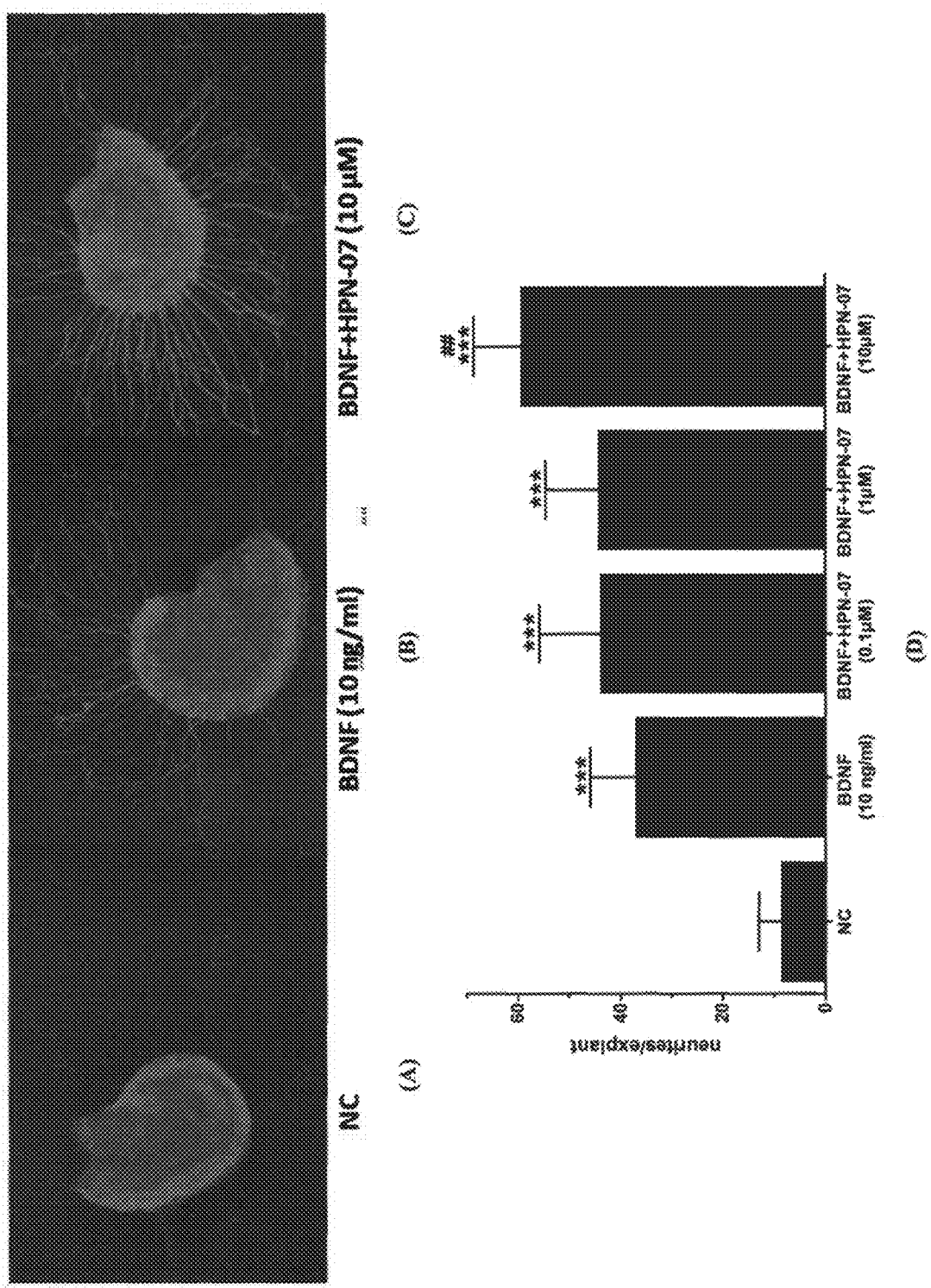

FIG. 24 shows HPN-07 potentiates BDNF-induced neuritogenesis in spiral ganglion neuron explants. Spiral ganglion neurons have inherent, but limited ability to regrow nerve fibers after damage. An intrinsic neurotrophin, brain-derived neurotrophic factor (BDNF), can facilitate the recovery. HPN-07 greatly increased the number and extent of nerve fibers in addition to BDNF. *** represents p<0.001 compared to NC. ## represents p<0.01 compared to BDNF (10 ng/ml).

Figure 25:
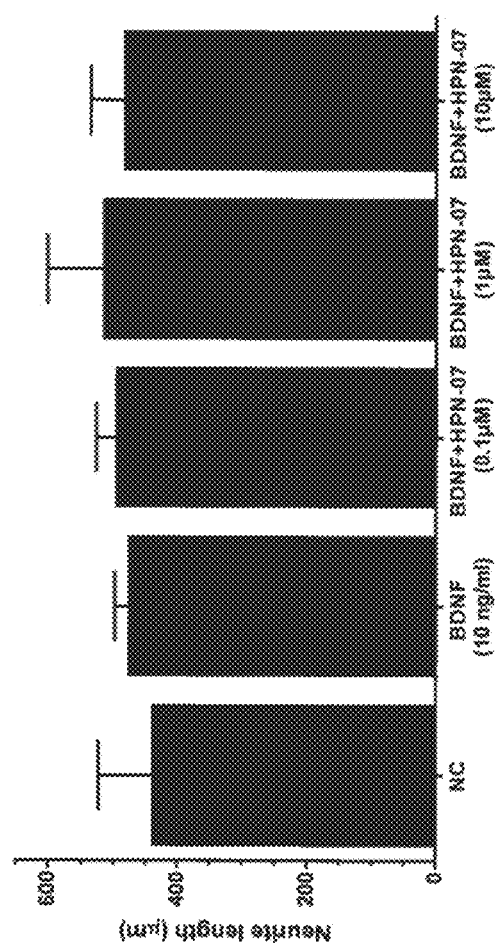

FIG. 25 shows that in the experiment where HPN-07 potentiates BDNF-induced neuritogenesis in spiral ganglion neuron explants, neurite length is not significantly changed with any of the treatments compared to normal control (NC).

Figure 26:
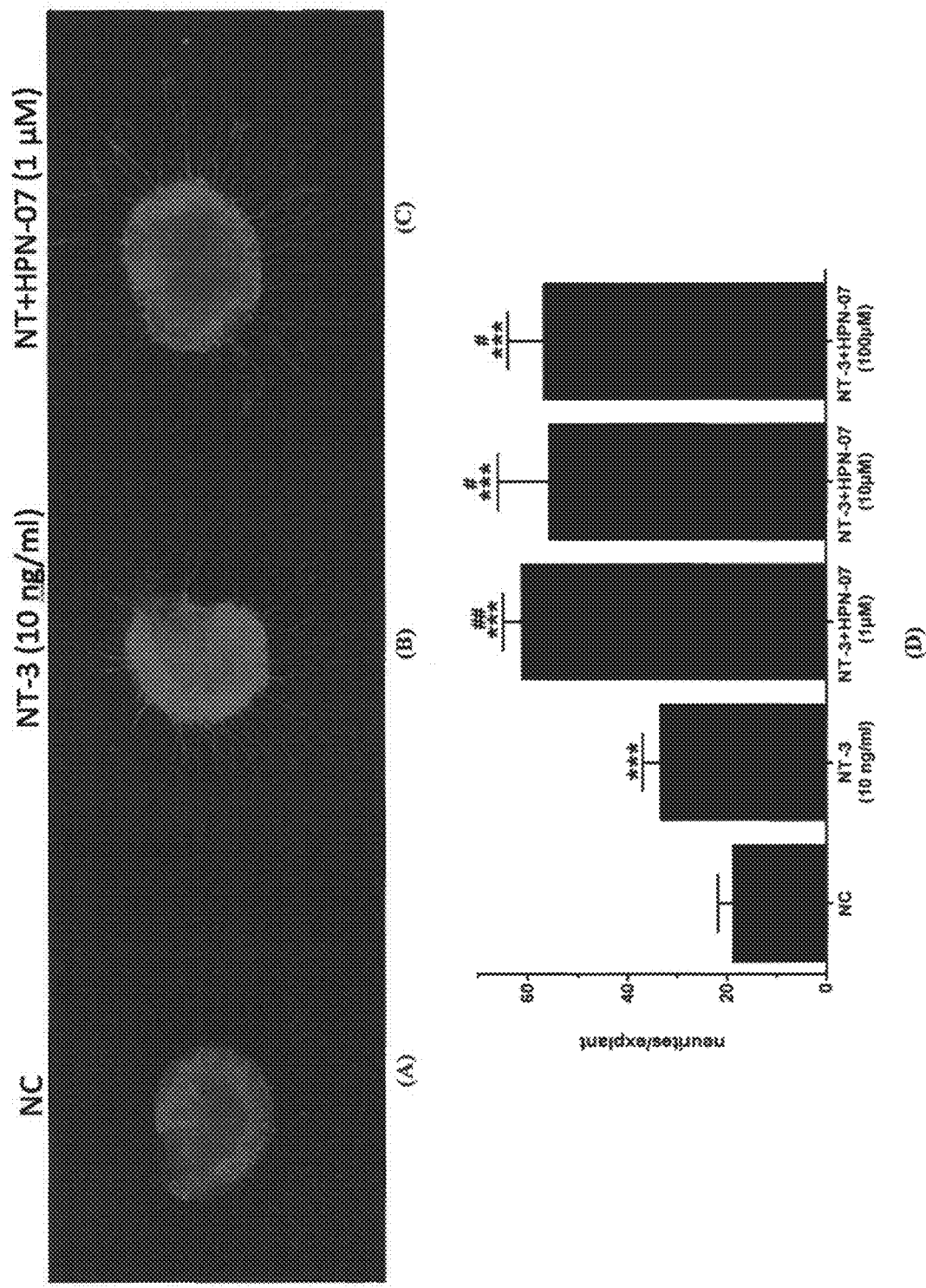

FIG. 26 shows HPN-07 potentiated NT-3 induced neuritogenesis. Similar to BDNF, NT-3 induced neuritogenesis is also enhanced by HPN-07. *** represents p<0.001 compared to NC. # and ## represent p<0.1 and p<0.01, respectively, compared to NT-3 (10 ng/ml).

Figure 27:
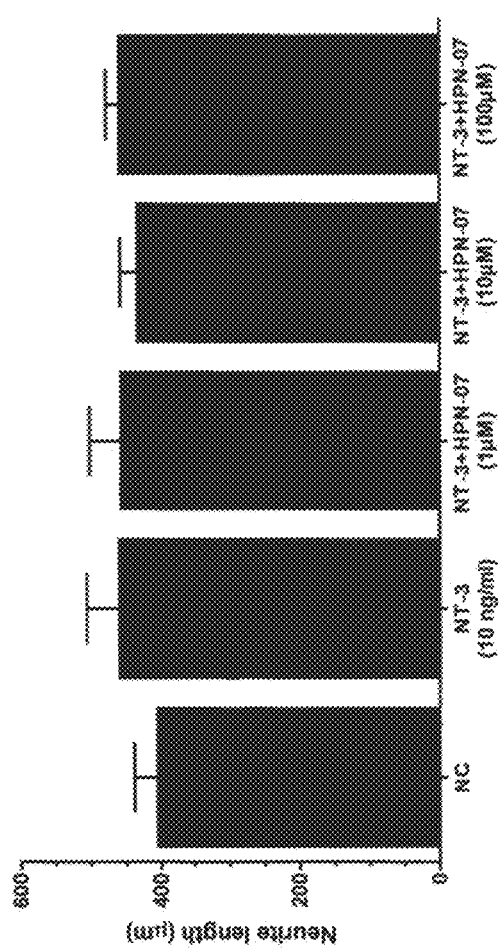

FIG. 27 shows that in the experiment where HPN-07 potentiated NT-3 induced neuritogenesis, neurite length is not significantly changed with any of the treatments compared to normal control (NC).

Figure 28:
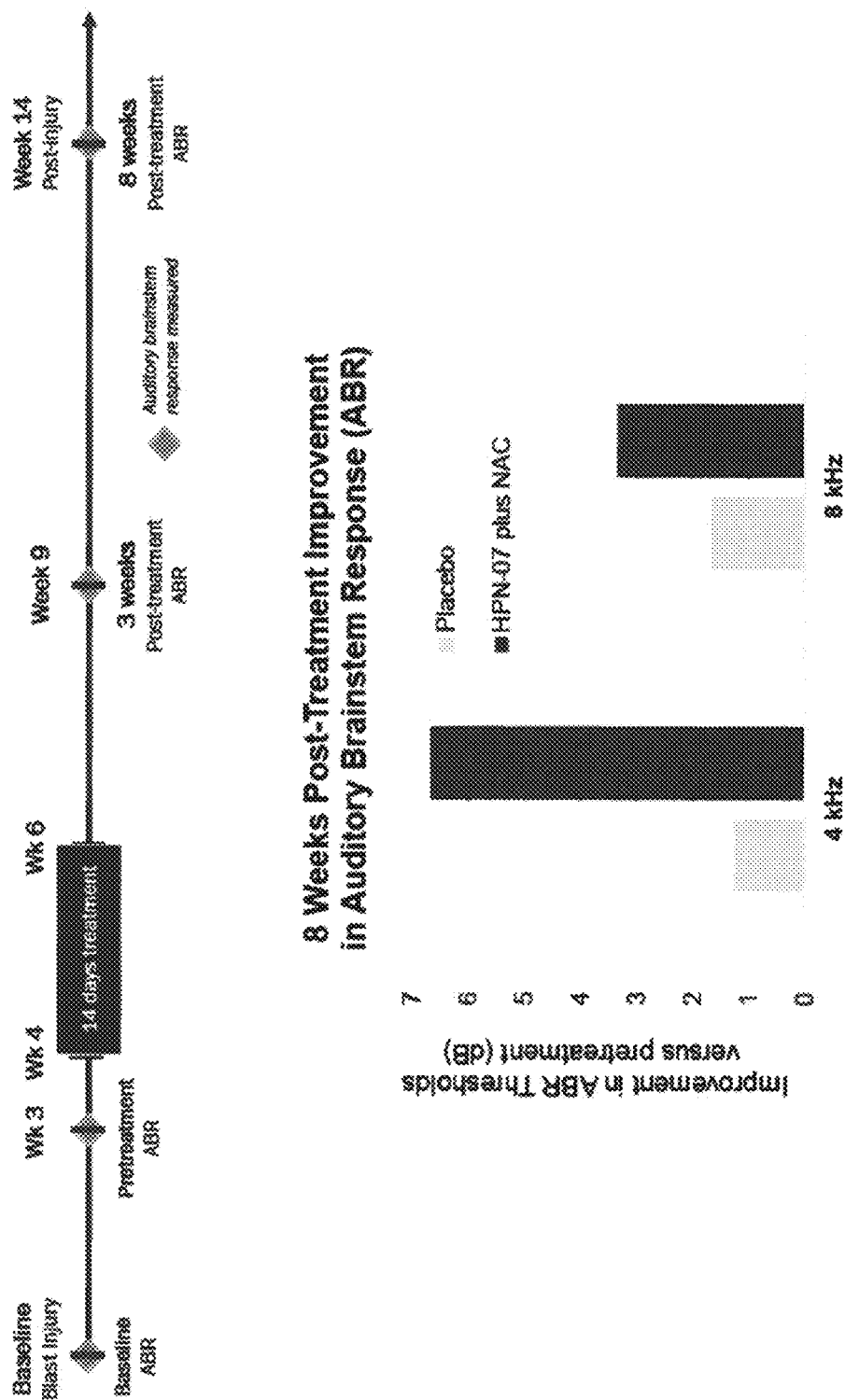

FIG. 28 shows NHPN-1010 treatment (HPN-07 plus NAC) restored hearing function in a pilot study of established hearing loss. Permanent threshold shift was established by open field blast insult. Treatment was initiated at 4 weeks post-injury, with HPN-07 plus NAC dosed at 300 mg/kg twice daily for 14 days. ABR threshold improvements were shown 14 weeks post-injury (8 weeks post-treatment) versus pre-treatment.

Figure 29:
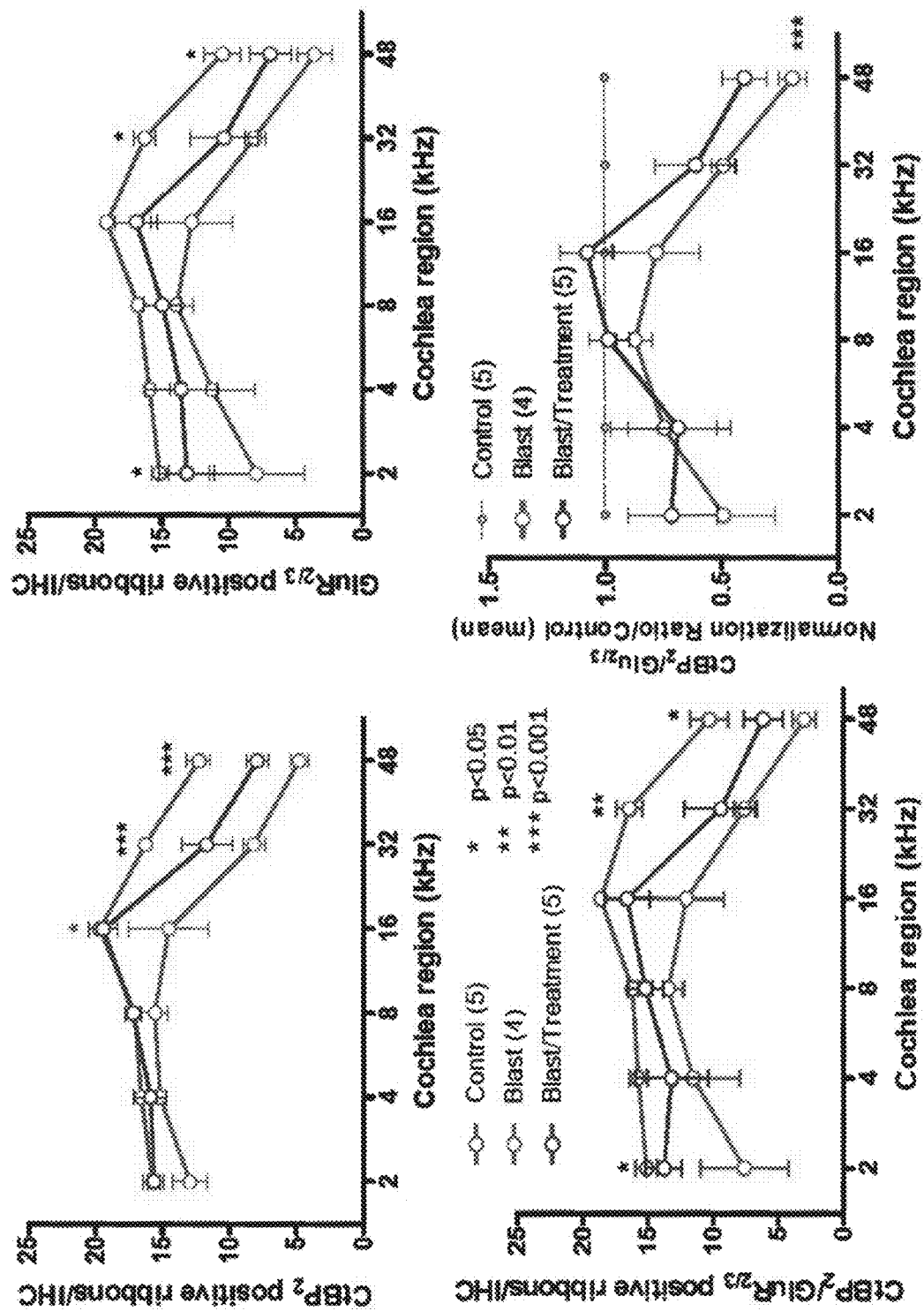

FIG. 29 shows NHPN-1010 treatment (HPN-07 plus NAC) restored IHC ribbon synapse numbers in established, chronic hearing loss model. NHPN-1010 treatment was initiated 4 weeks after injury and dosed daily for 14 days. Ribbon synapse counts were significantly restored 8 weeks post-injury.

Figure 30:
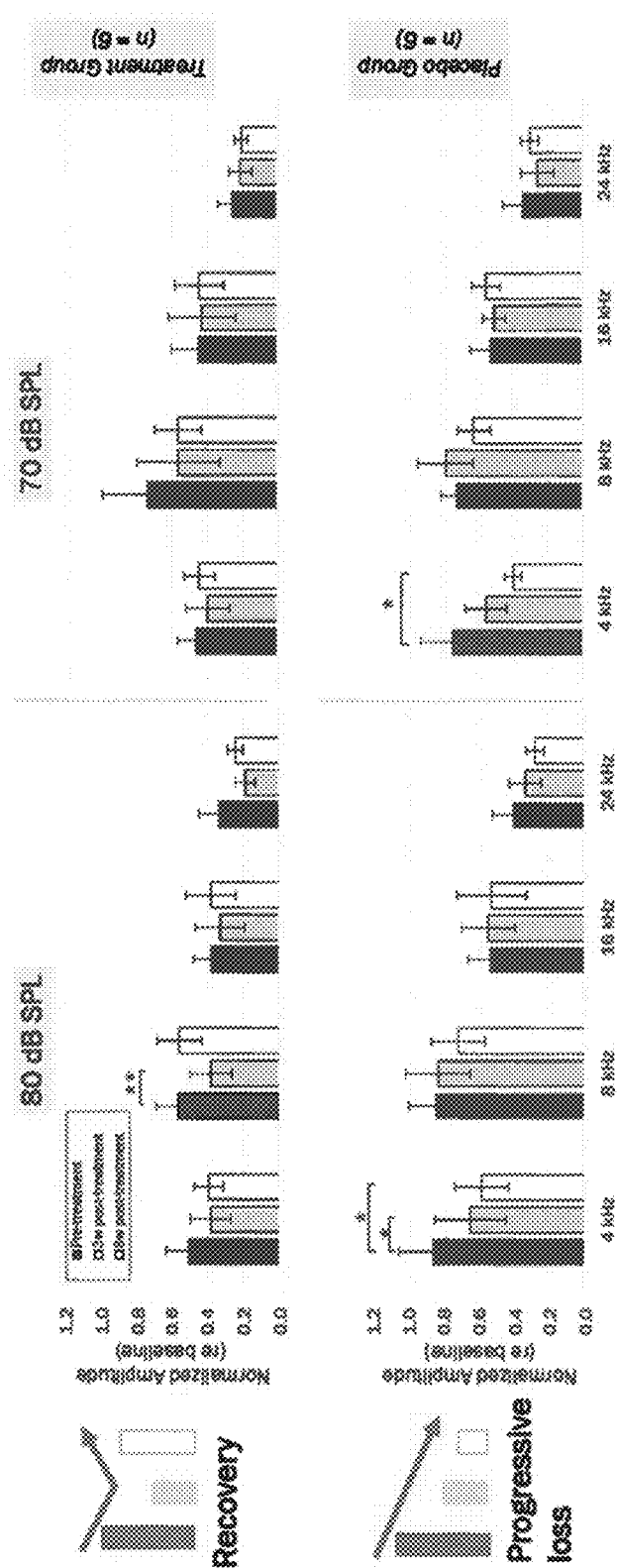

FIG. 30 shows NHPN-1010 treatment (HPN-07 plus NAC) resulted in recovery of ABR Wave I amplitudes in established chronic hearing loss model. The amplitudes in response to the 4 kHz and 8 kHz stimulus at both 80 and 70 dB SPL in the placebo group were reduced by blast exposure and continued to decrease as time progresses. Reduction in the amplitude responding to the 8 kHz stimulus at 80 dB SPL recovered completely to the pre-treatment level at 8 weeks post-NHPN-1010 treatment.

Figure 31:
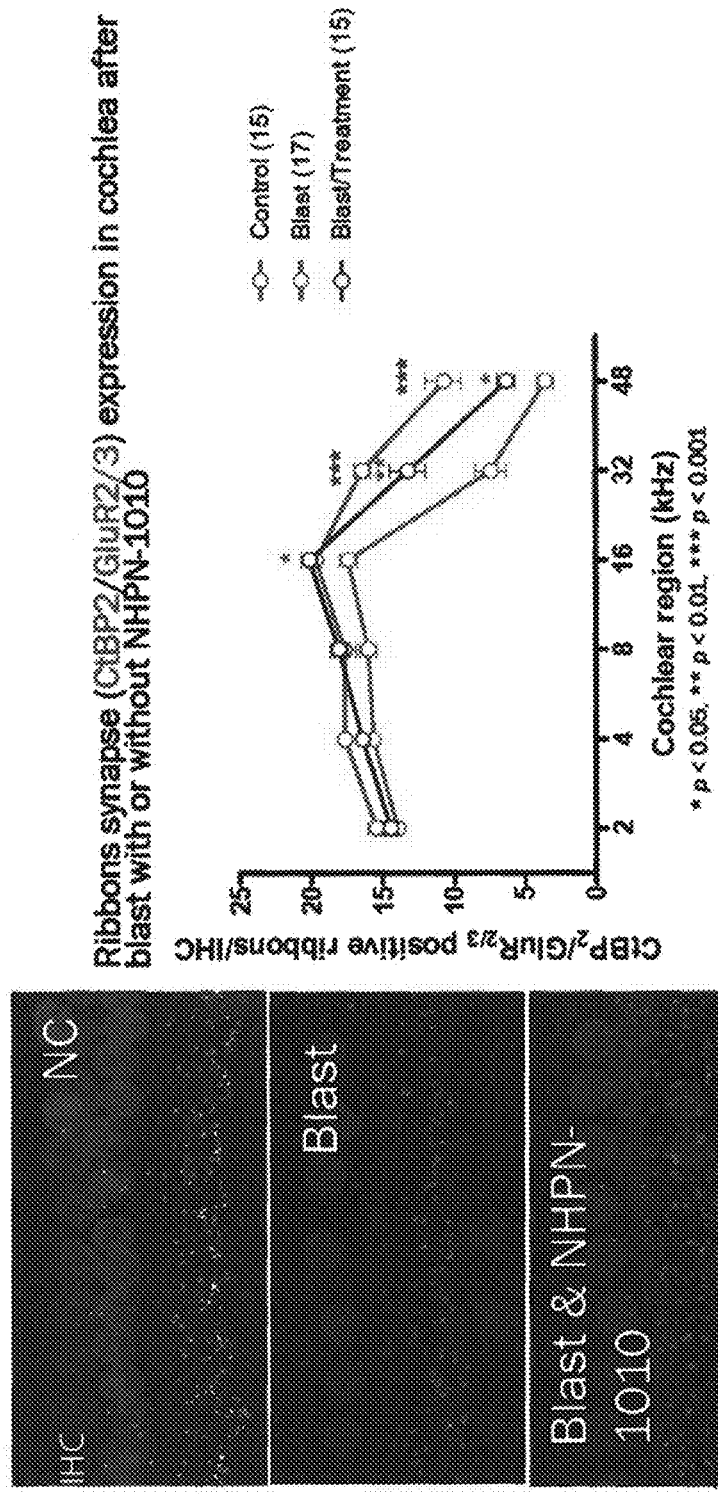

FIG. 31 shows that ribbon synapses were reduced after blast at 16, 32, 48 kHz and preserved/restored with NHPN-1010 treatment (HPN-07 plus NAC).

Figure 32:
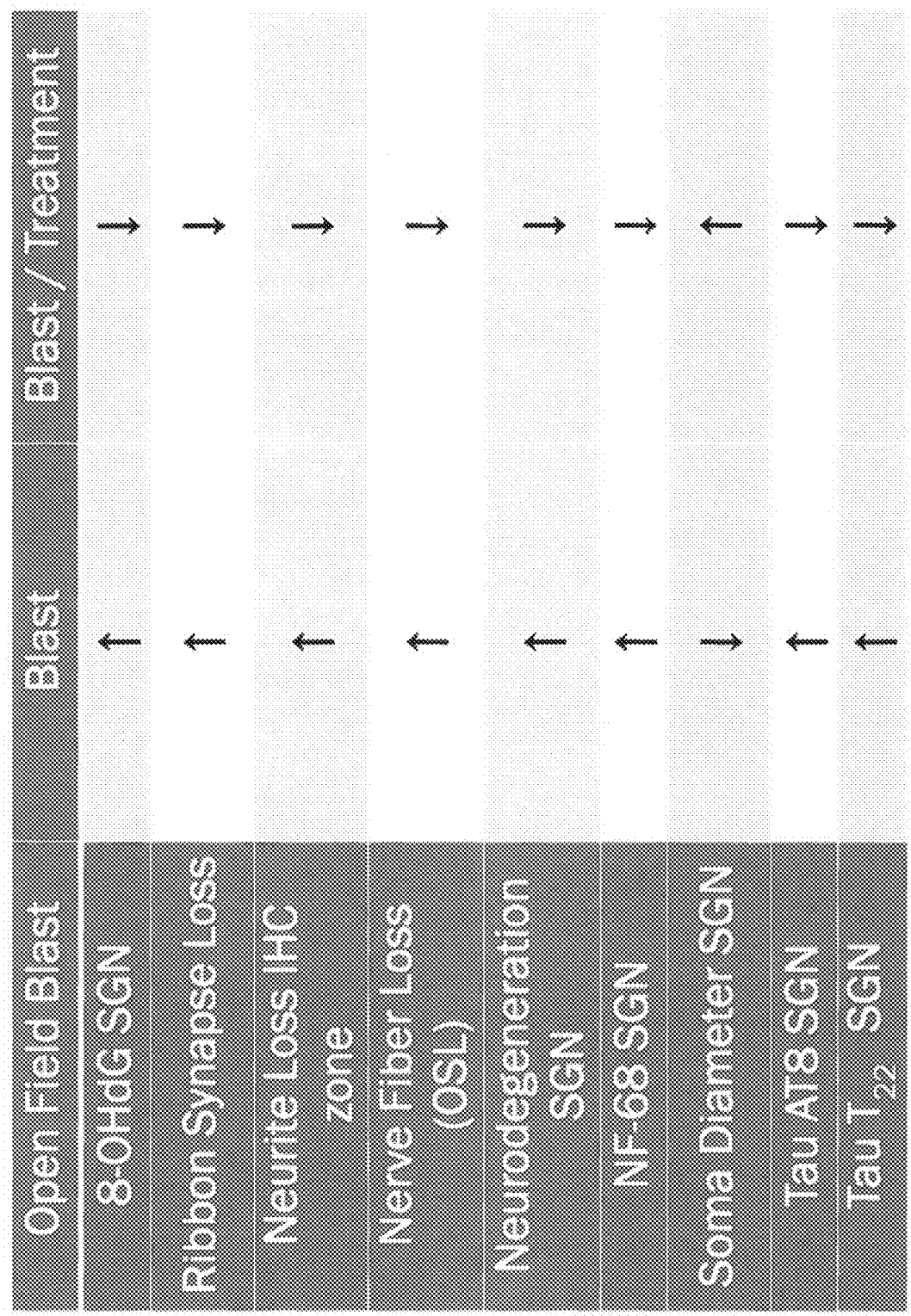

FIG. 32 shows NHPN-1010 treatment (HPN-07 plus NAC) can ameliorate blast effects on primary auditory afferent neurons-reduced retrograde neurodegeneration.

Figure 33:
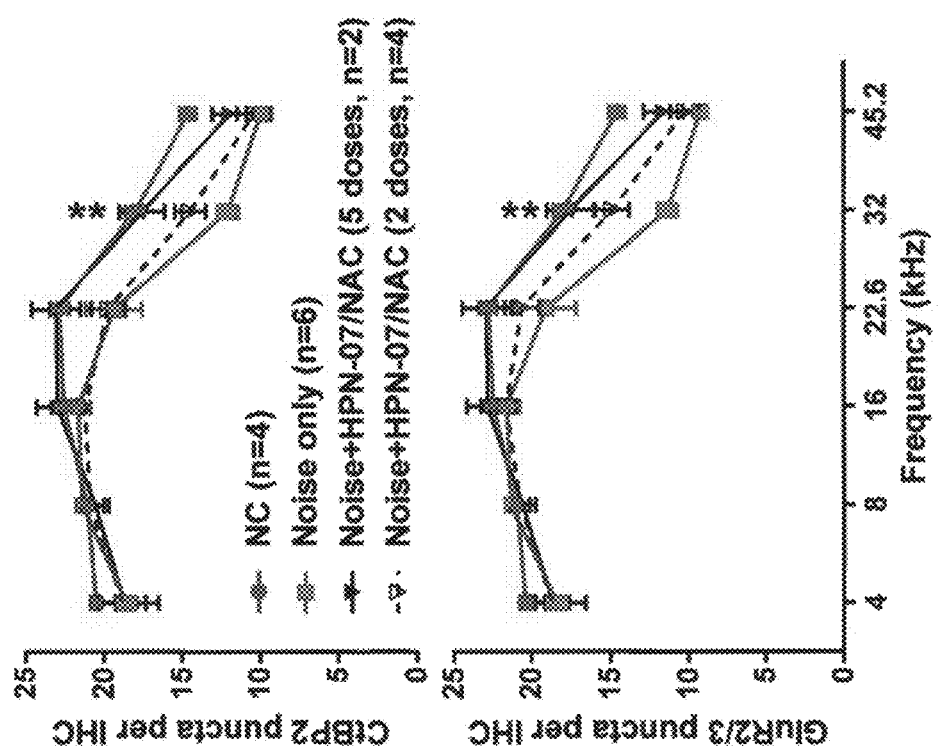

FIG. 33 shows HPN-07 and NAC reversed noise-induced synapse loss in vivo. In this experiment, five doses of HPN-07/NAC treatment appeared to be more effective than two doses in reversing the noise-induced synapse loss. Comparisons were made between Noise alone group and Noise+HPN-07/NAC group (5 doses). ** represents p<0.01.

Figure 34:
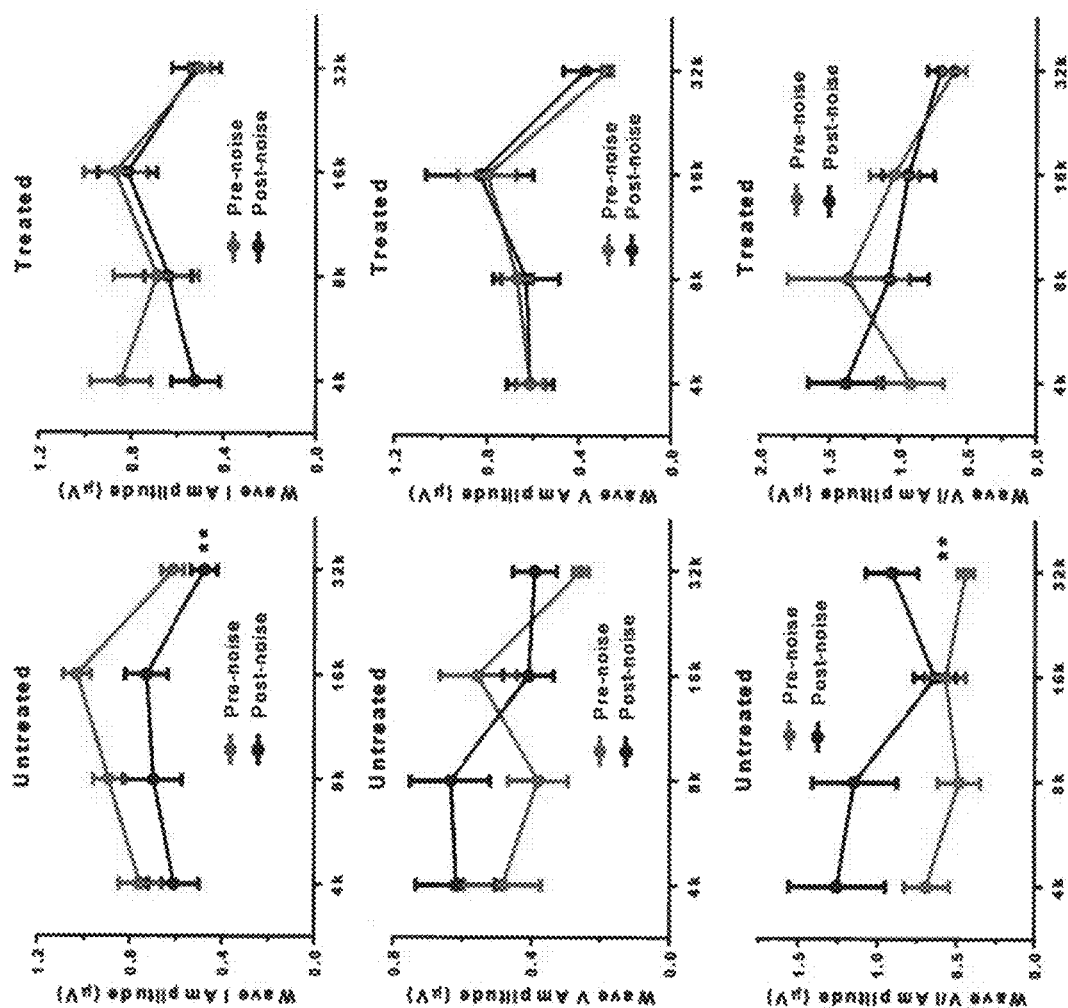

FIG. 34 shows HPN-07/NAC HPN-07/NAC restores noise-induced ABR amplitude abnormality in vivo. ABR wave I amplitudes and wave V/I amplitude ratios of the treated group were unchanged 15 days after noise exposure compared to pre-noise in contrast to the untreated group. Wave V amplitudes of both groups were not changed. ** p<0.01, a significant main effect across frequencies for the repeated measures two-way ANOVA.

Figure 35:
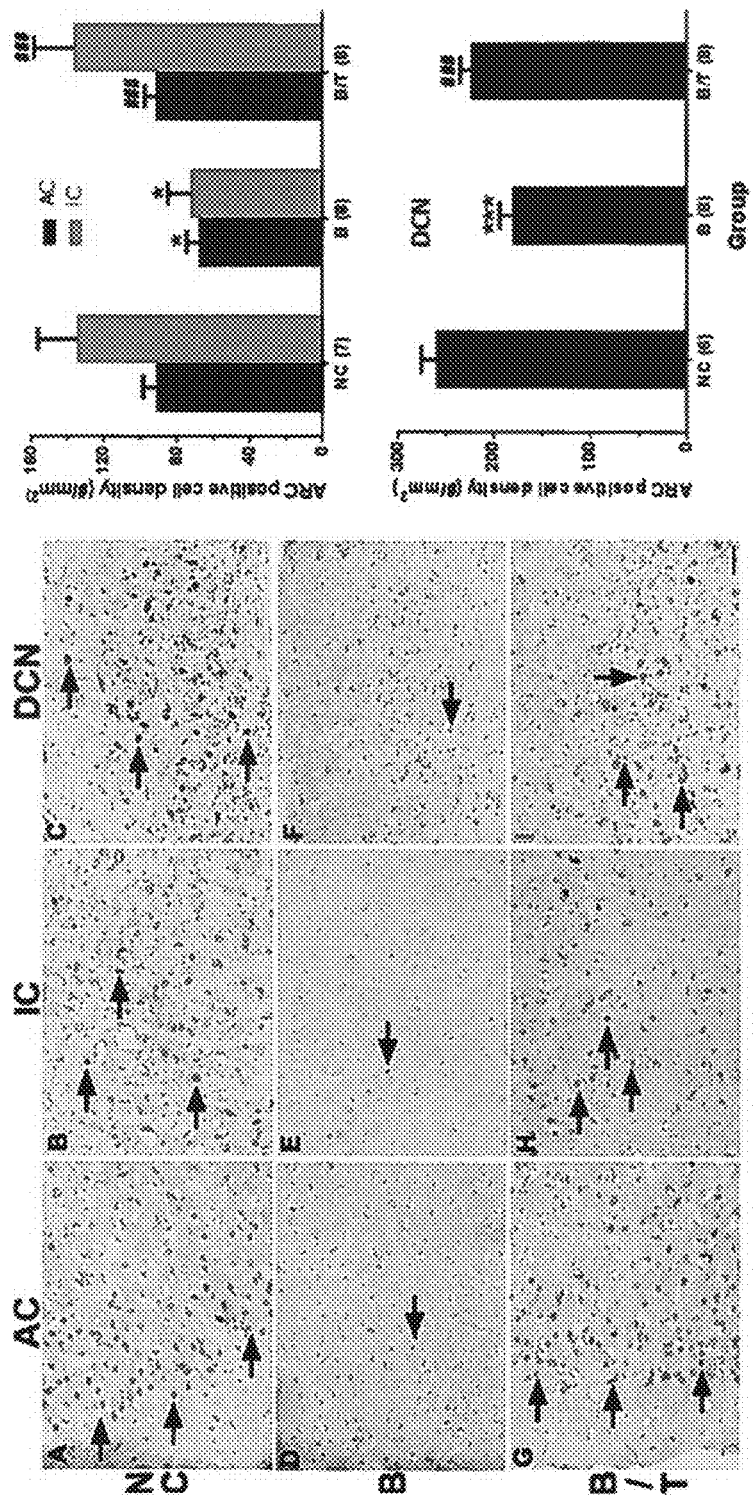

FIG. 35 shows activity-regulated cytoskeleton-associated protein (ARC) immunostaining in the central auditory system. ARC, also known as Arg3.1, is a plasticity protein. Decreased ARC in the central auditory system is associated with tinnitus. The blast exposure down-regulated ARC in the AC, the IC, and the DCN. HPN-07/NAC treatment normalized ARC expression in the AC, the IC and the DCN, compared to the blast group without treatment. *, *** indicate p<0.05 or 0.001 when compared with NC, ### indicate p<0.001 when compared with the blast group without treatment.

Figure 36:
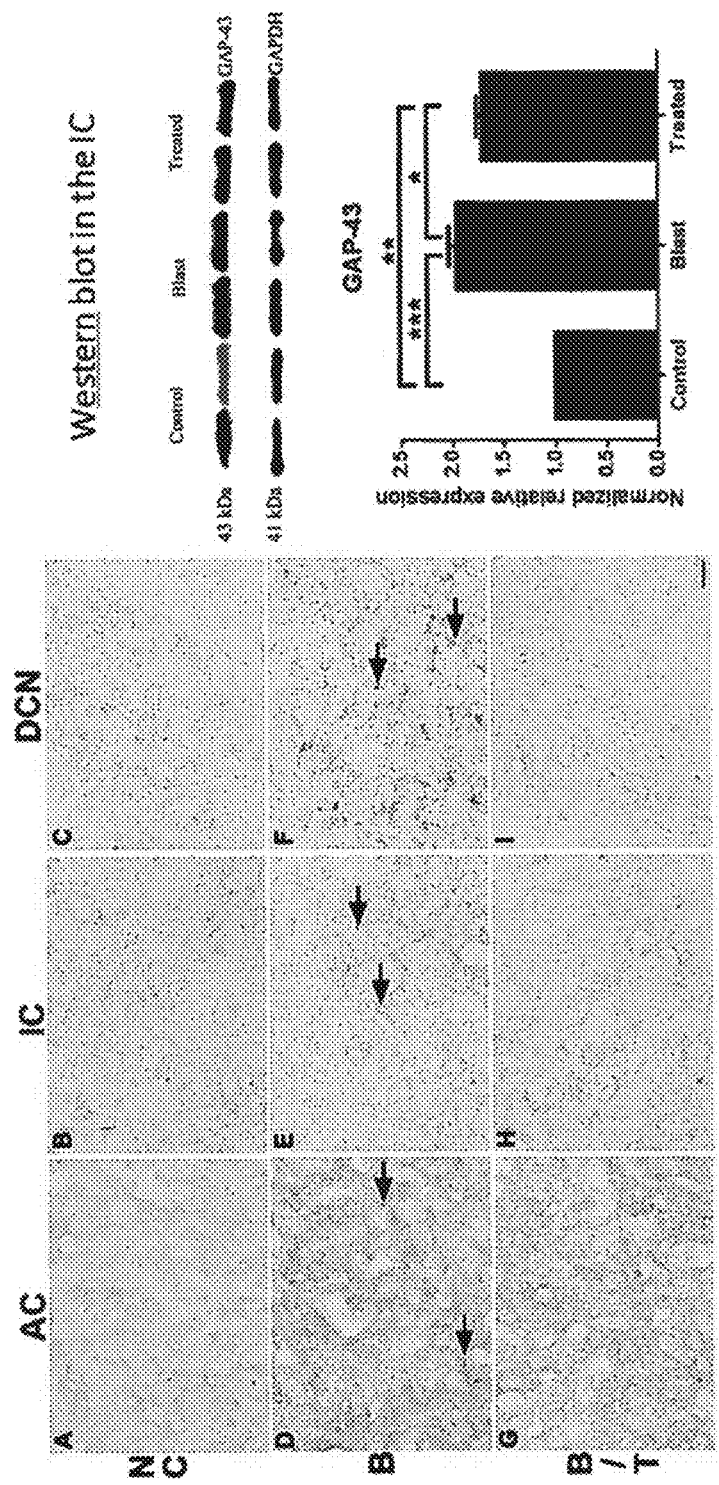

FIG. 36 shows growth associated protein 43 (GAP-43) immunostaining and western blot in the central auditory system. GAP-43 is a membrane associated phosphoprotein located in axonal growth cones. It is a marker for axonal outgrowth, synaptogenesis and synaptic remodeling. The blast exposure up-regulated GAP-43 in the AC, the IC and the DCN. HPN-07/NAC treatment normalized GAP-43 expression in the AC, the IC and the DCN, compared to the blast group without treatment.

Figure 37:
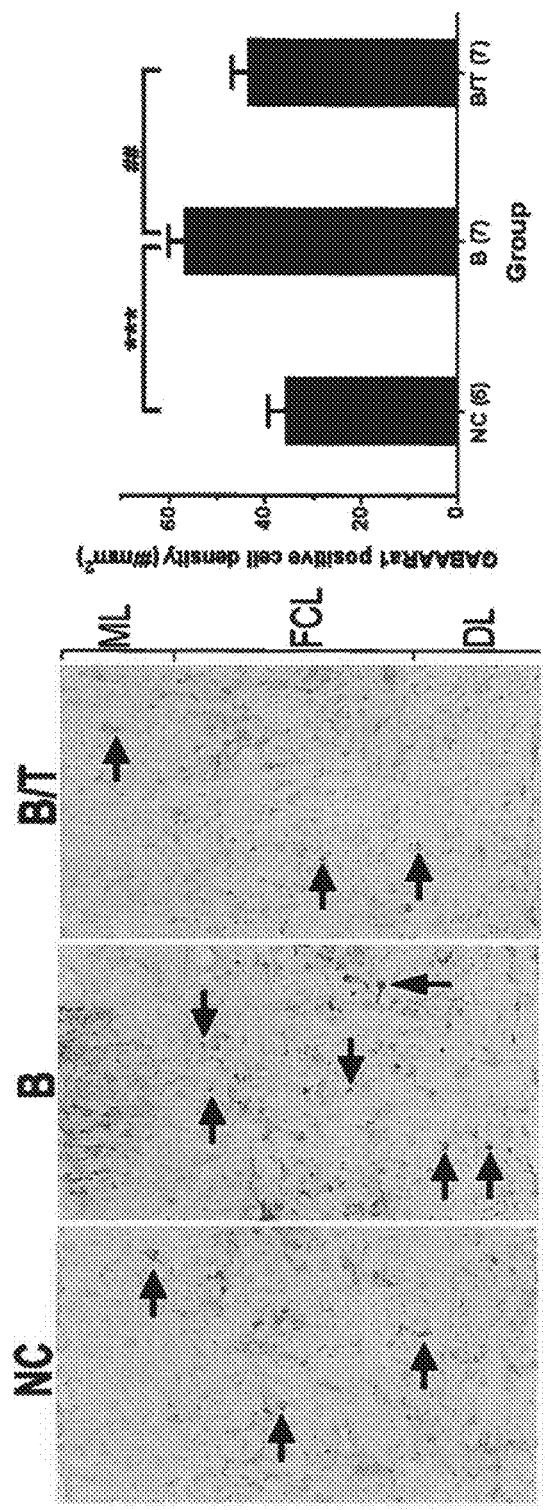

FIG. 37 shows GABAA receptor α1 (GABAA Rα1) immunostaining in the dorsal cochlear nucleus (DCN). GABAA Receptor is an ionotropic receptor and ligand-gated ion channel. Its endogenous ligand is γ-aminobutyric acid (GABA), the major inhibitory neurotransmitter in the central nervous system. The blast exposure up-regulated the expression of GABAA Rα1 in the DCN. HPN-07/NAC treatment normalized the expression of GABAA Rα1 in the DCN, compared to the blast group without treatment.

Figure 38:
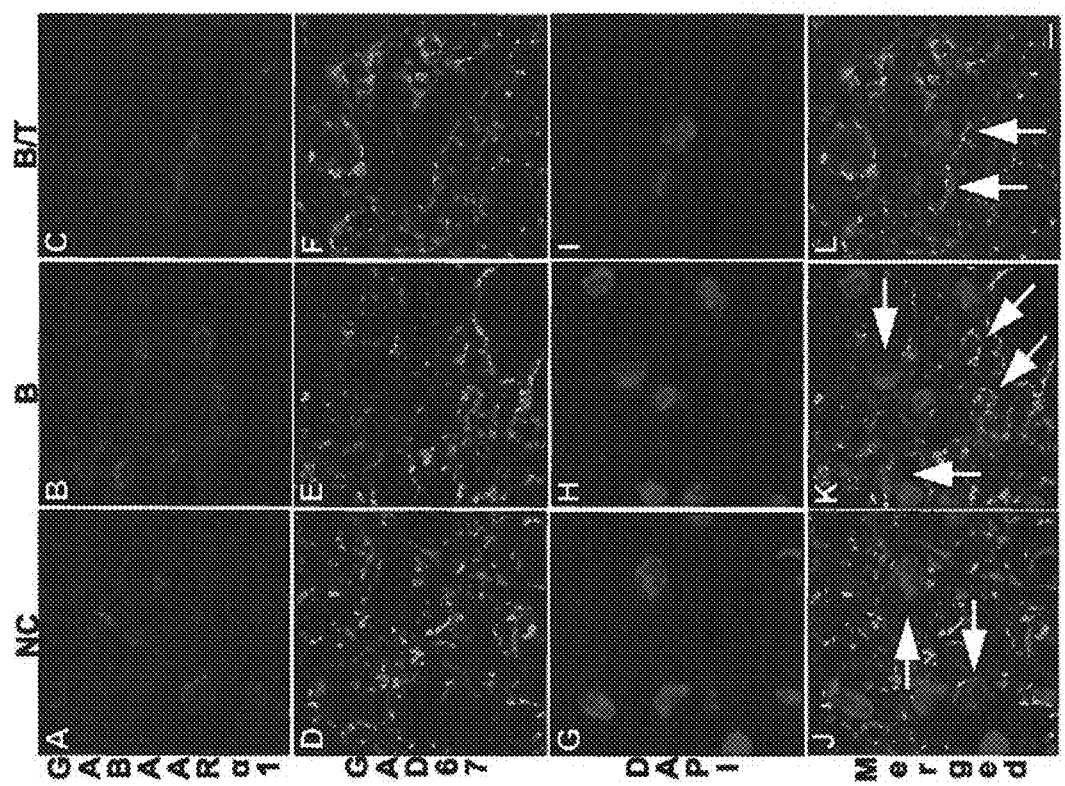

FIG. 38 shows GABAA Rα1 (red) and GAD67 (green) co-labeling in the DCN. GAD67 is a biomarker for inhibitory neurons, indicating GABAA Rα1 positive cells are inhibitory neurons.

Figure 39:
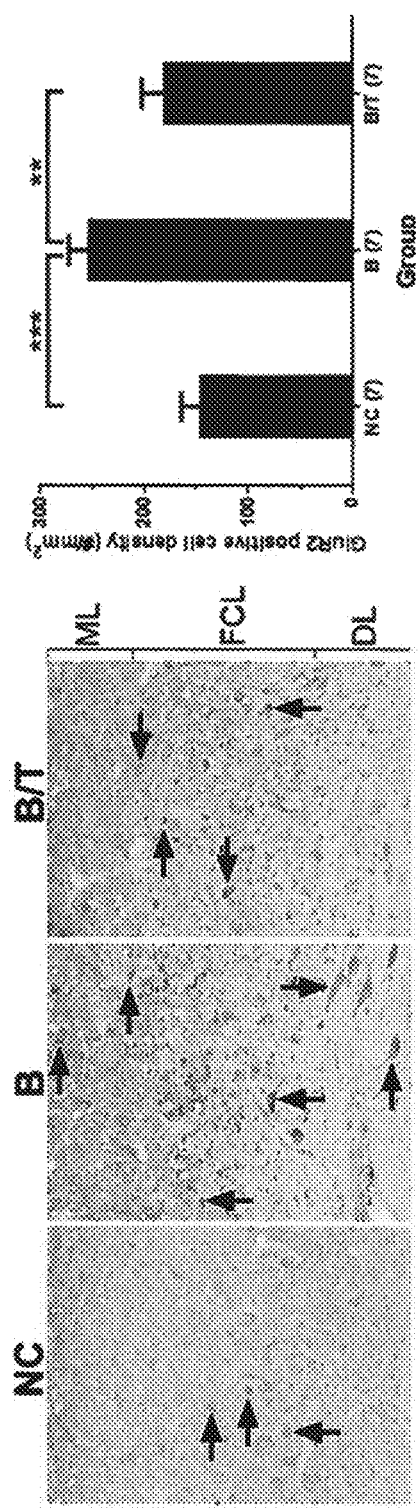

FIG. 39 shows glutamate receptor 2 (GluR2) immunostaining in the DCN. GluR2 is an ionotropic receptor of AMPA, which is a excitatory neurotransmitter in the central nervous system. Overstimulation of glutamate receptors causes neurodegeneration and neuronal damage through excitotoxicity. The blast exposure up-regulated the expression of GluR2 in the DCN. HPN-07/NAC treatment normalized the expression of GluR2 in the DCN, compared to the blast group without treatment.

Figure 40:
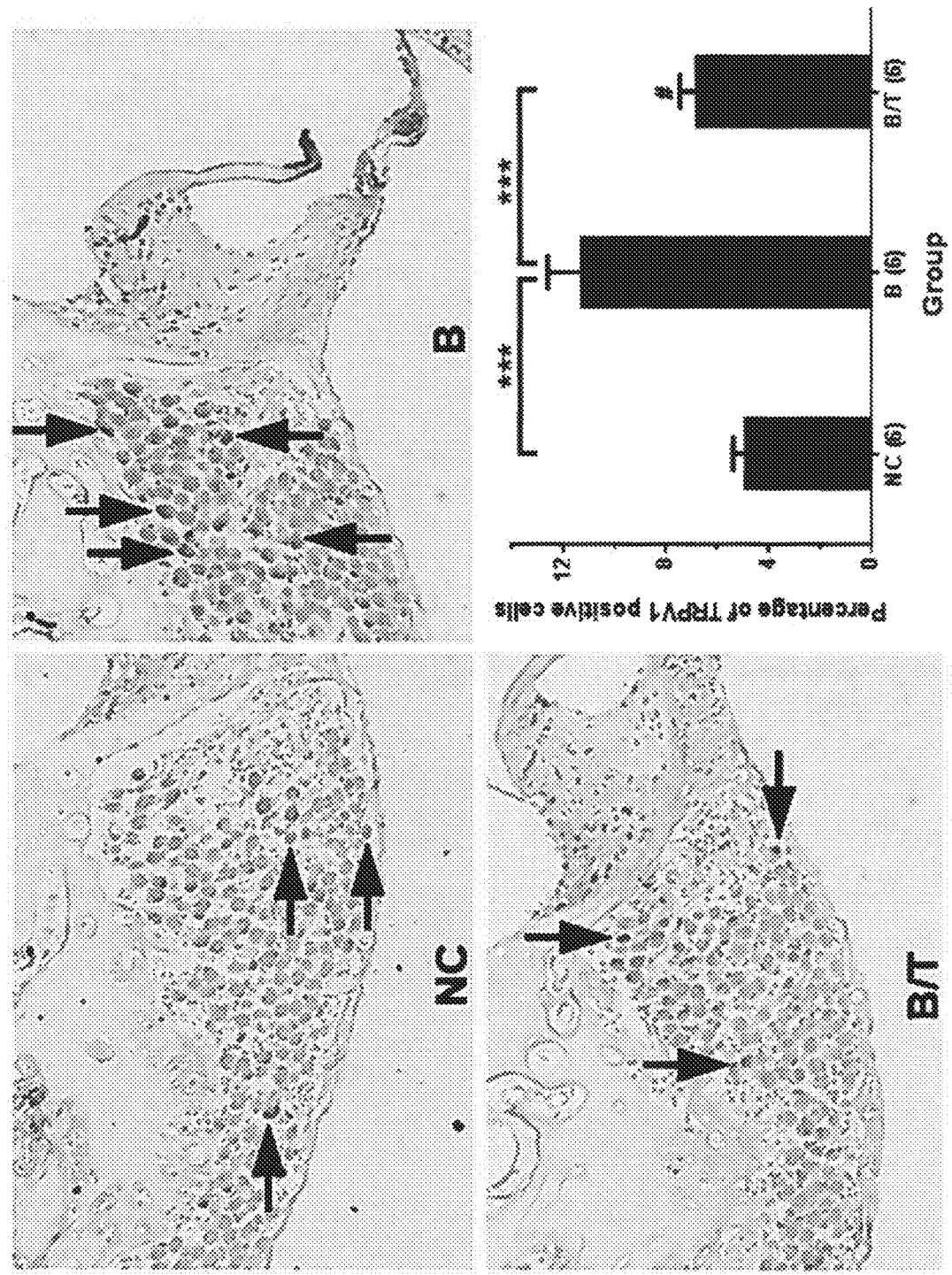

FIG. 40 shows transient receptor potential cation channel subfamily V member 1 (TRPV1) immunostaining in the spiral ganglion (SG). TRPV1, also known as the capsaicin receptor and the vanilloid receptor 1, is activated by high temperature, acidic conditions, Capsaicin, and irritating compounds. Up-regulation of TRPV1 in the SG is associated with tinnitus. The blast exposure up-regulated TRPV1 in the SG. HPN-07/NAC treatment normalized TRPV1 in the SG, compared to the blast group without treatment.

DETAILED DESCRIPTION

The invention described herein provides a method for promoting or enhancing synaptogenesis and neuritogenesis, comprising administering to a subject suffering from cochlear synaptopathy or vestibular synaptopathy an effective amount of 2,4-disulfonyl α-phenyl tertiary butyl nitrone (2,4-DSPBN, or HPN-07) or a pharmaceutically acceptable salt thereof. Optionally, the 2,4-DSPBN is co-administered with NAC.

Abbreviations

AVCN, anterior ventral cochlear nucleus; AC, auditory cortex; bTBI, blast-induced traumatic brain injury. CtBP2, C-terminal-binding protein 2; DCN, dorsal cochlear nucleus; GluR2/3, glutamate receptor 2/3; HPN-07, 2,4-disulfonyl α-phenyl tertiary butyl nitrone; IC, inferior colliculus; IHC, inner hair cell; mTBI, mild blast-induced traumatic brain injury; NAC, N-acetylcysteine; NF, Neurofilament; OC, the organ of Corti; OHC, outer hair cell; 8-OHdG, 8-hydroxy-2'-deoxyguanosine; psi, pounds per square inch; PVCN, posterior ventral cochlear nucleus; SNHL, sensorineural hearing loss; SG, spiral ganglion; SGN; spiral ganglion neuron; SL, spiral lamina.

2,4-disulfonyl α-phenyl tertiary butyl nitrone (2,4-DSPBN)

2,4-disulfonyl α-phenyl tertiary butyl nitrone is also referred to as 2,4-disulfonyl PBN, 2,4-DSPBN, NXY-059 or HPN-07. It has the following structure:

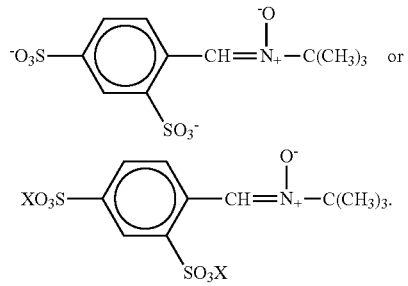

The acid form of the compound has the following structure:

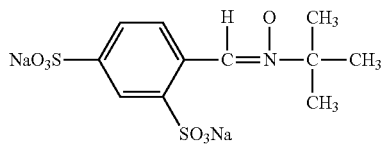

The acid form may be a solid or found in low pH solutions. The ionized salt form of the compound exists at higher pH and may be represented by either of the following structures:

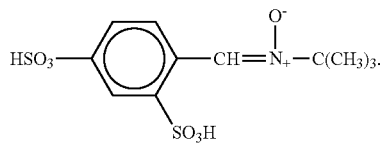

In the salt form, X is a pharmaceutically acceptable cation. Most commonly, this cation is a monovalent material such as sodium, potassium or ammonium, but it can also be a multivalent alone or cation in combination with a pharmaceutically acceptable monovalent anion, for example calcium with a chloride, bromide, iodide, hydroxyl, nitrate, sulfonate, acetate, tartrate, oxalate, succinate, pamoate or the like anion; magnesium with such anions; zinc with such anions or the like. Among these materials, the free acid and the simple sodium, potassium or ammonium salts are most preferred with the calcium and magnesium salts also being preferred but somewhat less so. 2,4-DSPBN is described in detail by U.S. Pat. No. 5,488,145, which is incorporated herein by reference. The salts of 2,4-DSPBN may also be used for promoting or enhancing synaptogenesis and neuritogenesis in a manner similar to the use of 2,4-DSPBN as described herein.

To promote or enhance synaptogenesis and neuritogenesis, 2,4-DSPBN can be administered at a dose of, for example, between about 1 mg/kg to about 500 mg/kg body weight, or between about 5 mg/kg to about 400 mg/kg body weight, or between about 10 mg/kg to about 300 mg/kg body weight, or at about 10 mg/kg body weight, or at about 20 mg/kg body weight, or at about 50 mg/kg body weight, or at about 100 mg/kg body weight, or at about 150 mg/kg body weight, or at about 200 mg/kg body weight, or at about 250 mg/kg body weight, or at about 300 mg/kg body weight.

To promote or enhance synaptogenesis and neuritogenesis in a human subject, 2,4-DSPBN can be administered at a daily dose of, for example, between about 100 mg to about 20,000 mg, or between about 500 mg to about 10,000 mg, or between about 1,000 mg to about 5,000 mg, or at about 100 mg, or at about 200 mg, or at about 500 mg, or at about 1,000 mg, or at about 2,000 mg, or at about 3,000 mg, or at about 5,000 mg, or at about 8,000 mg, or at about 10,000 mg.

The subject can be administered one dose daily, or two doses daily, or three doses daily, or four doses daily, or five doses daily.

2,4-DSPBN can be combined with NAC to promote or enhance synaptogenesis and neuritogenesis. In some embodiments, 2,4-DSPBN and NAC are co-administered as a mixture. In some embodiments, 2,4-DSPBN and NAC are administered sequentially or simultaneously as distinct dosage forms.

In some embodiments, 2,4-DSPBN, and optionally NAC, are administered orally. Other delivery methods including, but not limited to, intravenously, subcutaneously, by inhalation, sublingually, subdermally, intrathecally, or locally within the ear. Further, the active composition may be administered as a nanoparticle or dendrimer formulation. The nanoparticle may be multifunctional and composed of a polymer and paramagnetic iron oxide particles to allow the application of external magnetic forces to aid in the delivery of the drug to the desired target such as the inner ear or the dorsal cochlear nucleus. Additionally, the composition may be formulated with additives known to those skilled in the art to enhance oral absorption and alter bioavailability kinetics.

In place of or in addition to 2,4-DSPBN, other nitrone compounds can also be used to promote or enhance synaptogenesis and neuritogenesis. In some embodiments, the nitrone compound is selected from phenyl butyl nitrone (PBN) and its derivatives. In some embodiments, the nitrone compound is PBN. In some embodiments, the nitrone compound is 4-hydroxy-α-phenyl butyl nitrone (4-OHPBN). In some embodiments, the nitrone compound is 2-sulfonyl-α-phenyl tertiary butyl nitrone (S-PBN).

Therefore, the present application expressly covers the use of any of the aforementioned nitrone compounds in place of or in addition to 2,4-DSPBN in all embodiments disclosed herein. Hence, methods are disclosed in which one or more of phenyl butyl nitrone (PBN), 4-hydroxy-α-phenyl butyl nitrone (4-OHPBN) and 2-sulfonyl-α-phenyl tertiary butyl nitrone (S-PBN) are used in place of or in addition to the 2,4-DSPBN.

Methods for Enhancing Synaptogenesis and/or Neuritogenesis

The invention described herein provides a method for promoting or enhancing synaptogenesis and neuritogenesis, comprising administering to a subject suffering from cochlear synaptopathy or vestibular synaptopathy an effective amount of 2,4-DSPBN or a pharmaceutically acceptable salt thereof. Optionally, the 2,4-DSPBN is co-administered with NAC. Also provided is a method for promoting or enhancing synaptogenesis or neuritogenesis in a subject suffering from cochlear synaptopathy or vestibular synaptopathy, comprising administering to a subject in need thereof an effective amount of 2,4-disulfonyl α-phenyl tertiary butyl nitrone or a pharmaceutically acceptable salt thereof.

Synaptopathy refers to a disease of the brain, spinal cord or peripheral nervous system relating to the dysfunction or loss of synapses. Chronic hearing loss, tinnitus, hyperacusis, presbycusis, or balance disorders are often associated with noise- and age-related cochlear synaptopathy or vestibular synaptopathy that is independent of hair cell loss. Cochlear synaptopathy is described in Kujawa et al., *J Neurosci.*, 29:14077-14085 (2009); Lin et al., *JARO*, 12:605-616 (2011); Sergeyenko et al., *J. Neurosci.*, 33:13686-13694 (2013); Makary et al., *JARO*, 12:711-717 (2011); Viana et al., *Hear Res.*, 327:78-88 (2015); Schaette et al., *Neurosci.*, 31:13452-13457 (2011); Wan et al., *Hear Res.*, 329:1-10 (2015); and Liberman et al., *PLos One*, 11(9):e0162726 (2016), all of which are incorporated herein by reference in their entireties.

In some embodiments, an effective amount of 2,4-DSPBN or its pharmaceutically acceptable salt and optionally NAC are administered to a human patient suffering from a chronic auditory injury or chronic hearing loss, wherein the 2,4-DSPBN or its pharmaceutically acceptable salt and the optional NAC enhance the regeneration of cochlear neurites to a level sufficient to deliver a therapeutic benefit to the subject against the chronic auditory injury or chronic hearing loss. In some embodiments, the 2,4-DSPBN or its pharmaceutically acceptable salt and the optional NAC are administered to a subject who has suffered from an auditory injury or hearing loss for at least one month, at least three months, at least six months, at least one year, or at least two years.

In some embodiments, an effective amount of 2,4-DSPBN or its pharmaceutically acceptable salt and optionally NAC are administered to a human patient suffering from a chronic auditory injury or chronic hearing loss caused by aging, wherein the 2,4-DSPBN or its pharmaceutically acceptable salt and the optional NAC enhance the regeneration of cochlear neurites to a level sufficient to deliver a therapeutic benefit to the subject against the chronic auditory injury or chronic hearing loss caused by aging. In some embodiments, the 2,4-DSPBN or its pharmaceutically acceptable salt and the optional NAC are administered to a subject that is at least 65 years old, or at least 70 years old, or at least 75 years old, or at least 80 years old.

In some embodiments, an effective amount of 2,4-DSPBN or its pharmaceutically acceptable salt and optionally NAC are administered to a human patient suffering from a chronic auditory injury or chronic hearing loss caused by exposure to blast or noise, wherein the 2,4-DSPBN or its pharmaceutically acceptable salt and the optional NAC enhance the regeneration of cochlear neurites to a level sufficient to deliver a therapeutic benefit to the subject against the chronic auditory injury or chronic hearing loss caused by exposure to blast or noise.

In some embodiments, the 2,4-DSPBN or its pharmaceutically acceptable salt and the optional NAC are administered to the subject at least one month, at least three months, at least six months, at least one year, or at least two years, after the exposure to blast or noise. In some embodiments, the 2,4-DSPBN or its pharmaceutically acceptable salt and the optional NAC are not administered to the subject within two weeks, within one week, within four days, within two days, within one day, within 12 hours, or within 4 hours, after the exposure to blast or noise.

In some embodiments, an effective amount of 2,4-DSPBN or its pharmaceutically acceptable salt and optionally NAC are administered to a human patient suffering from a chronic auditory injury or chronic hearing loss caused by infection, wherein the 2,4-DSPBN or its pharmaceutically acceptable salt and the optional NAC enhance the regeneration of cochlear neurites to a level sufficient to deliver a therapeutic benefit to the subject against the chronic auditory injury or chronic hearing loss caused by infection.

In some embodiments, the 2,4-DSPBN or its pharmaceutically acceptable salt and the optional NAC are administered to the subject at least one month, at least three months, at least six months, at least one year, or at least two years, after the infection.

In some embodiments, an effective amount of 2,4-DSPBN or its pharmaceutically acceptable salt and optionally NAC are administered to a human patient suffering from a chronic auditory injury or chronic hearing loss caused by exposure to toxin, wherein the 2,4-DSPBN or its pharmaceutically acceptable salt and the optional NAC enhance the regeneration of cochlear neurites to a level sufficient to deliver a therapeutic benefit to the subject against the chronic auditory injury or chronic hearing loss caused by exposure to toxin.

In some embodiments, the 2,4-DSPBN or its pharmaceutically acceptable salt and the optional NAC are administered to the subject at least one month, at least three months, at least six months, at least one year, or at least two years, after the exposure to toxin.

In some embodiments, an effective amount of 2,4-DSPBN or its pharmaceutically acceptable salt and optionally NAC are administered to a human patient suffering from tinnitus, wherein the 2,4-DSPBN or its pharmaceutically acceptable salt and the optional NAC enhance the regeneration of cochlear neurites to a level sufficient to deliver a therapeutic benefit to the subject against tinnitus. In some embodiments, the 2,4-DSPBN or its pharmaceutically acceptable salt and the optional NAC are administered to a subject who has suffered from tinnitus for at least one month, at least three months, at least six months, at least one year, or at least two years.

In some embodiments, an effective amount of 2,4-DSPBN or its pharmaceutically acceptable salt and optionally NAC are administered to a human patient suffering from hyperacusis, wherein the 2,4-DSPBN or its pharmaceutically acceptable salt and the optional NAC enhance the regeneration of cochlear neurites to a level sufficient to deliver a therapeutic benefit to the subject against hyperacusis. In some embodiments, the 2,4-DSPBN or its pharmaceutically acceptable salt and the optional NAC are administered to a subject who has suffered from hyperacusis for at least one month, at least three months, at least six months, at least one year, or at least two years.

In some embodiments, an effective amount of 2,4-DSPBN or its pharmaceutically acceptable salt and optionally NAC are administered to a human patient suffering from presbycusis, wherein the 2,4-DSPBN or its pharmaceutically acceptable salt and the optional NAC enhance the regeneration of cochlear neurites to a level sufficient to deliver a therapeutic benefit to the subject against presbycusis. In some embodiments, the 2,4-DSPBN or its pharmaceutically acceptable salt and the optional NAC are administered to a subject who has suffered from presbycusis for at least one month, at least three months, at least six months, at least one year, or at least two years.

In some embodiments, an effective amount of 2,4-DSPBN or its pharmaceutically acceptable salt and optionally NAC are administered to a human patient suffering from balance disorder, wherein the 2,4-DSPBN or its pharmaceutically acceptable salt and the optional NAC enhance the regeneration of vestibular neurites to a level sufficient to deliver a therapeutic benefit to the subject against balance disorder. In some embodiments, the 2,4-DSPBN or its pharmaceutically acceptable salt and the optional NAC are administered to a subject who has suffered from balance disorder for at least one month, at least three months, at least six months, at least one year, or at least two years.

In some embodiments, an effective amount of 2,4-DSPBN or its pharmaceutically acceptable salt and optionally NAC are administered to a human patient suffering from Meniere's disease with synapse loss, wherein the 2,4-DSPBN or its pharmaceutically acceptable salt and the optional NAC enhance the regeneration of vestibular neurites to a level sufficient to deliver a therapeutic benefit to the subject against Meniere's disease with synapse loss. In some embodiments, the 2,4-DSPBN or its pharmaceutically acceptable salt and the optional NAC are administered to a subject who has suffered from Meniere's disease with synapse loss for at least one month, at least three months, at least six months, at least one year, or at least two years.

In some embodiments, the administration of 2,4-DSPBN or its pharmaceutically acceptable salt and the optional NAC increases the regeneration rate of cochlear neurites or vestibular neurites by at least 10%, at least 20%, at least 50%, at least 100%, at least 200%, at least 500%, or at least 1000%.

In some embodiments, the administration of 2,4-DSPBN or its pharmaceutically acceptable salt and the optional NAC increases the number of viable nerve connections on inner hair cells by at least 1%, at least 2%, at least 5%, at least 10%, at least 20%, at least 50%, or at least 100%, after one or two or four weeks of treatment, or after more than four weeks of treatment. Methods for measuring increased number of viable nerve connections on inner hair cells are described in Kujawa et al., *J. Neurosci.*, 29:14077-14085 (2009) and Liberman et al., *PLoS One*, 11(9):e0162726 (2016).

In some embodiments, the administration of 2,4-DSPBN or its pharmaceutically acceptable salt and the optional NAC increases the number of synapses (e.g., ribbon synapses) in tonotopic regions in the organ of Corti by at least 1%, at least 2%, at least 5%, at least 10%, at least 20%, at least 50%, or at least 100%, after one or two or four weeks of treatment, or after more than four weeks of treatment. Methods for measuring increased number of synapses in tonotopic regions in the organ of Corti are described in Kujawa et al., *J. Neurosci.*, 29:14077-14085 (2009) and Liberman et al., *PLoS One*, 11(9):e0162726 (2016).

In some embodiments, the administration of 2,4-DSPBN or its pharmaceutically acceptable salt and the optional NAC increases IHC ribbon synapse counts by at least 1%, at least 2%, at least 5%, at least 10%, at least 20%, at least 50%, or at least 100%, after one or two or four weeks of treatment, or after more than four weeks of treatment.

In some embodiments, the administration of 2,4-DSPBN or its pharmaceutically acceptable salt and the optional NAC increases the expression of ARC in the AC, the IC, and/or the DCN by at least 1%, at least 2%, at least 5%, at least 10%, at least 20%, at least 50%, or at least 100%, after one or two or four weeks of treatment, or after more than four weeks of treatment.

In some embodiments, the administration of 2,4-DSPBN or its pharmaceutically acceptable salt and the optional NAC increases the expression of GAP-43 in the AC, the IC, and/or the DCN by at least 1%, at least 2%, at least 5%, at least 10%, at least 20%, at least 50%, or at least 100%, after one or two or four weeks of treatment, or after more than four weeks of treatment.

In some embodiments, the administration of 2,4-DSPBN or its pharmaceutically acceptable salt and the optional NAC decreases the expression of GABAA R$\alpha$1 in the DCN by at least 1%, at least 2%, at least 5%, at least 10%, at least 20%, at least 50%, or at least 100%, after one or two or four weeks of treatment, or after more than four weeks of treatment.

In some embodiments, the administration of 2,4-DSPBN or its pharmaceutically acceptable salt and the optional NAC decreases the expression of GluR2 in the DCN by at least 1%, at least 2%, at least 5%, at least 10%, at least 20%, at least 50%, or at least 100%, after one or two or four weeks of treatment, or after more than four weeks of treatment.

In some embodiments, the administration of 2,4-DSPBN or its pharmaceutically acceptable salt and the optional NAC decreases the expression of TRPV1 in the SG by at least 1%, at least 2%, at least 5%, at least 10%, at least 20%, at least 50%, or at least 100%, after one or two or four weeks of treatment, or after more than four weeks of treatment.

Methods of Reducing Neurodegeneration and/or Accumulation of Tau Proteins in the Auditory System Cochlear neurodegeneration commonly accompanies hair cell loss resulting from aging, ototoxicity, or exposures to intense noise or blast overpressures. Non-transgenic rats exposed to blast overpressures exhibited marked somatic accumulation of neurotoxic variants of the microtubule-associated protein, Tau, in the hippocampus. In another aspect, this disclosure is related to reducing neurodegeneration and pathologic Tau accumulation in the auditory system in response to blast exposure and evaluating the potential therapeutic efficacy of antioxidants on short-circuiting this pathological process. Blast injury induced ribbon synapse loss and retrograde neurodegeneration in the cochlea in untreated animals. An accompanying perikaryal accumulation of neurofilament light chain and pathologic Tau oligomers were observed in neurons from both the peripheral and central auditory system, spanning from the spiral ganglion to the auditory cortex.

Due to its coincident accumulation pattern and well-documented neurotoxicity, the accumulation of pathologic Tau oligomers may actively contribute to blast-induced cochlear neurodegeneration. Therapeutic intervention with a combinatorial regimen of 2,4-disulfonyl α-phenyl tertiary butyl nitrone (HPN-07) and N-acetylcysteine (NAC) significantly reduced both pathologic Tau accumulation and indications of ongoing neurodegeneration in the cochlea and the auditory cortex. This disclosure provides that a combination of HPN-07 and NAC administrated shortly after a blast exposure can serve as a potential therapeutic strategy for preserving auditory function among military personnel or civilians with blast-induced traumatic brain injuries.

Thus, this disclosure described herein provides a method for reducing or slowing down neurodegeneration and/or accumulation of Tau proteins in the auditory system, comprising administering to a subject suffering an effective amount of 2,4-DSPBN or a pharmaceutically acceptable salt thereof. Optionally, the 2,4-DSPBN is co-administered with NAC. In another embodiment, 2,4-DSPBN is co-administered with a Tau aggregation inhibitor. In this disclosure, the terms "Tau" refers to the native monomer form of Tau, or other conformers of Tau, for example, oligomers or aggregates of Tau. The term "Tau" is also used to refer collectively to all types and forms of Tau. Tau proteins perform the function of stabilizing microtubules, which are abundant in nerve cells and are present to a much lesser degree in oligodendrocytes and astrocytes. When Tau proteins become defective and fail to adequately stabilize microtubules, pathologies of the nervous system can develop such as Alzheimer's disease.

In one embodiment, the 2,4-DSPBN or pharmaceutically acceptable salt thereof is administered as a pharmaceutical composition, which further comprises a pharmaceutically acceptable carrier. In another embodiment, the 2,4-DSPBN or pharmaceutically acceptable salt thereof is administered to the subject orally, intravenously, subcutaneously, sublingually, subdermally, intrathecally, by inhalation, or locally within an ear.

In one embodiment, the method further comprises administering one or more compounds selected from the group consisting of N-acetylcysteine, Acetyl-L-Carnitine, glutathione monoethylester, ebselen, D-methionine, carbamathione and Szeto-Schiller peptides and their functional analogs. In another embodiment, the method further comprises administering N-acetylcysteine.

In one embodiment, the neurodegeneration is caused by aging, or exposure to blast or noise, either acute or chronic. In another embodiment, the 2,4-DSPBN or pharmaceutically acceptable salt thereof is administered to the subject at least one month after the exposure to blast or noise. In one embodiment, the 2,4-DSPBN or pharmaceutically acceptable salt thereof is administered to the subject at least one year after the exposure to blast or noise.

In one embodiment, the neurodegeneration is caused by infection. In one embodiment, the 2,4-DSPBN or pharmaceutically acceptable salt thereof is administered to the subject at least one month after the infection. In another embodiment, the 2,4-DSPBN or pharmaceutically acceptable salt thereof is administered to the subject at least one year after the infection.

In one embodiment, the neurodegeneration is caused by exposure to toxin. In another embodiment, the 2,4-DSPBN or pharmaceutically acceptable salt thereof is administered to the subject at least one month after the exposure to toxin. In one embodiment, the 2,4-DSPBN or pharmaceutically acceptable salt thereof is administered to the subject at least one year after the exposure to toxin.

In one embodiment, wherein the administration of the 2,4-DSPBN or pharmaceutically acceptable salt thereof reduces accumulation of Tau proteins in the subject. In one embodiment, the Tau proteins are accumulated in the auditory systems. In some embodiments, the method further comprises administering Tau aggregation inhibitor. The Tau aggregation inhibitor can be covalent or non-covalent inhibitors. Non-limiting examples of Tau aggregation inhibitors include curcumin, molecular tweezers (e.g., CLR01), phthalocyanine tetrasulfonate, oleocanthal, cinnamaldehyde, baicalein, isoprenaline, dopamine, dobutamine, levodopa, levodopa/carbidopa, trimetoquinol, hexoprenaline, methyldopa, and droxidopa.

Methods for Treating Central Nervous System Diseases

The invention described herein also provides a method for promoting or enhancing synaptogenesis and neuritogenesis in the central nervous system of a subject in need thereof, comprising administering to the subject an effective amount of 2,4-DSPBN or a pharmaceutically acceptable salt thereof, wherein the subject suffers from a central nervous system disease or condition selected from Alzheimer's disease, Parkinson's disease, progressive supranuclear palsy, frontotemporal dementia, Pick's disease, Argyrophilic grain dementia, corticobasal degeneration, progressive subcortical gliosis, amyotrophic lateral sclerosis, diffuse neurofibrillary tangles with calcification, chronic traumatic encephalopathy, dementia pugilistica, tangle-only dementia, Down's syndrome, Gerstmann-Straussler-Scheinker disease, Hallervorden-Spatz disease, Creutzfeldt-Jakob disease, multiple system atrophy, Niemann-Pick disease type C, prion protein cerebral amyloid angiopathy, subacute sclerosing panencephalitis, myotonic dystrophy, non-Guanamian motor neuron disease with neurofibrillary tangles, and postencephalitic parkinsonism. Optionally, the 2,4-DSPBN is co-administered with an effective amount of NAC. The 2,4-DSPBN and NAC can be co-administered simultaneously or sequentially. The 2,4-DSPBN and NAC can be co-administered in one composition or in a separately compositions.

A further aspect of the invention relates to a method for treating Alzheimer's disease. In some embodiments, an effective amount of 2,4-DSPBN or its pharmaceutically acceptable salt and optionally NAC are administered to a human patient suffering from Alzheimer's disease, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against Alzheimer's disease.

A further aspect of the invention relates to a method for treating Parkinson's disease. In some embodiments, an effective amount of 2,4-DSPBN or its pharmaceutically acceptable salt and optionally NAC are administered to a human patient suffering from Parkinson's disease, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against Parkinson's disease. In some embodiment, the method reduces accumulation of Tau proteins in the central nervous system of the patient.

A further aspect of the invention relates to a method for treating progressive supranuclear palsy (PSP). In some embodiments, an effective amount of 2,4-DSPBN or its pharmaceutically acceptable salt and optionally NAC are administered to a human patient suffering from PSP, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against PSP.

A further aspect of the invention relates to a method for treating frontotemporal dementia (FTD). In some embodiments, an effective amount of 2,4-DSPBN or its pharmaceutically acceptable salt and optionally NAC are administered to a human patient suffering from FTD, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against FTD.

A further aspect of the invention relates to a method for treating Pick's disease. In some embodiments, an effective amount of 2,4-DSPBN or its pharmaceutically acceptable salt and optionally NAC are administered to a human patient suffering from Pick's disease, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against Pick's disease.

A further aspect of the invention relates to a method for treating Argyrophilic grain dementia (AGD). In some embodiments, an effective amount of 2,4-DSPBN or its pharmaceutically acceptable salt and optionally NAC are administered to a human patient suffering from AGD, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against AGD.

A further aspect of the invention relates to a method for treating corticobasal degeneration (CBD). In some embodiments, an effective amount of 2,4-DSPBN or its pharmaceutically acceptable salt and optionally NAC are administered to a human patient suffering from CBD, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against CBD.

A further aspect of the invention relates to a method for treating progressive subcortical gliosis (PSG). In some embodiments, an effective amount of 2,4-DSPBN or its pharmaceutically acceptable salt and optionally NAC are administered to a human patient suffering from PSG, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against PSG.

A further aspect of the invention relates to a method for treating amyotrophic lateral sclerosis (ALS). In some embodiments, an effective amount of 2,4-DSPBN or its pharmaceutically acceptable salt and optionally NAC are administered to a human patient suffering from ALS, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against ALS.

A further aspect of the invention relates to a method for treating diffuse neurofibrillary tangles with calcification (DNTC). In some embodiments, an effective amount of 2,4-DSPBN or its pharmaceutically acceptable salt and optionally NAC are administered to a human patient suffering from DNTC, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against DNTC.

A further aspect of the invention relates to a method for treating chronic traumatic encephalopathy. In some embodiments, an effective amount of 2,4-DSPBN or its pharmaceutically acceptable salt and optionally NAC are administered to a human patient suffering from chronic traumatic encephalopathy, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against chronic traumatic encephalopathy.

A further aspect of the invention relates to a method for treating dementia pugilistica (DP). In some embodiments, an effective amount of 2,4-DSPBN or its pharmaceutically acceptable salt and optionally NAC are administered to a human patient suffering from DP, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against DP.

A further aspect of the invention relates to a method for treating tangle-only dementia (TOD). In some embodiments, an effective amount of 2,4-DSPBN or its pharmaceutically acceptable salt and optionally NAC are administered to a human patient suffering from TOD, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against TOD.

A further aspect of the invention relates to a method for treating Down's syndrome. In some embodiments, an effective amount of 2,4-DSPBN or its pharmaceutically acceptable salt and optionally NAC are administered to a human patient suffering from Down's syndrome, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against Down's syndrome.

A further aspect of the invention relates to a method for treating Gerstmann-Straussler-Scheinker disease (GSS). In some embodiments, an effective amount of 2,4-DSPBN or its pharmaceutically acceptable salt and optionally NAC are administered to a human patient suffering from GSS, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against GSS.

A further aspect of the invention relates to a method for treating Hallervorden-Spatz disease (HSD). In some embodiments, an effective amount of 2,4-DSPBN or its pharmaceutically acceptable salt and optionally NAC are administered to a human patient suffering from HSD, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against HSD.

A further aspect of the invention relates to a method for treating Creutzfeldt-Jakob disease (CJD). In some embodiments, an effective amount of 2,4-DSPBN or its pharmaceutically acceptable salt and optionally NAC are administered to a human patient suffering from CJD, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against CJD.

A further aspect of the invention relates to a method for treating multiple system atrophy (MSA). In some embodiments, an effective amount of 2,4-DSPBN or its pharmaceutically acceptable salt and optionally NAC are administered to a human patient suffering from MSA, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against MSA.

A further aspect of the invention relates to a method for treating Niemann-Pick disease type C (NPC). In some embodiments, an effective amount of 2,4-DSPBN or its pharmaceutically acceptable salt and optionally NAC are administered to a human patient suffering from NPC, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against NPC.

A further aspect of the invention relates to a method for treating prion protein cerebral amyloid angiopathy (PrP-CAA). In some embodiments, an effective amount of 2,4-DSPBN or its pharmaceutically acceptable salt and optionally NAC are administered to a human patient suffering from PrP-CAA, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against PrP-CAA.

A further aspect of the invention relates to a method for treating subacute sclerosing panencephalitis (SSPE). In some embodiments, an effective amount of 2,4-DSPBN or its pharmaceutically acceptable salt and optionally NAC are administered to a human patient suffering from SSPE, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against SSPE.

A further aspect of the invention relates to a method for treating myotonic dystrophy. In some embodiments, an effective amount of 2,4-DSPBN or its pharmaceutically acceptable salt and optionally NAC are administered to a human patient suffering from myotonic dystrophy, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against myotonic dystrophy.

A further aspect of the invention relates to a method for treating non-Guanamian motor neuron disease with neurofibrillary tangles. In some embodiments, an effective amount of 2,4-DSPBN or its pharmaceutically acceptable salt and optionally NAC are administered to a human patient suffering from non-Guanamian motor neuron disease with neurofibrillary tangles, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against non-Guanamian motor neuron disease with neurofibrillary tangles.

A further aspect of the invention relates to a method for treating postencephalitic parkinsonism (PEP). In some embodiments, an effective amount of 2,4-DSPBN or its pharmaceutically acceptable salt and optionally NAC are administered to a human patient suffering from PEP, wherein the 2,4-DSPBN or its pharmaceutically acceptable salt and the optional NAC enhance neuritogenesis and/or synaptogenesis, and/or reduce the amount of pathologic Tau proteins, in the central nervous system to a level sufficient to deliver a therapeutic benefit to the patient against PEP.

In some embodiment, the method reduces accumulation of Tau proteins in the central nervous system of a patient suffering from a central nervous system disease or condition selected from Alzheimer's disease, Parkinson's disease, progressive supranuclear palsy, frontotemporal dementia, Pick's disease, Argyrophilic grain dementia, corticobasal degeneration, progressive subcortical gliosis, amyotrophic lateral sclerosis, diffuse neurofibrillary tangles with calcification, chronic traumatic encephalopathy, dementia pugilistica, tangle-only dementia, Down's syndrome, Gerstmann-Straussler-Scheinker disease, Hallervorden-Spatz disease, Creutzfeldt-Jakob disease, multiple system atrophy, Niemann-Pick disease type C, prion protein cerebral amyloid angiopathy, subacute sclerosing panencephalitis, myotonic dystrophy, non-Guanamian motor neuron disease with neurofibrillary tangles, and postencephalitic parkinsonism.

In some embodiments, the method slows, stops or reverses neurodegeneration in the central nervous system of a patient suffering from a central nervous system disease or condition selected from Alzheimer's disease, Parkinson's disease, progressive supranuclear palsy, frontotemporal dementia, Pick's disease, Argyrophilic grain dementia, corticobasal degeneration, progressive subcortical gliosis, amyotrophic lateral sclerosis, diffuse neurofibrillary tangles with calcification, chronic traumatic encephalopathy, dementia pugilistica, tangle-only dementia, Down's syndrome, Gerstmann-Straussler-Scheinker disease, Hallervorden-Spatz disease, Creutzfeldt-Jakob disease, multiple system atrophy, Niemann-Pick disease type C, prion protein cerebral amyloid angiopathy, subacute sclerosing panencephalitis, myotonic dystrophy, non-Guanamian motor neuron disease with neurofibrillary tangles, and postencephalitic parkinsonism.

Further Embodiments

Embodiment 1

A method for enhancing synaptogenesis and neuritogenesis in a subject suffering from cochlear synaptopathy or vestibular synaptopathy, comprising administering to said subject in need thereof an effective amount of 2,4-disulfonyl α-phenyl tertiary butyl nitrone (2,4-DSPBN) or a pharmaceutically acceptable salt thereof.

Embodiment 2

The method of Embodiment 1, wherein the 2,4-DSPBN or pharmaceutically acceptable salt thereof is administered as a pharmaceutical composition, which further comprises a pharmaceutically acceptable carrier.

Embodiment 3

The method of Embodiment 1, wherein the 2,4-DSPBN or pharmaceutically acceptable salt thereof is administered to the subject orally, intravenously, subcutaneously, sublingually, subdermally, intrathecally, by inhalation, or locally within an ear.

Embodiment 4

The method of Embodiment 1, which further comprises administering one or more compounds selected from the group consisting of N-acetylcysteine, Acetyl-L-Carnitine, glutathione monoethylester, ebselen, D-methionine, carbamathione and Szeto-Schiller peptides and their functional analogs.

Embodiment 5

The method of Embodiment 1, which further comprises administering N-acetylcysteine.

Embodiment 6

The method of Embodiment 1, wherein the subject suffers from a chronic auditory injury or chronic hearing loss.

Embodiment 7

The method of Embodiment 6, wherein the chronic auditory injury or chronic hearing loss is caused by aging.

Embodiment 8

The method of Embodiment 6, wherein the chronic auditory injury or chronic hearing loss is caused by exposure to blast or noise, either acute or chronic.

Embodiment 9

The method of Embodiment 8, in which the 2,4-DSPBN or pharmaceutically acceptable salt thereof is administered to the subject at least one month after the exposure to blast or noise.

Embodiment 10

The method of Embodiment 8, in which the 2,4-DSPBN or pharmaceutically acceptable salt thereof is administered to the subject at least one year after the exposure to blast or noise.

Embodiment 11

The method of Embodiment 6, wherein the chronic auditory injury or chronic hearing loss is caused by infection.

Embodiment 12

The method of Embodiment 11, in which the 2,4-DSPBN or pharmaceutically acceptable salt thereof is administered to the subject at least one month after the infection.

Embodiment 13

The method of Embodiment 11, in which the 2,4-DSPBN or pharmaceutically acceptable salt thereof is administered to the subject at least one year after the infection.

Embodiment 14

The method of Embodiment 6, wherein the chronic auditory injury or chronic hearing loss is caused by exposure to toxin.

Embodiment 15

The method of Embodiment 14, in which the 2,4-DSPBN or pharmaceutically acceptable salt thereof is administered to the subject at least one month after the exposure to toxin.

Embodiment 16

The method of Embodiment 14, in which the 2,4-DSPBN or pharmaceutically acceptable salt thereof is administered to the subject at least one year after the exposure to toxin.

Embodiment 17

The method of Embodiment 1, wherein the subject also suffers from tinnitus.

Embodiment 18

The method of Embodiment 1, wherein the subject also suffers from hyperacusis.

Embodiment 19

The method of Embodiment 1, wherein the subject also suffers from presbycusis.

Embodiment 20

The method of Embodiment 1, wherein the subject also suffers from balance disorder or Meniere's disease with synapse loss.

Embodiment 21

The method of Embodiment 1, wherein the administration of the 2,4-DSPBN or pharmaceutically acceptable salt thereof enhances regeneration of cochlear neurites or vestibular neurites in the subject.

Embodiment 22

The method of Embodiment 1, wherein the number of viable nerve connections on inner hair cells in the subject is increased.

Embodiment 23

The method of Embodiment 1, wherein the number of synapses in tonotopic regions in the organ of Corti in the subject is increased.

Embodiment 24

The method of Embodiment 1, wherein the subject has not suffered a substantial loss of cochlear hair cells or vestibular hair cells.

Embodiment 25

The method of Embodiment 1, wherein the subject has suffered a substantial loss of cochlear hair cells or vestibular hair cells.

Embodiment 26

A method for enhancing synaptogenesis or neuritogenesis in a subject suffering from cochlear synaptopathy or vestibular synaptopathy, comprising administering to said subject in need thereof an effective amount of 2,4-disulfonyl α-phenyl tertiary butyl nitrone (2,4-DSPBN) or a pharmaceutically acceptable salt thereof.

Embodiment 27

A method for reducing neurodegeneration in a subject, comprising administering to said subject in need thereof an effective amount of 2,4-disulfonyl α-phenyl tertiary butyl nitrone (2,4-DSPBN) or a pharmaceutically acceptable salt thereof.

Embodiment 28

The method of Embodiment 27, wherein the 2,4-DSPBN or pharmaceutically acceptable salt thereof is administered as a pharmaceutical composition, which further comprises a pharmaceutically acceptable carrier.

Embodiment 29

The method of Embodiment 27, wherein the 2,4-DSPBN or pharmaceutically acceptable salt thereof is administered to the subject orally, intravenously, subcutaneously, sublingually, subdermally, intrathecally, by inhalation, or locally within an ear.

Embodiment 30

The method of Embodiment 27, which further comprises administering one or more compounds selected from the group consisting of N-acetylcysteine, Acetyl-L-Carnitine, glutathione monoethylester, ebselen, D-methionine, carbamathione and Szeto-Schiller peptides and their functional analogs.

Embodiment 31

The method of Embodiment 27, which further comprises administering N-acetylcysteine.

Embodiment 32

The method of Embodiment 27, wherein the neurodegeneration is caused by aging.

Embodiment 33

The method of Embodiment 27, wherein the neurodegeneration is caused by exposure to blast or noise, either acute or chronic.

Embodiment 34

The method of Embodiment 33, in which the 2,4-DSPBN or pharmaceutically acceptable salt thereof is administered to the subject at least one month after the exposure to blast or noise.

Embodiment 35

The method of Embodiment 33, in which the 2,4-DSPBN or pharmaceutically acceptable salt thereof is administered to the subject at least one year after the exposure to blast or noise.

Embodiment 36

The method of Embodiment 27, wherein the neurodegeneration is caused by infection.

Embodiment 37

The method of Embodiment 36, in which the 2,4-DSPBN or pharmaceutically acceptable salt thereof is administered to the subject at least one month after the infection.

Embodiment 38

The method of Embodiment 36, in which the 2,4-DSPBN or pharmaceutically acceptable salt thereof is administered to the subject at least one year after the infection.

Embodiment 39

The method of Embodiment 27, wherein the neurodegeneration is caused by exposure to toxin.

Embodiment 40

The method of Embodiment 39, in which the 2,4-DSPBN or pharmaceutically acceptable salt thereof is administered to the subject at least one month after the exposure to toxin.

Embodiment 41

The method of Embodiment 39, in which the 2,4-DSPBN or pharmaceutically acceptable salt thereof is administered to the subject at least one year after the exposure to toxin.

Embodiment 42

The method of Embodiment 27, wherein the administration of the 2,4-DSPBN or pharmaceutically acceptable salt thereof reduces accumulation of Tau proteins in the subject.

Embodiment 43

The method of Embodiment 42, wherein the Tau proteins are accumulated in the auditory systems.

Embodiment 44

The method of Embodiment 27, further comprising administering Tau aggregation inhibitor

Embodiment 45

A method for reducing accumulation of Tau proteins in a subject, comprising administering to said subject in need thereof an effective amount of 2,4-disulfonyl α-phenyl tertiary butyl nitrone (2,4-DSPBN) or a pharmaceutically acceptable salt thereof.

Embodiment 46

The method of Embodiment 45, wherein the 2,4-DSPBN or pharmaceutically acceptable salt thereof is administered as a pharmaceutical composition, which further comprises a pharmaceutically acceptable carrier.

Embodiment 47

The method of Embodiment 45, wherein the 2,4-DSPBN or pharmaceutically acceptable salt thereof is administered to the subject orally, intravenously, subcutaneously, sublingually, subdermally, intrathecally, by inhalation, or locally within an ear.

Embodiment 48

The method of Embodiment 45, which further comprises administering one or more compounds selected from the group consisting of N-acetylcysteine, Acetyl-L-Carnitine, glutathione monoethylester, ebselen, D-methionine, carbamathione and Szeto-Schiller peptides and their functional analogs.

Embodiment 49

The method of Embodiment 45, which further comprises administering N-acetylcysteine.

Embodiment 50

The method of Embodiment 45, wherein the accumulation of Tau proteins is caused by aging.

Embodiment 51

The method of Embodiment 45, wherein the accumulation of Tau proteins is caused by exposure to blast or noise, either acute or chronic.

Embodiment 52

The method of Embodiment 51, in which the 2,4-DSPBN or pharmaceutically acceptable salt thereof is administered to the subject at least one month after the exposure to blast or noise.

Embodiment 53

The method of Embodiment 51, in which the 2,4-DSPBN or pharmaceutically acceptable salt thereof is administered to the subject at least one year after the exposure to blast or noise.

Embodiment 54

The method of Embodiment 45, wherein the accumulation of Tau proteins is caused by infection.

Embodiment 55

The method of Embodiment 54, in which the 2,4-DSPBN or pharmaceutically acceptable salt thereof is administered to the subject at least one month after the infection.

Embodiment 56

The method of Embodiment 54, in which the 2,4-DSPBN or pharmaceutically acceptable salt thereof is administered to the subject at least one year after the infection.

Embodiment 57

The method of Embodiment 45, wherein the accumulation of Tau proteins is caused by exposure to toxin.

Embodiment 58

The method of Embodiment 57, in which the 2,4-DSPBN or pharmaceutically acceptable salt thereof is administered to the subject at least one month after the exposure to toxin.

Embodiment 59

The method of Embodiment 57, in which the 2,4-DSPBN or pharmaceutically acceptable salt thereof is administered to the subject at least one year after the exposure to toxin.

Embodiment 60

The method of Embodiment 45, further comprising administering a Tau aggregation inhibitor.

Embodiment 61

A method for enhancing synaptogenesis and neuritogenesis in a subject suffering from a central nervous system disease or condition, comprising administering to said subject in need thereof an effective amount of 2,4-disulfonyl α-phenyl tertiary butyl nitrone (2,4-DSPBN) or a pharmaceutically acceptable salt thereof.

Embodiment 62

The method of Embodiment 61, wherein the 2,4-DSPBN or pharmaceutically acceptable salt thereof is administered as a pharmaceutical composition, which further comprises a pharmaceutically acceptable carrier.

Embodiment 63

The method of Embodiment 61, wherein the 2,4-DSPBN or pharmaceutically acceptable salt thereof is administered to the subject orally, intravenously, subcutaneously, sublingually, subdermally, intrathecally, by inhalation, or locally within an ear.

Embodiment 64

The method of Embodiment 61, which further comprises administering N-acetylcysteine to said subject.

Embodiment 65

The method of Embodiment 61, wherein the subject suffers from Alzheimer's disease.

Embodiment 66

The method of Embodiment 61, wherein the subject suffers from Parkinson's disease.

Embodiment 67

The method of Embodiment 61, wherein the subject suffers from progressive supranuclear palsy.

Embodiment 68

The method of Embodiment 61, wherein the subject suffers from frontotemporal dementia.

Embodiment 69

The method of Embodiment 61, wherein the subject suffers from Pick's disease.

Embodiment 70

The method of Embodiment 61, wherein the subject suffers from Argyrophilic grain dementia.

Embodiment 71

The method of Embodiment 61, wherein the subject suffers from corticobasal degeneration.

Embodiment 72

The method of Embodiment 61, wherein the subject suffers from progressive subcortical gliosis.

Embodiment 73

The method of Embodiment 61, wherein the subject suffers from amyotrophic lateral sclerosis.

Embodiment 74

The method of Embodiment 61, wherein the subject suffers from diffuse neurofibrillary tangles with calcification.

Embodiment 75

The method of Embodiment 61, wherein the subject suffers from dementia pugilistica.

Embodiment 76

The method of Embodiment 61, wherein the subject suffers from tangle-only dementia.

Embodiment 77

The method of Embodiment 61, wherein the subject suffers from Down's syndrome.

Embodiment 78

The method of Embodiment 61, wherein the subject suffers from Gerstmann-Straussler-Scheinker disease.

Embodiment 79

The method of Embodiment 61, wherein the subject suffers from Hallervorden-Spatz disease.

Embodiment 80

The method of Embodiment 61, wherein the subject suffers from Creutzfeldt-Jakob disease.

Embodiment 81

The method of Embodiment 61, wherein the subject suffers from multiple system atrophy.

Embodiment 82

The method of Embodiment 61, wherein the subject suffers from Niemann-Pick disease type C.

Embodiment 83

The method of Embodiment 61, wherein the subject suffers from prion protein cerebral amyloid angiopathy.

Embodiment 84

The method of Embodiment 61, wherein the subject suffers from subacute sclerosing panencephalitis.

Embodiment 85

The method of Embodiment 61, wherein the subject suffers from myotonic dystrophy.

Embodiment 86

The method of Embodiment 61, wherein the subject suffers from non-Guanamian motor neuron disease with neurofibrillary tangles.

Embodiment 87

The method of Embodiment 61, wherein the subject suffers from postencephalitic parkinsonism.

Embodiment 88

The method of Embodiment 61, wherein the subject suffers from chronic traumatic encephalopathy.

WORKING EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1

In a live animal study, it was discovered that noise-damaged chinchilla treated with 2,4-disulfonyl α-phenyl tertiary butyl nitrone (HPN-07) exhibited significantly greater inner hair cell neurite populations relative to untreated controls and that these animals uniquely exhibited a progressive degree of functional recovery long after the duration of treatment, indicative of ongoing re-innervation of hair cells induced by HPN-07. This led to the potential that HPN-07 possesses pro-neuritogenic properties, in particular among cochlear spiral ganglion neurons (SGNs). HPN-07 has been tested in three in vitro neuritogenic models (cochlear spiral ganglion explants, PC12 cells, and co-cultures of SGN explants with hair cells attached [SGN-HC]). Experimental data from theses analyses have demonstrated that: (1) HPN-07 promoted neuritogenesis in spiral ganglion explants without hair cells; (2) HPN-07 potentiated nerve growth factor (NGF)-induced neuritogenesis in the PC12 cell line; and (3) HPN-07 reversed excitotoxic ribbon synapse loss and increased neurite densities along the base of IHCs in SGN-HC co-cultures following excitoxic trauma induced by kainic acid (KA). HPN-07/NAC treatment among live, blast-exposed rats promoted significantly higher numbers of viable nerve connections on inner hair cells post-blast and, in some tonotopic regions, gave rise to synapse numbers that exceeded those typically observed in naive, undamaged ears.

Figure 1:
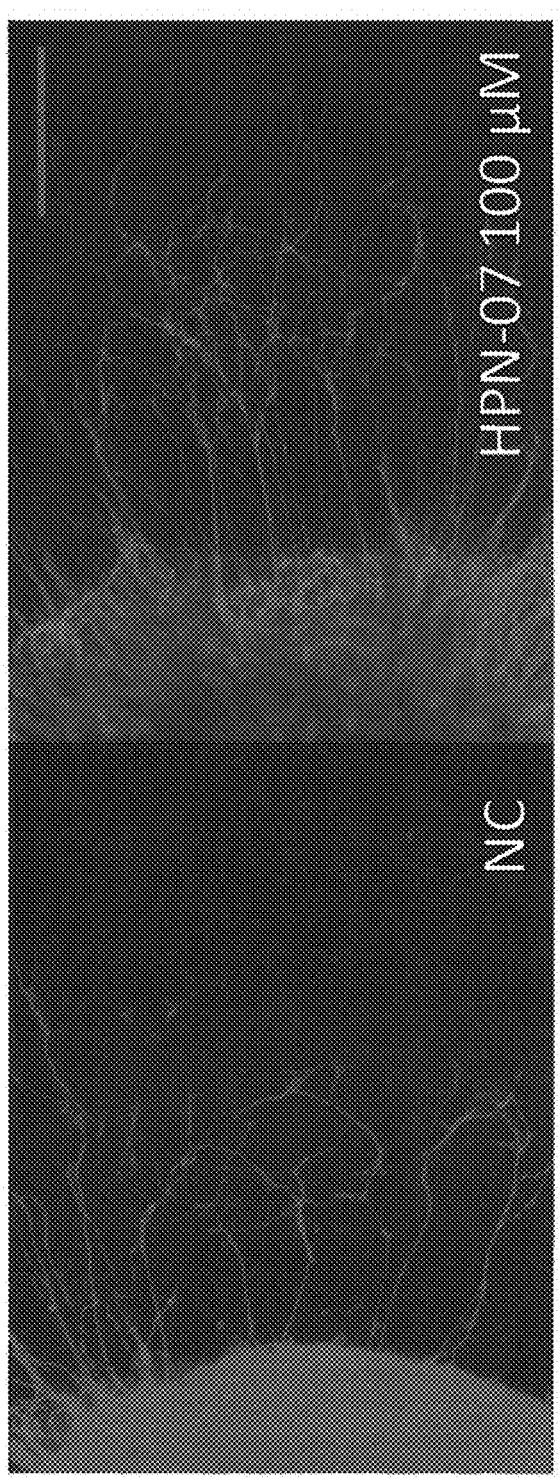
FIG. 1 shows that HPN-07 induced a neuritogenic response in murine spiral ganglion (SG) tissue explants in vitro. HPN-07 induced marked neurite outgrowth relative to untreated controls cultured in the same organotypic culture medium (NC, normal control). Both the number of neurites radiating out from each SG explant and the corresponding length of each of these extensions increased in the presence of HPN-07.

As shown in FIG. 1, HPN-07 induced a neuritogenic response in murine spiral ganglion tissue explants in vitro. HPN-07 induced marked neurite outgrowth relative to untreated controls cultured in the same organotypic culture medium (NC, normal control). Both the number of neurites radiating out from each SGN explant and the corresponding length of each of these extensions increased in the presence of HPN-07. In contrast to PBN which requires a concentration of 10 mM for inducing neuritogenesis in PC12 cells, a concentration of 100 µM HPN-07 was sufficient to induce a neuritogenic response in organotypic cultures of mouse spiral ganglion neurons.

Figure 2:
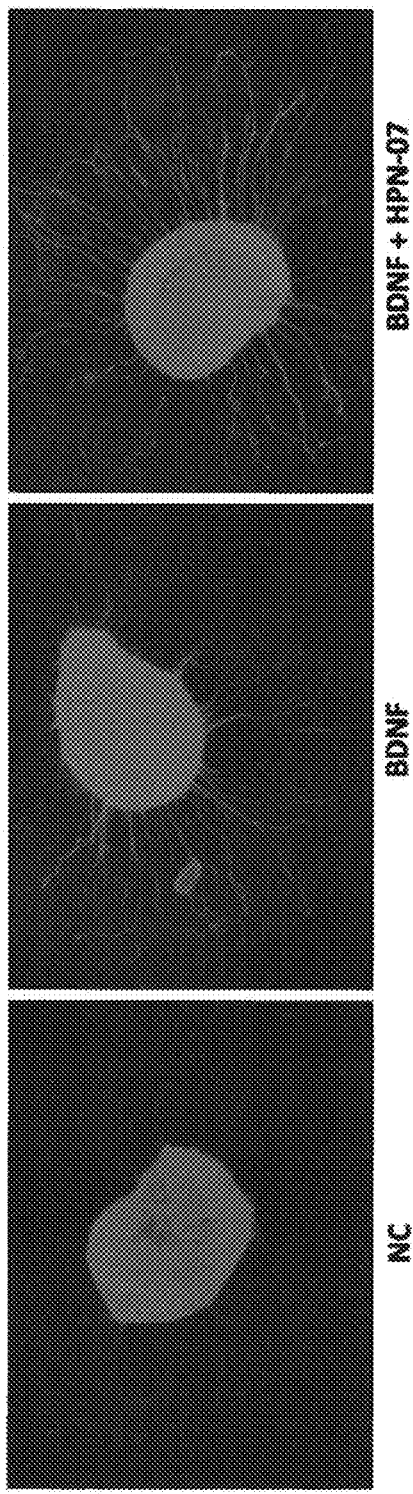
FIG. 2 shows that HPN-07 potentiated neuritogenesis induced by the canonical cochlear neuritogenic growth factor, Brain-derived neurotrophic factor (BDNF). Murine spiral ganglion explants were cultured in serum-free medium with or without BDNF (10 ng/mL) or BDNF (10 ng/mL)+HPN-07 (0.1 µM) for 48 hours and then fixed and immunolabeled with a β-Tubulin to visualize neurites.

HPN-07 potentiated neuritogenesis induced by the canonical cochlear neuritogenic growth factor, brain-derived neurotrophic factor (BDNF), as shown in FIG. 2. Murine spiral ganglion neuron explants were cultured in serum-free medium with or without BDNF (10 ng/mL) or BDNF (10 ng/mL)+HPN-07 (0.1 µM) for 48 hours and then fixed and immunolabeled with a β-Tubulin antibody to visualize neurites.

Figure 3:
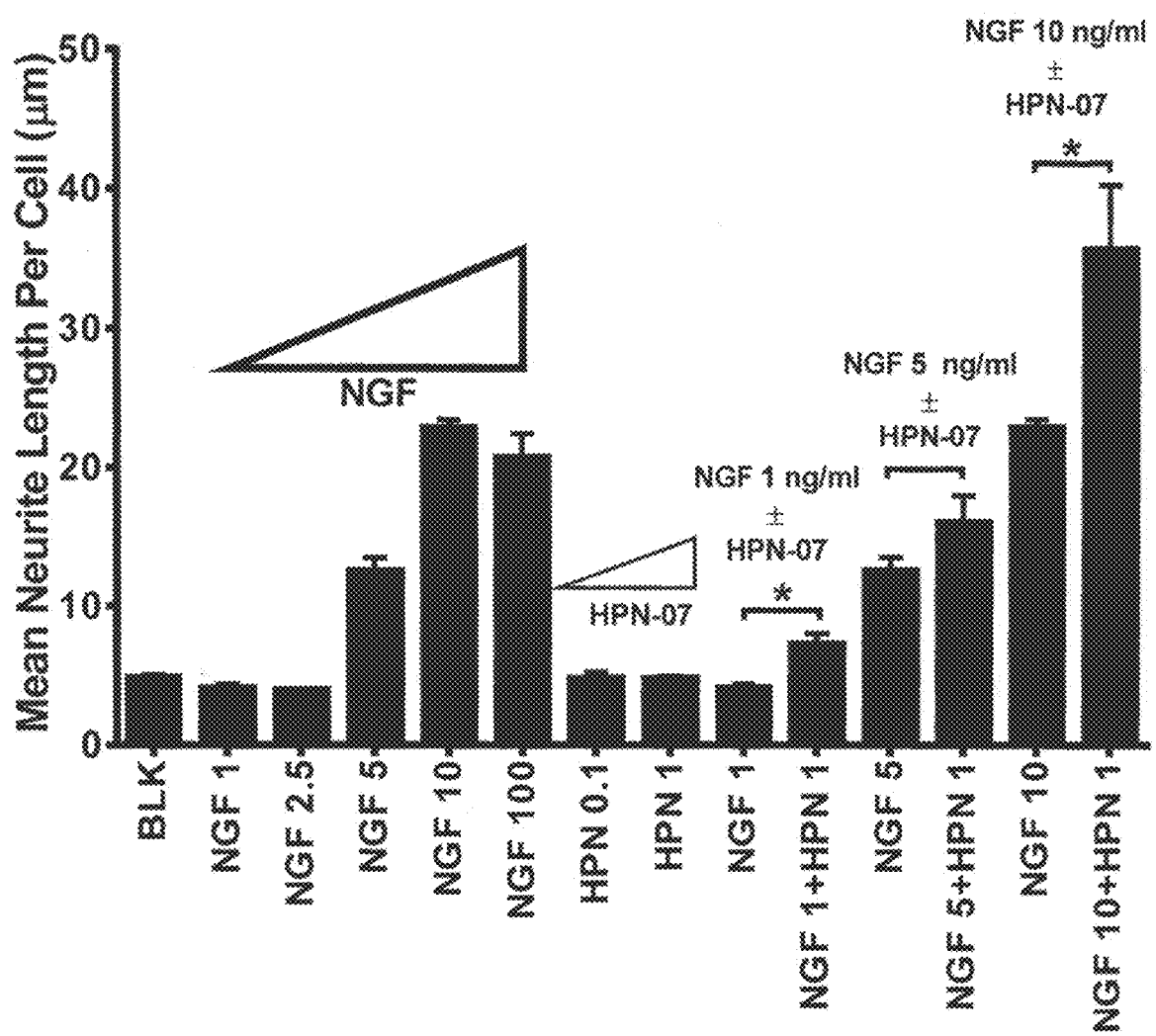
FIG. 3 shows mean neurite length per cell in the PC12 cell line. Combinatorial treatment with HPN-07 and escalating doses of NGF revealed that HPN-07 significantly enhanced NGF-mediated neurite elongation (i.e. increases in mean neurite length) in the neuronal PC12 cell line.

HPN-07 also potentiated NGF-induced neurite elongation in the PC12 cell line, as shown in FIG. 3. Nerve growth factor (NGF) treatment induced neurite elongation in a dose-dependent manner in PC12 cells, a standard neuronal model for neuritogenesis studies. This NGF-induced neuritogenic response was apparently saturable at concentrations at and above 10 ng/mL in this context. However, while treatment with HPN-07 alone did not increase neurite length at low concentrations in this system, combinatorial treatment with 1 µM HPN-07 and escalating doses of NGF (1, 5 or 10 ng/mL) revealed that HPN-07 enhances (at 1 and 5 ng/mL NGF), and perhaps even synergizes (at 10 ng/mL NGF), with NGF to promote neuritogenesis. At concentrations of 10 ng/mL NGF and 1 µM HPN-07, mean neurite lengths markedly surpassed the maximum lengths achieved in the saturable NGF dose-escalation series (cells were treated for 6 days).

Figure 4:
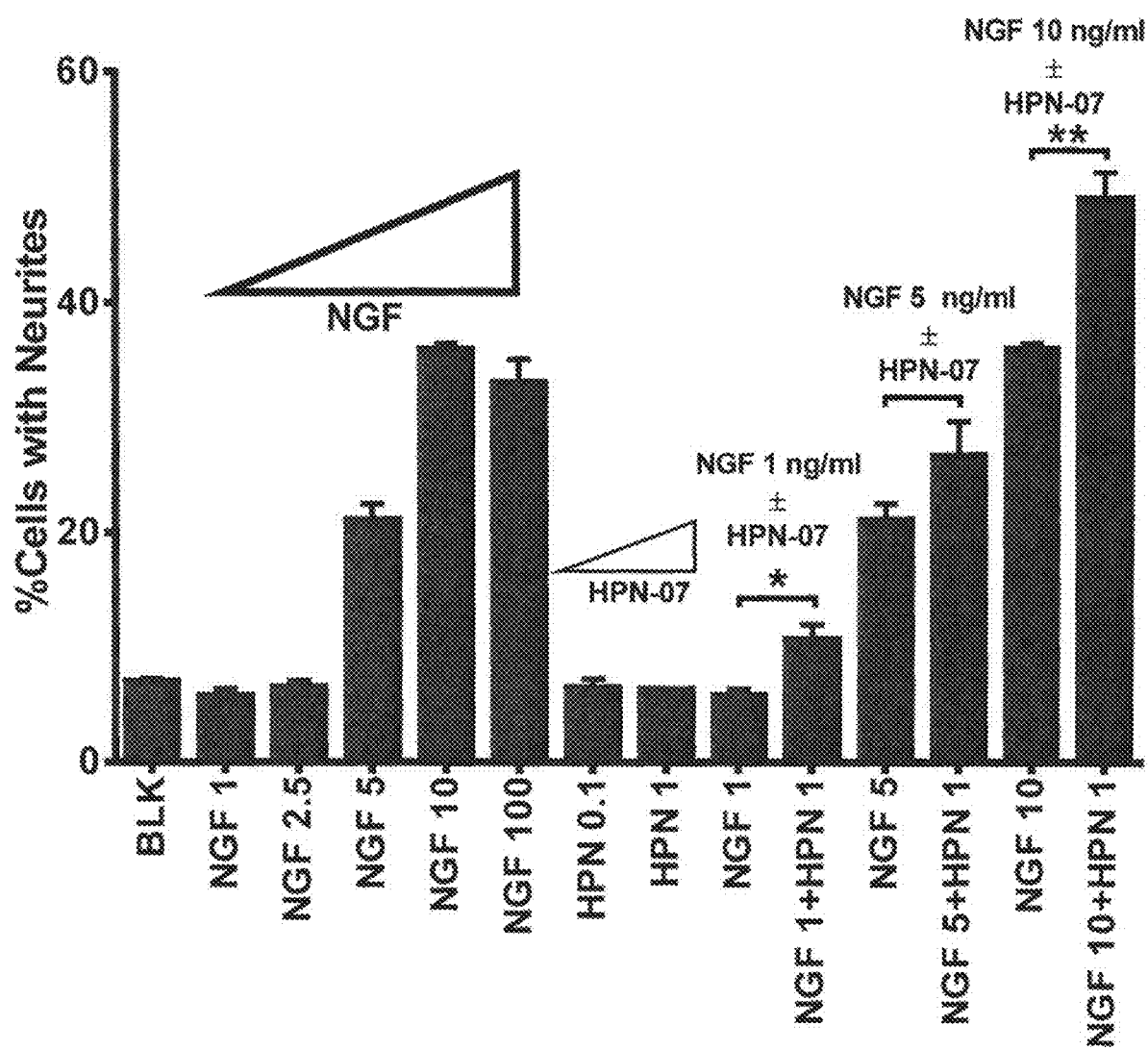
FIG. 4 shows the percentage of PC12 cells that exhibit significant neurite outgrowth. Combinatorial treatment with HPN-07 and escalating doses of NGF revealed that HPN-07 significantly enhanced NGF-induced neuritogenesis in neuronal PC12 cells, as evidenced by significant increases in the percentage of cells bearing neurites following treatment.

FIG. 4 depicts the percentage of PC12 cells with significant neurite outgrowth. The pattern observed here is similar to that observed for treatment-induced increases in average neurite length. Taken together, these evaluations support the interpretation that HPN-07 acts in concert with NGF to promote both de novo neurite outgrowth and changes in the stability or assembly kinetics of neurites in such a manner as to support increases in mean neurite length, both of which are desirable features for re-innervation of IHCs. As growth factors are constitutively expressed in the mammalian cochlea and are often upregulated following an auditory trauma, this therapeutic attribute could have significant clinical impact for restoring auditory function.

Figure 5:
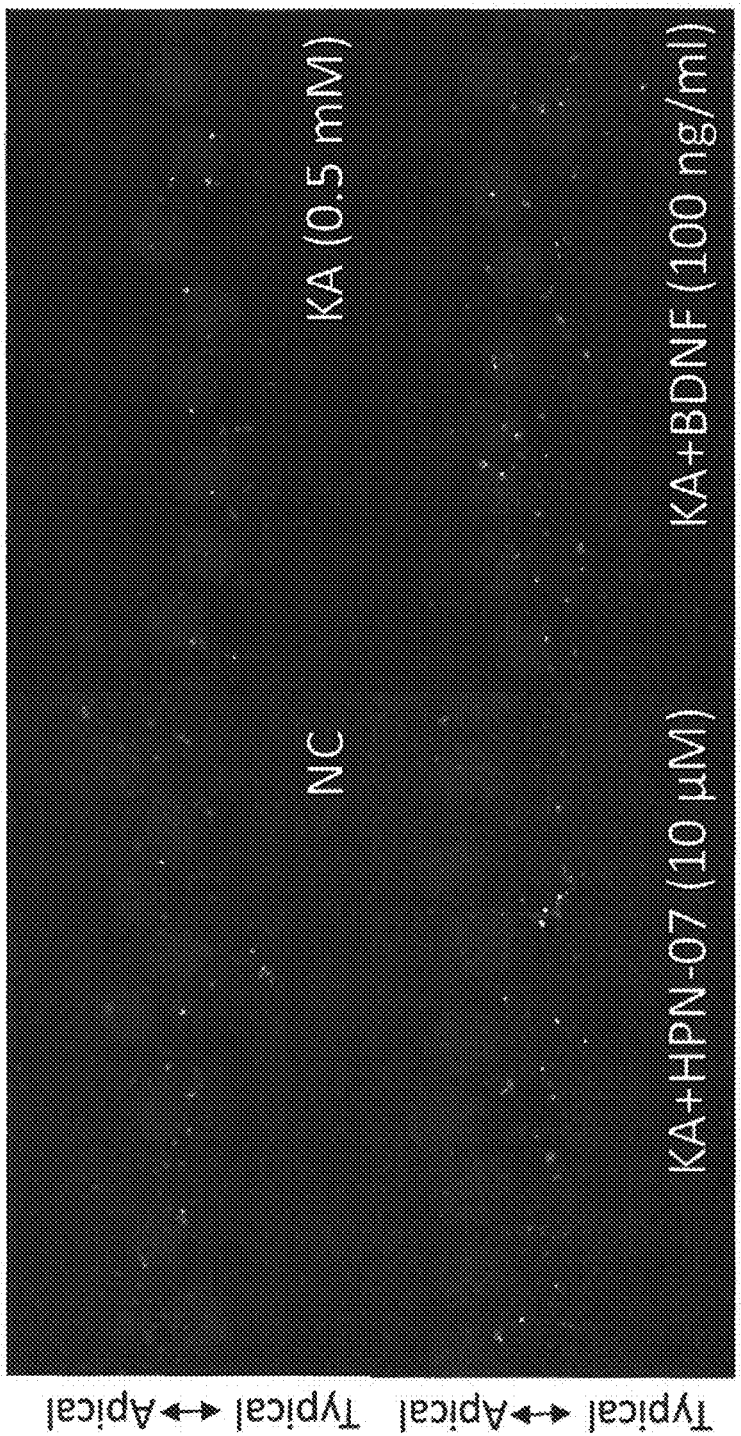
FIG. 5 shows reversal of kainic acid (KA)-induced excitotoxic loss of inner hair cell (IHC) ribbon synapse integrity by HPN-07.

Further, HPN-07 reversed kainic acid (KA)-induced excitotoxic loss of IHC ribbon synapse integrity, as shown in FIG. 5. The previous findings were applied to a murine SGN-IHC co-culture model of excitotoxic trauma. In IHCs of undamaged co-cultures of auditory sensory epithelia (organs of Corti, OC) and associated spiral ganglion neurons (NC), most of the pre-synaptic C-terminal binding protein 2 (CtBP2)-immunoreactive puncta (small red dots) are located in a "typical," cytoarchitectural position, located along the basal surface of the cell, below or surrounding the IHC nucleus (large red spheres). A marked shift from this typical CtBP2 basal immunoreactivity pattern to a more apical distribution pattern occurred after exposure to the excitotoxic glutamate analog, kainic acid (KA). This aberrant trend was correlated with a gross loss of co-immunolabeling for the post-synaptic density marker, PSD-95, indicating that the apical shifts in CtBP2-labeled punctae were likely attributable to KA-induced loss of ribbon synapse integrity and dissociation of PSDs, which anchored the active synapse along the basal plane. Post-excitotoxic treatment with HPN-07 at a concentration shown to induce neuritogenesis in SG explants (10 µM) reversed this pathologic shift and repopulated the IHCs with basal PSDs that co-labeled with CtBP2 in a manner similar to that achieved by the canonical neurotrophic growth factor BDNF. The ability of HPN-07 to restore the structural integrity of ribbon synapses among IHCs following an excitotoxic trauma in this co-culture model is consistent with HPN-07 acting to promote synaptogenesis (i.e., re-innervation) in this context.

Figure 6:
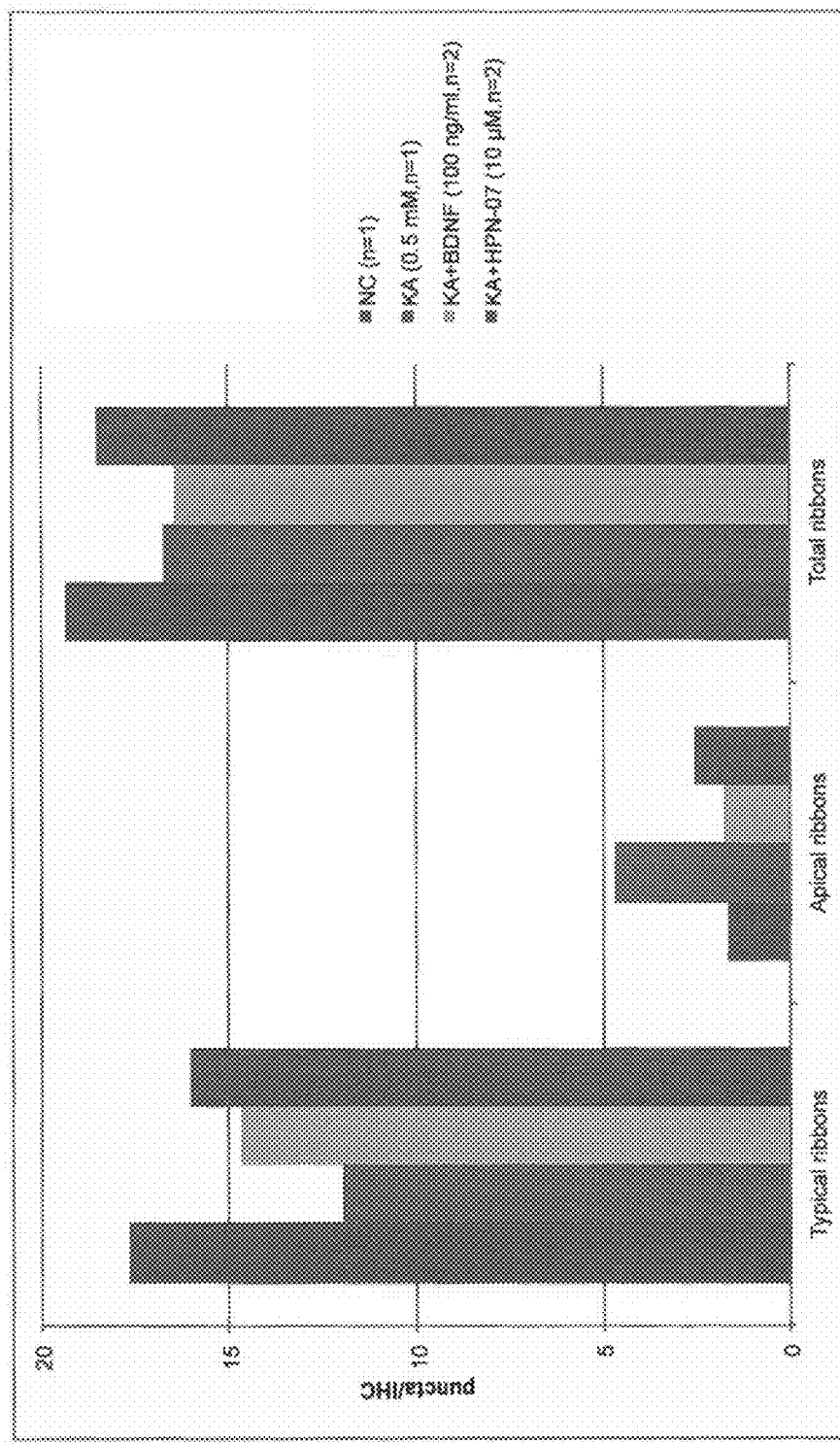
FIG. 6 summarizes a quantitative evaluation from a targeted comparison of the number and spatial distribution of ribbons among IHCs from untreated, BDNF-treated, or HPN-07-treated cochlear explants following excitotoxic exposure to KA.

FIG. 6 summarizes a quantitative evaluation from a targeted comparison of the number and spatial distribution of ribbons among IHCs from untreated, BDNF-treated, or HPN-07-treated explants following excitotoxic exposure to KA. Following KA exposure, untreated cultures exhibited a shift of pre-synaptic densities from "typical" (below nucleus) to "apical" (above nucleus) distributions. Both BDNF and HPN-07 reversed this pathologic change, underscoring their utility for re-innervating IHCs in this context. However, HPN-07 treatment resulted in a greater number of total ribbons, more closely approximately that observed in undamaged tissue. Each data point represents a composite of approximately ten independent measurements.

Figure 7:
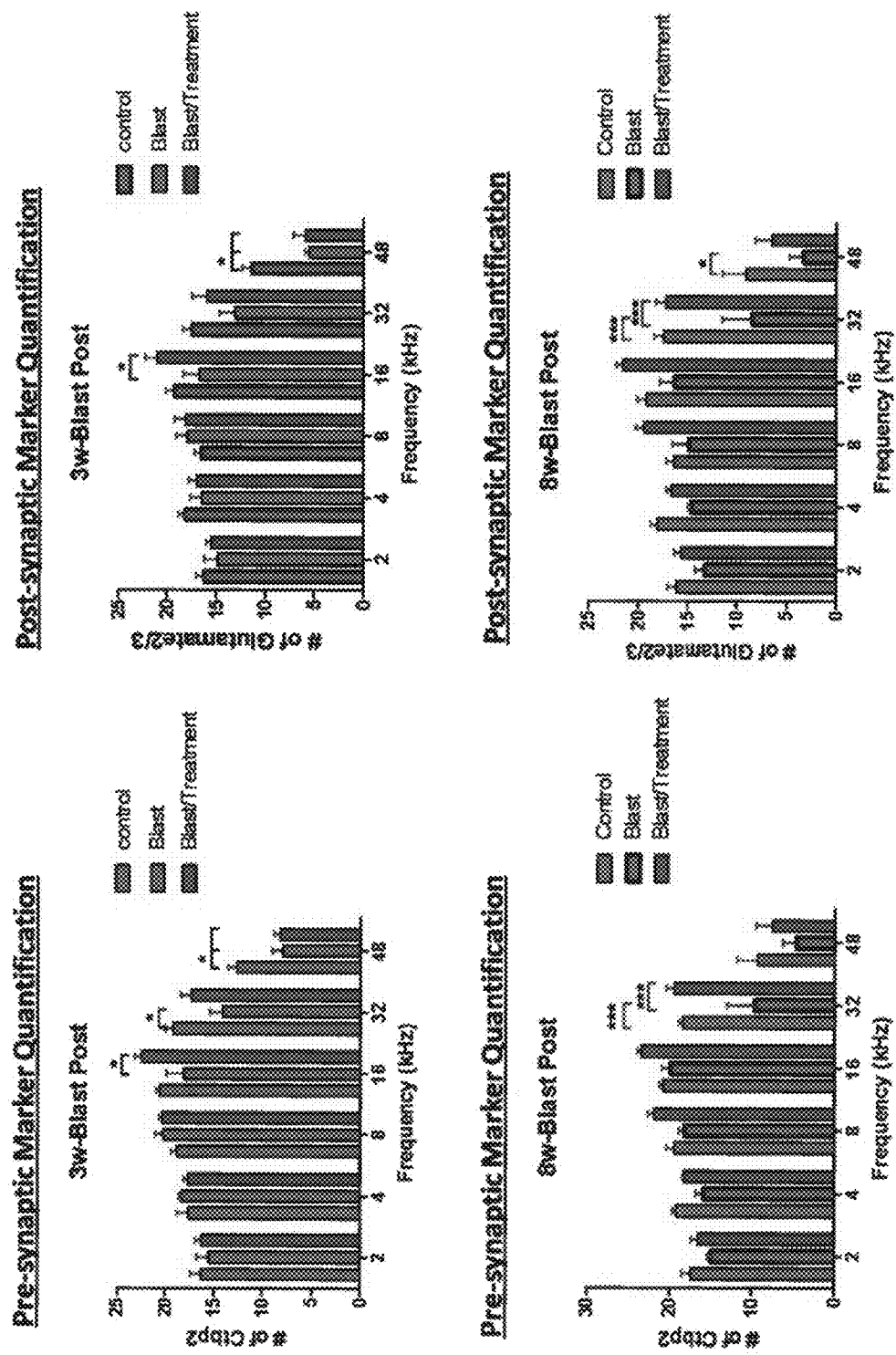
FIG. 7 shows pre-synaptic marker quantification (C-terminal binding protein 2, CtBP2) and post-synaptic marker quantification (GluR2/3). In the upper panel, rats were exposed to three successive open-field blasts at 14 psi repeated at 1.5-minute intervals, and then injected (i.p.) with HPN-07/NAC one hour after the final blast and then twice-daily for the next 48 hours. In the lower panel, rats were exposed to a single, 8 psi blast within a shock-tube and then injected (i.p.) with HPN-07/NAC one hour after the final blast and then twice-daily for the next 48 hours.

HPN-07/NAC treatment among live, blast-exposed rats promoted significantly higher numbers of viable nerve connections on inner hair cells post-blast and, in some tonotopic regions, trended towards synapse numbers that exceeded those typically observed in naive, undamaged ears, as shown in FIG. 7. In the upper panel, rats were exposed to three successive open-field blasts at 14 psi repeated at 1.5-minute intervals. Animals were then injected (i.p.) with HPN-07/NAC one hour after the final blast and then twice-daily for the next 48 hours. Animals were euthanized three weeks later, and their cochlear tissues were fixed, harvested, micro-dissected, and co-immunolabeled with antibodies that target the ribbon synapse within the inner hair cell (CtBP2) and the post-synaptic density (GluR2/3) at the synaptic interface with its associated neurite. The presence of both markers is indicative of a viable synaptic junction. Significant treatment effects on synaptic densities were observed at the 16 kHz tonotopic region of the organ of Corti, with a trend toward supernumerary synapse numbers (relative to naïve controls) at this position. In the lower panel, rats were exposed to a single, 8 psi blast within a shock-tube. Animals were then injected (i.p.) with HPN-07/NAC one hour after the final blast and then twice-daily for the next 48 hours. Animals were euthanized eight weeks later, and their cochlear tissues were fixed, harvested, micro-dissected, and co-immunolabeled with antibodies against CtBP2 and GluR2/3 as described above. Significant treatment effects were observed at the 32 kHz tonotopic region of the organ of Corti in these rats, with trends toward supernumerary synapse numbers (relative to naive controls) at the 8 and 16 kHz regions.

Example 2

Animals, Blast Exposure, and Drug Administration

The tissue samples used in this study were collected as previously described (Ewert et al., *Hear. Res.*, 285, 29-39 (2012)) except for the cochlear tissue samples used for ribbon synapse evaluations. Blast exposure, administration of antioxidants and measurement of auditory brainstem responses were described in detail in our previous report (Ewert et al., *Hear. Res.*, 285, 29-39 (2012)). All procedures regarding the use and handling of animals were reviewed and approved by the Oklahoma Medical Research Foundation (OMRF) Institutional Animal Care and Use Committee and the U.S. Department of the Navy Office of Naval Research.

Male Long-Evans pigmented rats with body weights between 360 and 400 g (Harlan Laboratories, Indianapolis, Ind.) were used in this study. The animals were housed in the animal facility of OMRF. Each rat was exposed to three successive 14 pounds per square inch (psi) blasts repeated at 1.5-minute intervals. The blast protocol induced significant hearing loss and a low incidence of tympanic membrane rupture (Ewert et al., *Hear. Res.*, 285, 29-39 (2012)). Ears having ruptured tympanic membranes were excluded from the study. Auditory brainstem responses (ABR) thresholds and distortion product of otoacoustic emissions (DPOAE) levels were obtained prior to blast exposure and at the 24-hour (24H), 7-day (7D), and 21-day (21D) post-exposure sampling intervals and were reported in our previous publications. Du et al., *PLoS One*, e80138 (2013); Ewert et al., *Hear. Res.*, 285, 29-39 (2012).

A 20% solution of NAC was purchased from Hospira, Inc. (Lake Forest, Ill.), and HPN-07 was synthesized and provided by APAC Pharmaceuticals, LLC (Columbia, Md.). Animals in the blast-exposed, antioxidant-treated group (B/T) were intraperitoneally (i.p.) injected with a combination of 300 mg/kg of NAC plus 300 mg/kg of HPN-07 dissolved in physiological saline solution (5 mL/kg). Drug administration was initiated one hour after blast exposure and then continued twice a day for the following two days. Animals in the untreated, blast-exposed group (B) were injected i.p. with an equal volume of saline according to the same schedule as the treated group. An additional eleven rats that were neither exposed to blast nor received drug treatments were used as normal controls (NC).

Collection of Cochlear Tissues for Ribbon Synapse Evaluations

Animals were decapitated under deep anesthesia with ketamine and xylazine one or three weeks after blast exposure. Cochleae were quickly dissected away from the temporal bones and placed in cold PBS. Round and oval windows were opened, and the bone of apical turn was removed. Four percent formaldehyde solution in PBS was perfused into the cochlea for tissue fixation. The cochleae were placed in the same fixative for an additional 10 min at 4° C. After fixation, cochleae were further dissected in PBS and then blocked in PBS containing 1% Triton X-100 and 5% normal horse serum for one hour before immunolabeling with a combination of rabbit anti-GluR2/3 antibody (Millipore Bioscience, catalog # AB1506, 1:100) and mouse anti-C-terminal binding protein antibody (CtBP2, BD Transduction Laboratories, catalog #612044, 1:200) for 20 hours at 37° C. The tissues were rinsed with PBS and incubated with Alexa Fluor488 chicken anti-rabbit (1:1000, Life Technologies, Co., Grand Island, N.Y.) for one hour at 37° C. The tissues were rinsed with PBS and incubated with Alexa Fluor488 goat anti-chicken antibody (1:1000, Life Technologies, Co., Grand Island, N.Y.) and Alexa Fluor568 goat anti mouse antibody (1:1000, Life Technologies, Co., Grand Island, N.Y.) for one hour at 37° C. (Furman et al., 2013). The tissues were counterstained with DAPI (4',6-diamidino-2-phenylindole) for 10 min at room temperature to label nuclei and then mounted on slides with anti-fade medium.

The whole cochlea was photographed with an epifluorescence microscope. Cochlear length was measured and frequency was computed using a custom plug-in ImageJ software (http://www.masseyeandear.org/research/ent/eaton-peabody/epl-histologyresources/). Six frequency locations of cochlea, 2, 4, 8, 16, 32, 48 kHz, were selected for image collection as confocal z-stacks. Images were acquired in a 1024×1024 pixel frame with 0.5 µm steps in the z plane, using a Zeiss LSM-710 confocal microscope (Carl Zeiss Microimaging, LLC, NY). From an endolymphatic surface view of the organ of Corti, each stack contained six to nine IHCs with entire set of ribbon synapses. synaptic points. 3-D morphometry was processed by using Amira 3D software (FEI, Burlington, Mass.). All quantitative analyses were performed with raw image stacks. The presynaptic ribbons (red channel) and postsynaptic densities (green channel) were identified by segmentation; quantified and tracked in the z-dimension to avoid superpositional ambiguity or overestimations in each stack, and divided by the total number of IHCs in the microscopic field according to a previously published method (Kujawa and Liberman, *J. Neurosci.*, 29, 14077-14085 (2009)).

Collection and Sectioning of Cochlear and Brain Tissues

Animals used for cochlea and brain sectioning in each experimental group (6-8 rats/time point) were euthanized and intracardially perfused with saline followed by 4% paraformaldehyde in 0.1 M phosphate-buffered saline (PBS, pH 7.2) at either 24 hours, 7 days, or 21 days post-blast. Cochleae, brains, and brainstems were removed and post-fixed in the same fixative (overnight for the cochleae and one week for the brain tissues) washed in PBS, and stored in PBS at 4° C. The fixed cochleae were washed with PBS and then decalcified for two weeks in 10% EDTA with solution changes two times each week. Cochleae were dehydrated, embedded in paraffin, and sectioned in a paramodiolar plane at a thickness of 6 µm, and every 10th section was mounted on a slide (total of 10 slides per cochlea). The mounted sections were then processed for immunohistochemical analyses.

The brain and brainstem from each animal was cryoprotected in 30% sucrose in PBS at 4° C. until the tissue settled to the bottom of the container, at which time they were embedded in Tissue-Tek (Sakura Finetek USA Inc. Torrance, Calif.) and serially sectioned in a coronal plane with a Thermo Cryotome (Thermo Fisher Scientific, Inc. Waltham, Mass.) at 18-20 µm. One section out of every ten from each brain and brainstem was mounted onto a gelatin pre-coated slide (total of 10 slides for each brainstem and 20 slides for each brain). The distance between two adjacent sections on each slide was about 200 µm. The sections were then processed for immunohistochemical analyses.

Quantification of Spiral Ganglion Neurons and Neurites in the Cochlea

Two biomarkers, the neurofilament (NF) light (68 kDa, NF-68) and heavy (200 kDa, NF-200) subunits, were used to examine cochlear neurodegeneration in blast-exposed rats. Cochlear sections were de-paraffinized in xylene and re-hydrated in serial concentrations of ethanol and distilled water. These sections were then washed with PBS, blocked in 1% bovine serum albumin (fraction V) and either 1% normal horse serum or 1% normal goat serum in PBS, and permeabilized in 0.2% Triton X-100 in PBS (PBS/T). Blocked and permeabilized sections were then incubated with either mouse anti-neurofilament 68 (1:200, clone NR4, Sigma, St. Louis, Mo., catalog# N5139) or chicken anti-neurofilament 200 (1:1000, EMD Millipore, Billerica, Mass., catalog# AB5539) overnight at room temperature. After washing with PBS/T, either biotinylated goat anti-chicken IgG or horse anti-mouse IgG (1:200, Vector Laboratories, Inc. Burlingame, Calif.) was applied to the slides for one hour at room temperature, and Vectastain ABC and DAB kits (Vector Laboratories, Inc. Burlingame, Calif.) were used for the immunolabeling visualization. Immunopositive cells exhibited a brown reaction product at the sites of the target epitopes. Methyl green was used for nuclear counter-staining. Negative controls were conducted by omitting the primary antibodies. Toluidine blue was used to stain neurons in the SG of normal controls and blast-exposed rats to examine average neuron size and injury-induced attrition.

Tau Immunohistochemical Staining in the Brain and the Cochlea

The same immunohistochemical staining protocol as described above was used for Tau staining. Tissue sections were incubated overnight with either mouse anti-Tau-1 antibody, which recognizes all known electrophoretic species of Tau protein lacking phosphorylation at serine sites 195, 198, 199, and 202 (1:200, clone PC1C6, EMD Millipore, Billerica, Mass., catalog # MAB3420), mouse anti-Tau 46, which recognizes all six native isoforms of Tau (1:100, Sigma, St. Louis, Mo., catalog # T9450), mouse anti-phospho(Ser202/Thr205)-Tau antibody (1:250, clone AT8, Thermo Scientific, Waltham, Mass., catalog # MN1020), or rabbit anti-oligomeric Tau antibody (T22 serum, 1:300, a kind gift from Dr. Rakez Kayed at the University of Texas Medical Branch, Galveston, Tex., Hawkins et al. 2013).

Oligomeric Tau/NF-68 and Myosin VIIa/NF-200 Dual-Labeling Analyses in the Cochlea after Blast Exposure Cochlear sections were incubated with either T22 antibody (1:200) and anti-neurofilament 68 (1:200) or NF-200 (1:1000) and rabbit anti-myosin VIIa (1:1000. Proteus Biosciences Inc., Ramona, Calif., catalog #25-6790) overnight at room temperature. After washing with PBS, the sections were incubated with appropriate Alexa Fluor® 488, 568 or 647 secondary antibodies (1:1000, Life Technologies, Co., Grand Island, N.Y.) for two hours at room temperature followed by DAPI labeling and mounting in anti-fade medium. Images were collected with a Zeiss LSM-710 confocal microscope.

Oxidative Stress Biomarker Analysis in the Cochlea after Blast Exposure 8-hydroxy-2'-deoxyguanosine (8-OHdG) levels, a product of DNA oxidation, were examined as a biomarker for evaluating changes in oxidative stress-induced damage in cochlear neurons among blast-exposed animals. The same immunohistochemical staining protocol described above was used for 8-OHdG immunostaining. Tissue sections were incubated overnight with rabbit anti-8-OHdG antibody (1:100, Bioss antibodies, Woburn, Mass., catalog # bs-1278R).

Quantification of Biomarker Immunostaining

Images were collected with a BX51 Olympus microscope (SG and brain) or Zeiss Axiovert 200m Inverted Fluorescent Microscope (nerve fibers in the spiral lamina (SL) and in the organ of Corti (OC). In the cochlea, images (SG, nerve fibers in the SL and the Inner HC (IHC) area) were collected from the basal and middle turns of all sections on each slide. The number of NF-68-, NF-200-, or 8-OHdG-positive neurons was quantified using ImageJ software (National Institutes of Health). The percentage of NF-68-positive, NF-200-positive (weakly-stained or strongly-stained), and 8-OHdG-positive neurons in the SG (positive stained/total number of neurons×100%) was calculated and statistically analyzed. The density of NF-200-, Tau46-, AT8- or T22-positive nerve fibers (number of nerve fibers/mm2) in the SL was also estimated using ImageJ software (Jensen et al., *PLoS One* 10. doi:10.1371/journal.pone.0125160 (2015)). To examine SGN loss 21 days after blast exposure, the size of SGs in the middle and basal turns of NC and blast-exposed rats was measured, and relative densities of SGNs (number of toluidine blue-stained neurons/mm2) were calculated and statistically analyzed. To examine SGN size 21-days after blast exposure, the maximal diameter of toluidine blue-stained SGNs in the cochlea of NC and blast-exposed rats was measured (Bichler, 1984). Images were collected from the apical, basal and middle turns of cochlear sections, and the average maximal diameters of SGNs (µm) were calculated and statistically analyzed. Only toluidine blue-positive neurons were included in the analyses.

In the dorsal cochlear nucleus (DCN), images were collected from the medial third (medial), the middle third (middle) and the lateral third (lateral) sections. In the inferior colliculus (IC), images were collected from the central nucleus of the IC (CIC). In the AC, images were collected from all layers (two images to cover all layers on one section). A modified two-dimensional quantification method was employed to count positive immunostained cells in these nuclei or regions (Du et al., PLoS One, e80138 (2013)). The total number of positive cells within each image was quantified using ImageJ software, and the density of each class of Tau-positive cells (number of positive cells/mm2) was calculated and statistically analyzed. Only dark brown-stained cells were counted. The cell and neurite counting was conducted by a technician who was unaware of the identity of the samples on each slide.

Statistical Analyses

One way or two way ANOVA (SPSS 14.0 for windows) and a post hoc test (Tukey HSD) were used to determine if there were statistically significant differences among the three groups (NC, B and B/T) at each sampling interval. A p-value of less than 0.05 was considered to be statistically significant in these analyses.

Neurodegeneration in the Cochlea after Blast Exposure

Figure 8:
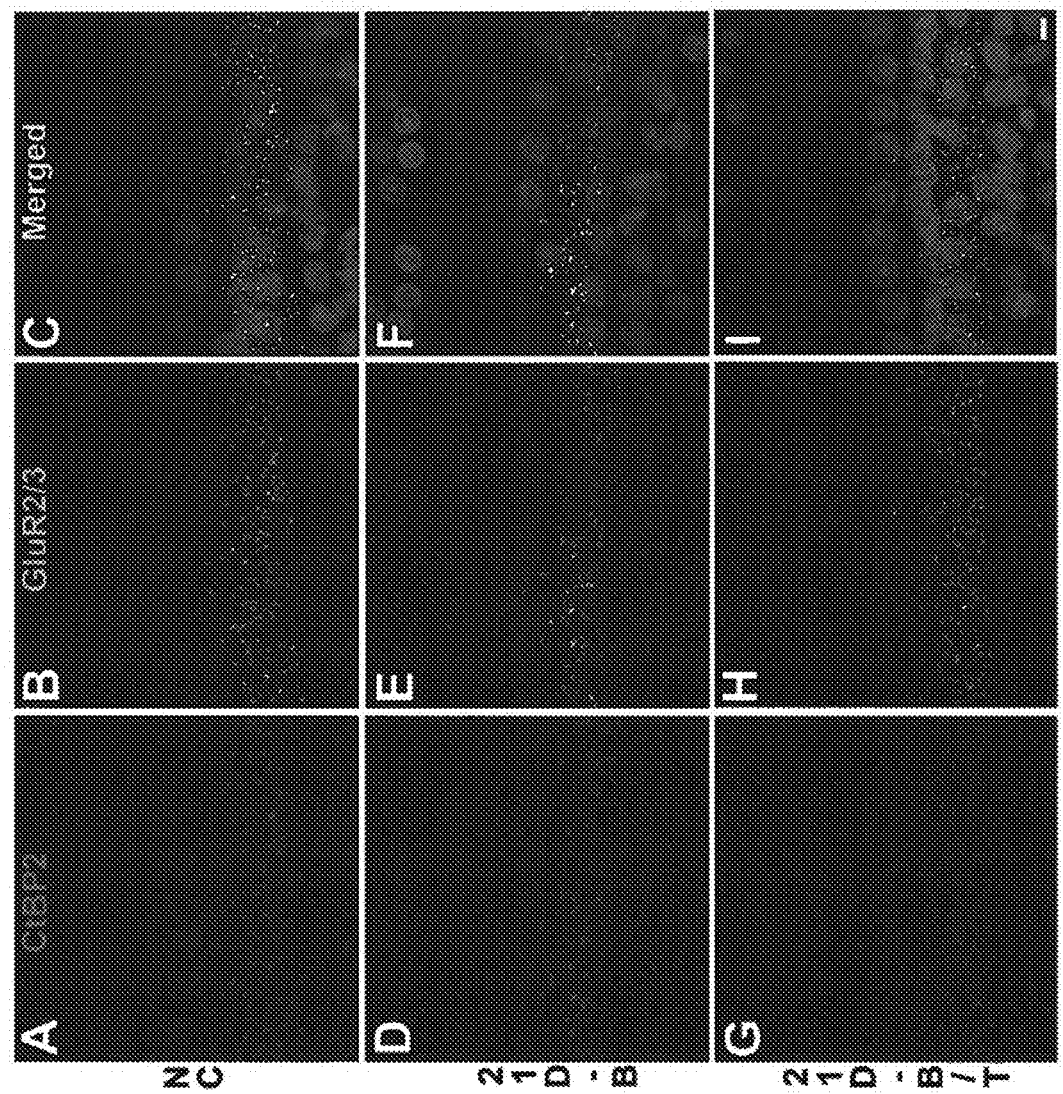
FIG. 8 shows that antioxidant treatment protects against cochlear ribbon synapse loss in response to blast-induced trauma. Confocal imaging shows a reduction in CtBP2- and GluR2/3-immunolabeling along the IHC basolateral membrane in the middle turn (16 kHz region) of the OC in blast-exposed animals 21 days after exposure (D-F) relative to naïve, age-matched controls (A-C). Animals treated with a combination of HPN-07 and NAC after blast exposure showed no such gross loss of IHC synaptic foci in this region of the OC (G-I). Presynaptic ribbons are labeled with anti-CtBP2 antibodies (red), and post-synaptic densities are labeled with anti-GluR2/3 antibodies (green). Merged images in the far-right panels reveal overlapping signal intensities for the two synaptic markers for each condition (yellow). Confocal images are maximal projections of z-stacks of ribbons within 8-10 IHCs in the 16 kHz region. Scale bar=5 µm in I for A-I.
Figure 9:
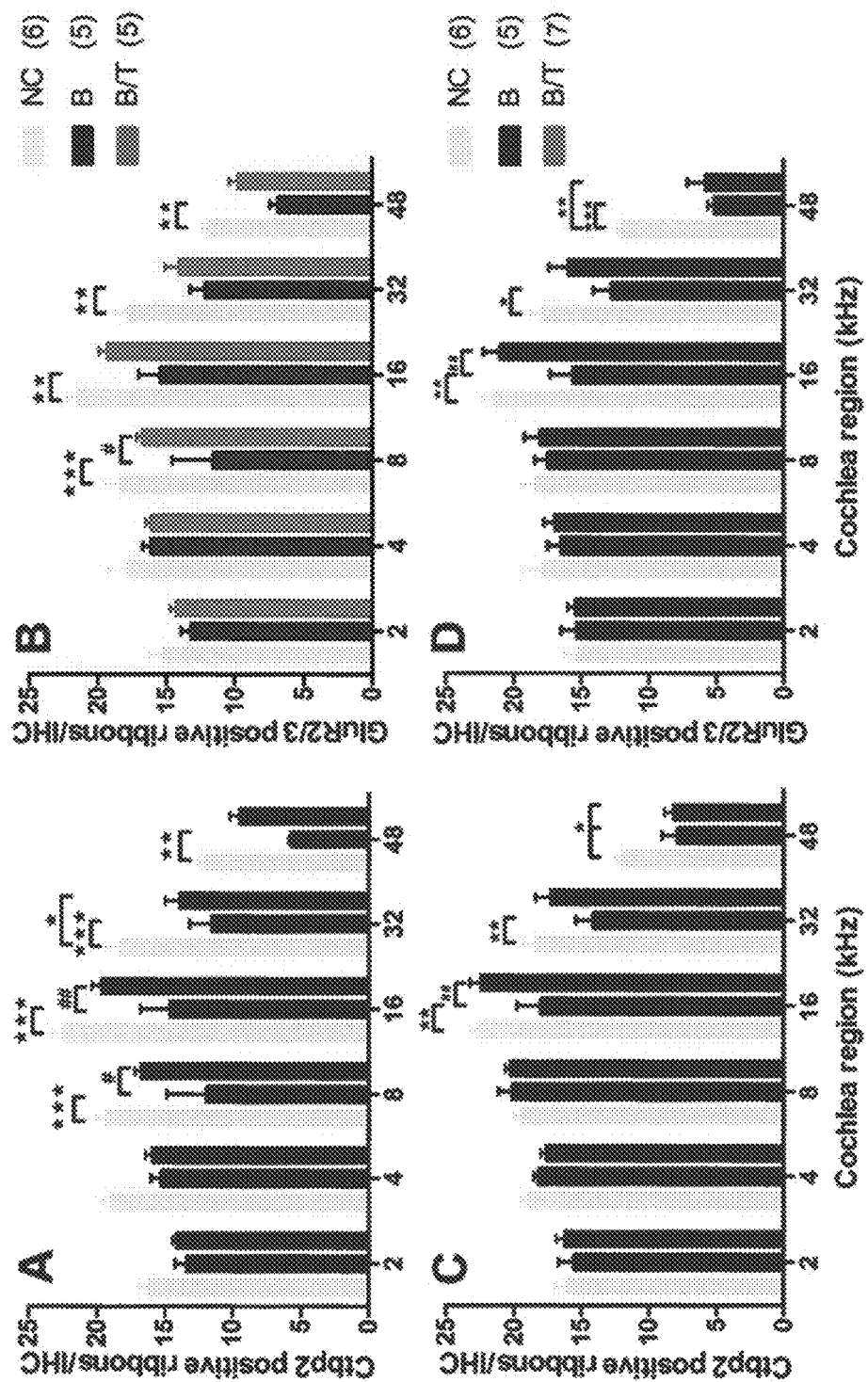
FIG. 9 shows that acute therapeutic intervention with HPN-07 and NAC reduces ribbon synapse loss within IHCs in the 16-32 kHz region of the OC of blast-expose animals. Synaptic marker counts among IHCs in the 2, 4, 8, 16, 32, and 48 kHz regions of the OC in age-matched naïve controls and untreated and antioxidant-treated cohorts of blast-exposed animals 7 days (7D, A and B) or 21 days (21D, C and D) after blast exposure were performed. Coordinated, statistically-significant losses of both pre- and post-synaptic markers were observed among IHCs in the 8-48 (7D) and 16-48 (21D) kHz regions in untreated, blast-exposed animals. Significant treatment effects of antioxidants for opposing blast-induced loss of these synaptic markers were identified in the 8 and 16 kHz region of the OC, and a trend towards statistical significance for antioxidant treatment was observed in the 32 (7D and 21D) and 48 (7D) kHz region. No such treatment effect was observed in the 48 kHz region at 21 days post-blast exposure. Statistical significance of the group differences for ribbon synapse loss is indicated by asterisks: *, , or *, $p<0.05, 0.01$, or $0.001$, respectively, while statistical significance of antioxidant treatment effects is denoted by ## for $p<0.01$. Error bars represent the standard error of the means (SEM). Numbers in parentheses represent the total number of OCs evaluated in each cohort.

Cochlear neurodegeneration is typically initiated within the fragile axonal neurites that innervate HCs and often progressively manifests as the loss of nerve fibers in the SL, ultimately culminating in the loss of SGNs (Jensen et al., PLoS One 10. doi:10.1371/journal.pone.0125160 (2015)). As a result, blast-induced neurotrauma in the OC was evaluated by examining the relative densities of ribbon synapses and NF-200-positive (Type I) neurites in the IHC innervation zone among naïve and blast-exposed rats. Dual immunolabeling analyses using antibodies against a major ribbon marker (C-terminal binding protein 2, CtBP2) and a marker for post-synaptic glutamate receptor patches (GluR2/3) revealed coordinated blast-induced reductions in pre- and post-synaptic structures, spanning from the basal to middle turns of the OC at both 7 and 21-days post-injury (FIG. 8, A-F). In contrast, low frequency tonotopic positions in the apical turn were seemingly spared from blast-induced synapse loss. Independent quantification of these pre- and post-synaptic markers provided clear evidence for tonotopic-specific synaptopathy that was graded in severity from the basal turn to the middle turn in blast-exposed rats (FIG. 9). In naïve rats, about 11-24 dual-labeled synaptic foci per IHC were observed in whole mount confocal sections spanning from the basal to middle turns of the OC. These numbers dropped precipitously in untreated, blast-exposed rats, such that less than 50% of the normal number of post-synaptic elements were observed among IHCs within the basal turn (i.e. 48 kHz tonotopic region) at seven-days post-exposure. Ribbon synapse densities were also significantly reduced over the 8-32 kHz tonotopic range (38.1, 35.8 and 37.3% reductions in CtBP2 puncta/IHC and 34.7, 28.8 and 34.7% reductions in GluR2/3 puncta/IHC, respectively, at 8, 16, and 32 kHz regions) in untreated rats at this evaluation interval. At 21-days post-exposure, significantly reduced ribbon synapse densities were still evident over the 16-48 kHz tonotopic range in untreated animals (FIG. 9). However, ribbon synapse densities appeared to recover in the more apical, 8 kHz, tonotopic position in these animals by this terminal time point (FIG. 9), perhaps indicative of a regionalized degree of spontaneous reinnervation over time.

Figure 19:
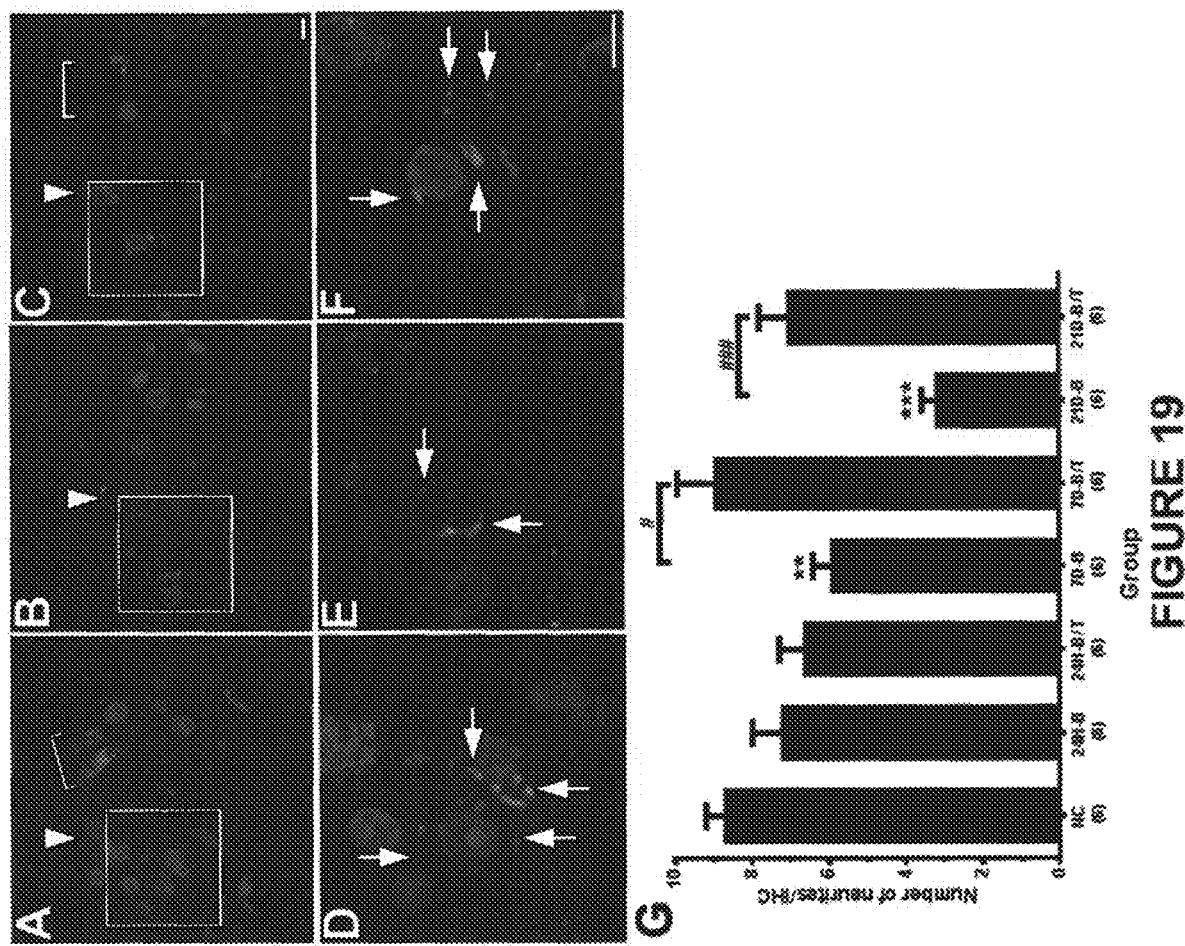
FIG. 19 shows that antioxidant treatment protects against blast-induced neurite loss within the IHC innervation zone. Images in A-F are examples of NF-200 positive stained neurites (pink, arrows in A-C) in the IHC area of the middle turn of the cochlea from naive rats (A, D); untreated, blast-exposed animals at 21 days after blast exposure (B, E); and HPN-07/NAC-treated, blast-exposed animals at 21-days post-blast (C, F). The rectangles in A-C indicate the locations from which images were collected for D-F. Fewer NF-200 positive neurites were observed along the IHC innervation zone (arrows in E) in the cochlea of untreated, blast-exposed animals compared to normal controls (arrows in D) or blast-exposed animals treated with HPN-07 and NAC (arrows in F). Arrowheads and brackets in A-C indicate IHCs and OHCs (green), respectively. Nuclei were stained by DAPI (blue). The number of NF-200-positive neurites adjacent to each IHC in the middle and basal turns of the cochlea was counted and statistically analyzed for each cohort at each sampling interval (G). There was a significant reduction in the number of NF-200-positive neurites per IHC in untreated, blast-exposed animals at seven and 21 days after post-blast (7D-B and 21D-B) compared to normal controls (NC,  or *, p<0.01 or 0.001). A significant degree of protection against NF-200-positive neurite loss in the IHC innervation zone was observed in the blast-exposed animals acutely treated with HPN-07 and NAC at both seven and 21 days after blast exposure (7D-B/T and 21D-B/T) compared to untreated, blast-exposed animals (# or ###, p<0.05 or 0.001). Error bars represent the standard error of the means (SEM). Numbers in parentheses represent the total number of animals evaluated in each cohort at each time point. Scale bars=5 µm, in C applies to A-C, in F applies to D-F.

To track whether this blast-induced neuropathic response translated to peripheral axon retraction over time, longitudinal changes in relative neurite densities were inspected along the IHC innervation zone at successive time points of 24 hours, 7 days, and 21 days post-blast. In naïve rats, approximately eight distinct NF-200-positive neurites per IHC were observed in serial sections spanning from the basal to middle turns of the OC (FIGS. 19A and 19D). Longitudinal analyses among blast-exposed rats revealed an unambiguous decline in the number of NF-200-positive neurites along the IHC innervation zone at successive time points after the damaging insult (FIGS. 19B and 19E). Formal quantification of these neurites confirmed the apparent time-dependent loss of immunolabeling along this interface, with significant attrition first evident at seven days post-blast (FIG. 19G). At the 21-day terminal sampling interval, an average neurite loss of approximately 60% was observed adjacent to IHCs in the basal through middle turns of the OC in untreated, blast-exposed animals. This degree of neurite loss is moderately greater than that anticipated from the average blast-induced ribbon synapse loss measured along this same region at this time point and may reflect the inherent reduction in resolution associated with quantification of neurite densities from tangential cross-sections. Nonetheless, these results indicate a pronounced decline in neurotransmission from the peripheral auditory system in the mid- to high-frequency range in response to blast injury, under conditions in which only 1-2% of IHC loss was documented (FIG. 9 and FIG. 19).

Figure 10:
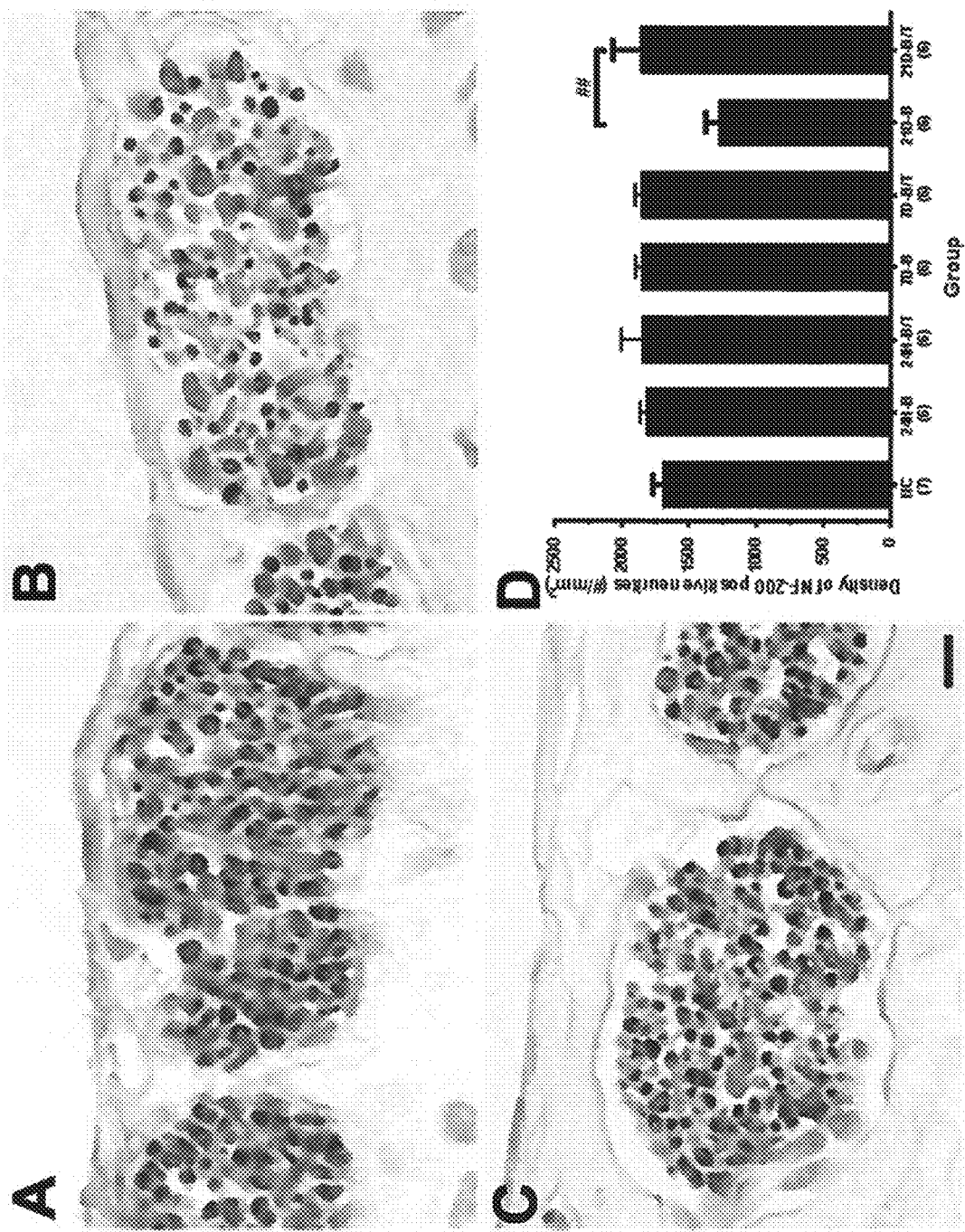
FIG. 10 shows combinatorial antioxidant intervention protects against blast-induced nerve fiber loss in the osseous SL. Images in A-C are examples of NF-200-positive stained nerve fibers in cross-sectional views of the SL (A-C) from the middle turns of normal controls (A); untreated, blast-exposed rats 21 days after the insult (B); and antioxidant-treated, blast-exposed rats at 21 days post-blast (C). Fewer NF-200-positive nerve fibers were observed in the SL in the cochlea of untreated, blast-exposed animals 21 days after blast exposure (B) compared to normal controls (A) and blast-exposed animals treated with HPN-07 and NAC (C). Quantification of NF-200-positive nerve fibers in the SL of the middle and basal turns of cochleae from each experimental cohort was conducted, and the density of neurites was estimated and statistically analyzed (D). The number of NF-200 positive neurites in the SL of untreated, blast-exposed animals was significantly decreased at 21 days after blast exposure compared to NCs ($p<0.05$, *). No such reduction in NF-200-positive neurites in the SL was observed in the HPN-07/NAC-treated, blast-exposed animals 21 days after blast exposure ($p<0.01$, ##, compared to untreated, blast-exposed animals). No significant changes in neurite density were observed at early time points among any of the cohorts (all $p>0.05$). Scale bar=10 µm in C for A-C. Numbers in parentheses represent the total number of animals evaluated in each cohort at each time point. Error bars in D represent SEM.

The relative density of NF-200-positive nerve fibers in the osseous SL was studied as a means of further evaluating progressive retrograde neurodegeneration in the cochleae of untreated, blast-exposed rats. As shown in FIG. 10, bundles of NF-200-positive nerve fibers that laterally project outward from the SG to innervate HCs are tightly packed within the osseous SL of naïve control rats (FIG. 10A). While apparent differences in the density of these nerve fibers were not evident at 24 hours and seven days after blast, an appreciable reduction in NF-200 staining intensity and nerve fibers density was first discernible in rats at 21 days after the blast exposure (FIG. 10B). Formal quantification of SL nerve fibers densities over time supported these initial observations, revealing that significant attrition occurred between the seven- and 21-day intervals post-blast (FIG. 10D). These results indicate progressive retrograde neurodegeneration beyond the initial loss of neurites along IHC synaptic junctions first observed at the seven-day sampling interval (FIG. 19G).

This temporal neuropathic trend was also manifested among the neurons that comprise the SG, such that the first appreciable loss of NF-200 staining in the middle and basal turns of this cochlear nerve center was evident at 21 days after blast exposure (FIG. 11B). In normal control animals, the majority of neuronal somata were immunopositive for NF-200 labeling, with a few cell bodies in each cross-section that exhibited strong immunohistochemical intensity (FIG. 11A). These intensely-labeled NF-200-positive neurons have previously been shown to represent type II neurons, and, therefore, the neurons with light perikaryal staining in naïve controls are assumed to be type I neurons. To clarify the type of degenerating neurons observed in the SGs from blast-exposed animals, the percentages of both weakly- and strongly-stained NF-200-positive somata were independently calculated and statistically analyzed. At 21-days post-blast, the percentages of weakly NF-200 immunopositive neurons were significantly decreased compared to normal control animals, while neurons that were strongly immunopositive for NF-200 staining were significantly elevated as early as seven days after blast exposure and remained elevated throughout the remainder of the 21-day recovery period (FIGS. 11D and 11E). This increase in perikaryal accumulation of NF-200 in the SG of blast-exposed animals likely represents cytoskeletal destabilization in type I neurons associated with trauma-induced demyelination and ongoing neurodegeneration.

Taken together, the results from these spatiotemporal evaluations suggested that, following the initial blast-induced trauma, progressive cochlear neurodegeneration occurs in a retrograde fashion, ultimately culminating in the apparent loss of neurofilament integrity among type I neurons in the SG. Without being bound by a theory, the progressive destabilization of cochlear neurons might be complemented by a time-dependent increase in NF-68 immunostaining in the SG in response to blast.

Figure 11:
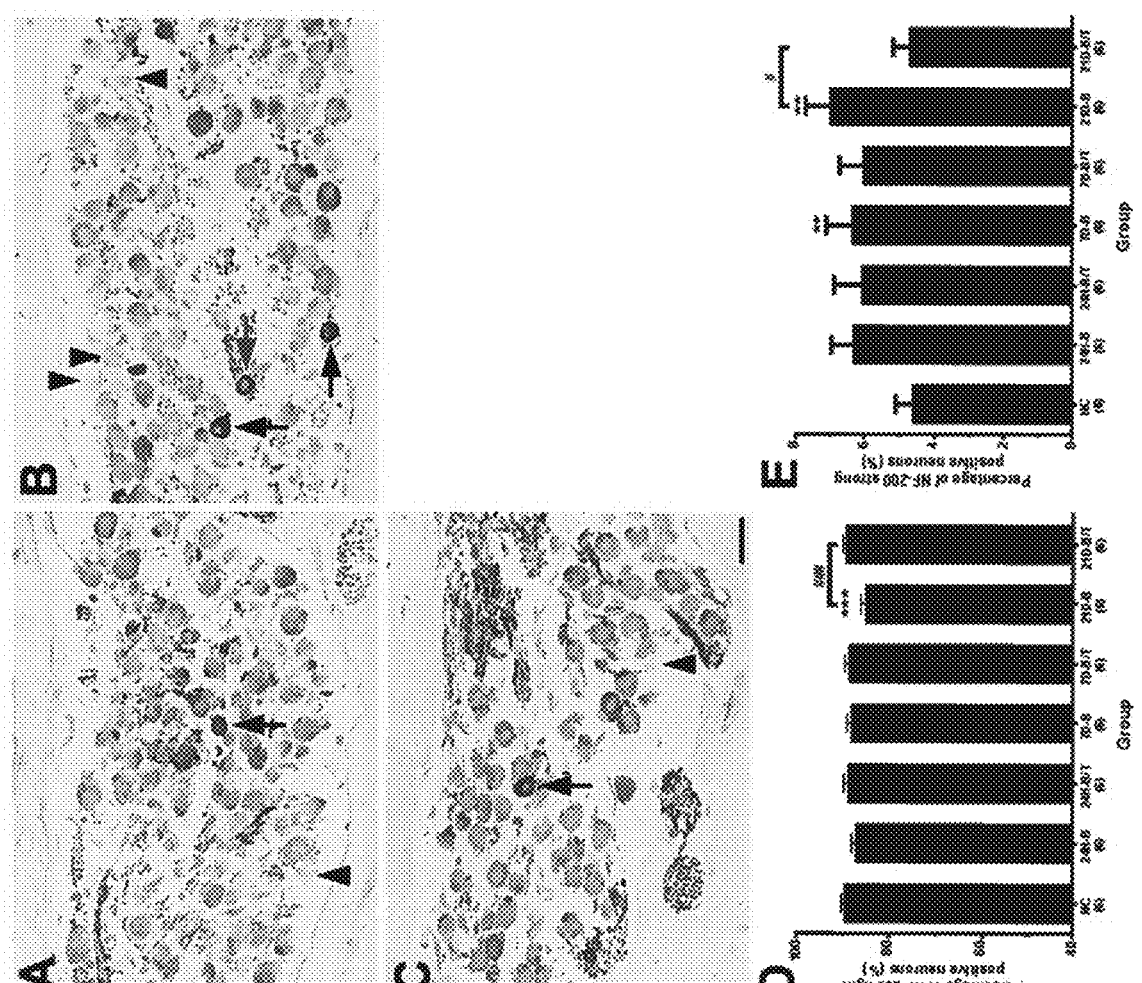
FIG. 11 shows antioxidant treatment reduces evidence of blast-induced neurodegeneration in the SG. Images in A-C are examples of NF-200 staining in the SG in the basal turn of normal controls (A); untreated, blast-exposed rats at 21-days post-blast (B) and treated, blast-exposed rats at 21 days in rats (C). The majority of neurons in the SG were positively stained for NF-200 (lightly positive), while a few neurons were intensely immunoreactive in each cohort (strongly positive, arrows in A-C). Arrowheads in A-C denote neurons that were not immunolabeled by the NF-200 antibody. The number of NF-200 light or strong positive neurons in the SG was quantified, and their relative percentages in each sample were calculated based on comparisons to the total number of neurons (D and E). Differences in these percentiles between cohorts at each time point were then statistically analyzed. A decreased percentage of NF-200 light positive neurons was observed in the SGs of untreated, blast-exposed animals at 21 days after blast exposure compared to NCs ($p<0.001$, *). A positive, statistically-significant treatment effect against loss of NF-200 light positive cells was observed at this time point (21D-B vs. 21D-B/T, $p<0.001$, ###, D). An increased percentage of NF-200 strong positive neurons was observed in the SGs of untreated, blast-exposed animals at 7 and 21 days after blast exposure compared to NCs (all $p<0.01$, ). A positive, statistically-significant treatment effect against increase of NF-200 strong positive cells was observed at 21 days after blast exposure (21D-B vs. 21D-B/T, $p<0.05$, #, E). Numbers in parentheses represent the total number of animals evaluated in each cohort at each time point. Error bars represent SEM in D and E. Scale bar=20 µm in C for A-C.
Figure 12:
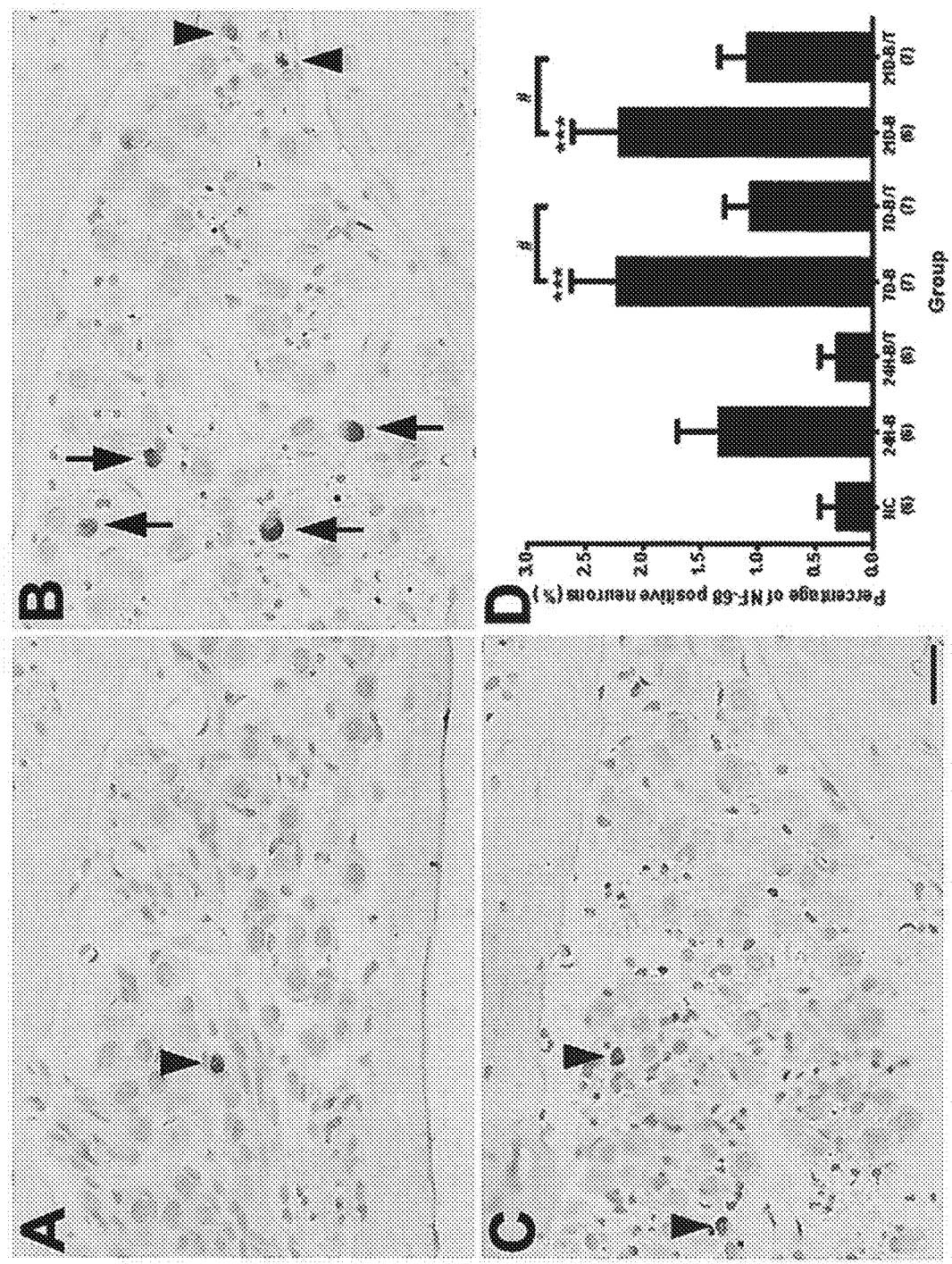
FIG. 12 shows therapeutic intervention with HPN-07 and NAC significantly reduced pathological increases in NF-68 immunolabeling within the SG in response to blast. Images in A-C are examples of NF-68 immunostaining in the basal turns of the SG from NC rats (A); untreated, blast-exposed rats at seven days after injury (B); and antioxidant-treated animals at seven days after blast exposure (C). Note that, while some small neurons were NF-68-positive under all conditions (arrowheads in A-C), multiple large, NF-68-positive neurons were uniquely evident in blast-exposed animals at seven days after injury (arrows in B). The total number of NF-68-positive neurons was counted in each cohort at each sampling interval, and the percentage of NF-68 positive neurons was calculated and statistically analyzed (D). A significant increase in the number of NF-68-positive neurons was observed in the SG of untreated, blast-exposed animals at seven and 21 days after blast exposure (all $p<0.001$, ***). A significant antioxidant treatment effect was identified at both the seven- and 21-day time points after blast exposure (all $p<0.05$, #). Scale bar in C=20 µm for A-C. Error bars in D represent SEM. Numbers in parentheses represent the total number of animals evaluated in each cohort at each time point.

As shown in FIG. 12, NF-68 immunolabeling of SGs from naïve rats resulted in a diffuse staining pattern in which darkly-stained neurons were relatively rare (i.e. less than 0.5%, FIGS. 12A and 12D). However, in blast-exposed rats, an aberrant NF-68 immunoreactivity pattern was acutely observed at 24 hours after blast and became progressively more pronounced with time (FIGS. 12B and 12D), such that at 21 days after the bTBI, the number of SGNs with intense NF-68 immunostaining had ballooned to more than sevenfold of that observed in naïve controls. These results are consistent with the perceived neurodegenerative response pattern revealed by NF-200 immunolabeling (FIG. 11). Despite its measurable somatic accumulation, no aberrant NF-68 immunoreactivity was detected among SG nerve fibers within the SL from naïve controls or blast-exposed rats at any time point after blast exposure.

Figure 13:
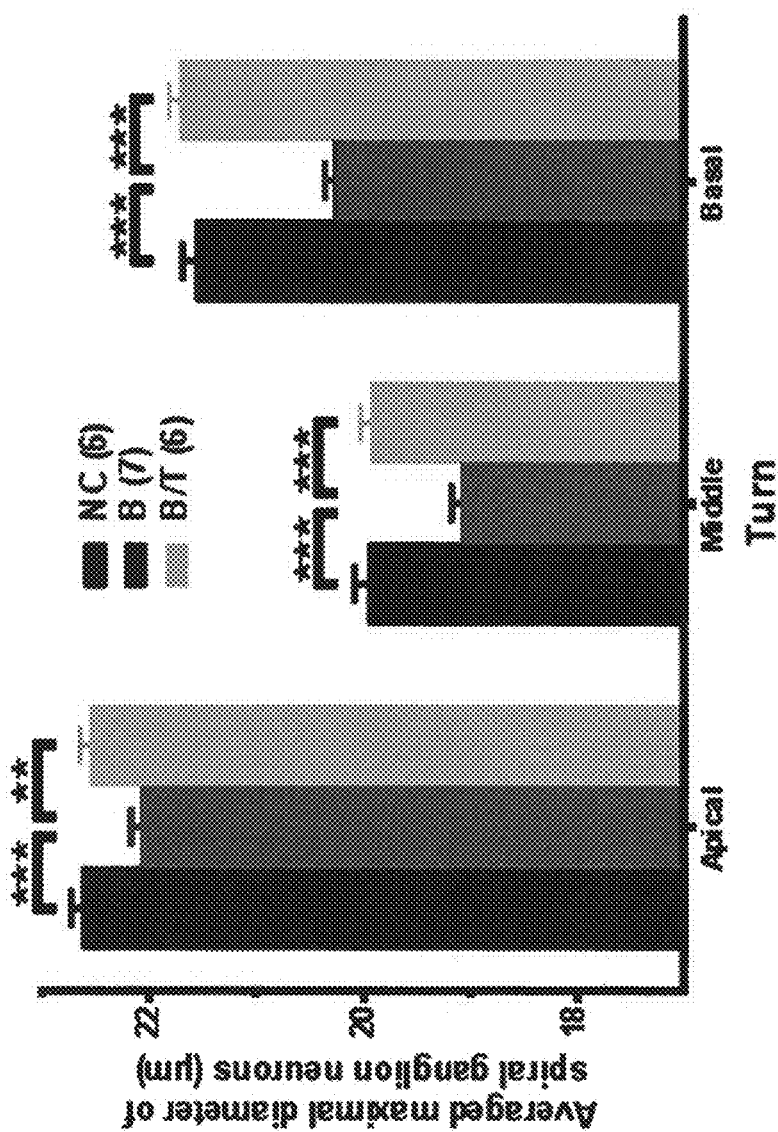
FIG. 13 shows antioxidant treatment reduces evidence of blast-induced neurodegeneration in the SG. Maximal diameters of spiral ganglion neurons were measured and statistically analyzed in naïve controls and in both untreated and HPN-07/NAC-treated animals at 21 days after blast exposure. Significantly decreased soma diameters were observed in the cochlea of untreated, blast-exposed animals, in all three turns compared to naïve controls (all $p<0.001$, ***). In the HPN-07/NAC-treated, blast-exposed animals, the mean soma diameters in all three turns were statistically indistinguishable from naïve controls (all p>0.05). Numbers in parentheses represent the total number of animals evaluated in each cohort.

In support of this apparent neurodegenerative response, the average cell body diameter of SG neurons was also significantly decreased in the cochleae of untreated, blast-exposed animals in all three turns at 21-days post-trauma in comparison to naïve controls (all $p<0.001$, FIG. 13). However, SGN density analyses indicated that neuronal atrophy had not yet translated into significant losses of neurons, as the total number of toluidine blue-positive SGNs were not significantly reduced at this terminal time point (all $p>0.05$).

Antioxidants Reduce Neurodegeneration in the Cochlea after Blast Exposure

To specifically examine the temporal effects of this treatment regimen on the structural integrity of blast-exposed cochlear neurons, Applicants evaluated the ribbon synapse and neurofilament immunostaining patterns described above among cohorts of blast-exposed animals subsequently treated with HPN-07 and NAC. In contrast with untreated, blast-exposed animals, at seven days post-trauma, antioxidant-treated rats did not exhibit a statistically-significant loss of ribbon synapses in the 8 and 16 kHz regions of the OC (FIGS. 9, A and B). These therapeutic effects were temporally extended to 21-days post-blast, as ribbon synapse densities were indistinguishable from naïve controls within the 16 kHz region in antioxidant-treated animals (FIG. 8, panels G-I and FIGS. 9, C and D). At this terminal time point, an apparent positive antioxidant treatment effect was also observed in the 32 kHz region, although the extent of efficacy did not meet our criteria for statistical significance (i.e. $p>0.05$, FIGS. 9, C and D). HPN-07 and NAC treatment also reduced gross neurite loss within the IHC innervation zone in the middle and basal turns in response to neuropathic blast levels (FIGS. 19C and 19F). Furthermore, the progressive loss of synaptic neuritic processes observed in untreated rats was virtually absent in antioxidant-treated animals, such that there was no significant difference in the number of neurites per IHC in treated, blast-exposed animals relative to naïve controls at the terminal, 21-day time point (FIG. 19G).

The ramifications of this therapeutic effect were also manifested in a retrograde fashion, as antioxidant intervention efficiently counteracted the propagative loss of nerve fibers in the osseous SL induced by the acute blast insult (FIG. 10C). In these treated animals, the densities of SL nerve fibers were indistinguishable from naïve controls at the terminal sampling interval of 21 days post-blast (FIG. 10D). The treatment efficacy was also evident in the SG, where a full complement of weakly-stained, NF-200-positive type I neurons was detected throughout the experimental time course in blast-exposed rats that were administered HPN-07 and NAC (FIG. 11). This observation was complemented by a significant treatment-induced reduction in the number of NF-68-positive neurons in the SG at each sampling interval post-blast (FIGS. 12C and 12D). Moreover, in contrast to the effects observed in untreated, blast-exposed rats, the average size of SG neurons in all three turns in animals treated with HPN-07 and NAC was indistinguishable from naïve controls at the terminal sampling interval of 21-days post-blast (all $p>0.05$, FIG. 13). Thus, combinatorial antioxidant intervention appeared to efficiently short-circuit blast-induced neurodegeneration in the peripheral auditory system.

Blast Exposure Induces Hyperphosphorylation and Oligomerization of Tau in Spiral Ganglion Neurons Pervasive hyperphosphorylation and oligomerization of hippocampal Tau were induced in response to these blast conditions, both of which have been shown to be capable of initiating prion-like propagative waves of transcellular dysfunction independent of obvious ongoing injury. As such, the accumulation of neurotoxic Tau in cochlear neurons occurred was examined as a coincident sequela with blast.

Cochlear evaluations started with an endogenous Tau antibody, Tau-1, that recognizes physiological isoforms of Tau lacking phosphorylation at serine sites 195, 198, 199, and 202 and which was useful for making physiological versus pathological distinctions. However, the Tau-1 antibody did not exhibit any detectable immunoreactivity with normal cochlear neurons or nerve fibers. Under physiological conditions, Tau can exist as one of six distinct isoforms resulting from alternative splicing (Buée et al., Brain Res. Rev., 33, 95-130 (2000)). Moreover, these isoforms are subjected to context-specific post-translational modifications, including differential phosphorylation, that modulate functional interactions with microtubules. Thus, Applicants used an alternative physiologically-relevant antibody, Tau-46, which recognizes all six native isoforms of Tau. Using this antibody, strong Tau-46 positive staining was observed in nerve fibers in the SL and nerve fibers beneath HCs within normal OCs. Moderate Tau-46 immunolabeling was also observed in the cytoplasm of Pillar, Deiter's and Hensen's cells, and relatively weak staining was observed in IHCs and outer HCs (OHCS). This cochlear distribution pattern is similar to that described in previous reports of physiologic Tau in this organ and for other microtubule-associated proteins, such as alpha- and beta-tubulin (Despres et al. 1994; Oshima et al. 1992; Du et al., 2003; Slepecky and Ulfendahl 1992). In the SG, diffuse, positive Tau-46 staining was observed in the soma of neurons. However, approximately 10% of SGNs exhibited strong positive staining in naïve rats (Table. 1). The spiral ligament and the stria vascularis also exhibited diffuse Tau-46 staining (data not shown). These results indicate that, in contrast to previous reports, the localization and distribution of Tau protein is seemingly very broad in the cochlea (Despres et al. 1994; Oshima et al. 1992; Slepecky and Ulfendahl 1992) and that the normal phosphorylation status of Tau in cochlear neurons and sensory epithelia likely differs from that observed in hippocampal neurons (Du et al., 2016).

TABLE 1

Normal Tau staining in the auditory system after blast exposure and antioxidant treatment

|  | NC | 24 H-B | 24 H-B/T | 7 D-B | 7 D-B/T | 21 D-B | 21 D-B/T | Treatment effects |
| --- | --- | --- | --- | --- | --- | --- | --- | --- |
| SG (Tau-46, %) | 9.04 ± 0.6 | 10.01 ± 1.28 | 9.29 ± 0.79 | 10.01 ± 0.68 | 8.23 ± 0.8 | 12.39 ± 1.08 | 7.74 ± 0.92 | 21 D ($p < 0.05$) |

TABLE 1-continued

Normal Tau staining in the auditory system after blast exposure and antioxidant treatment

| | NC | 24 H-B | 24 H-B/T | 7 D-B | 7 D-B/T | 21 D-B | 21 D-B/T | Treatment effects |
|---|---|---|---|---|---|---|---|---|
| SG (Tau-1) | NS | NS | NS | NS | NS | NS | NS | No |
| AVCN (Tau-1, #/mm²) | 58.82 ± 6.95 | 58.3 ± 10.18 | 59.99 ± 9.82 | 83.59 ± 8.09 | 59.91 ± 7.79 | 54.38 ± 9.07 | 46.95 ± 6.6 | No |
| PVCN (Tau-1, #/mm²) | 45.69 ± 5.12 | 64.06 ± 8.18 | 64.43 ± 10.72 | 82.22 ± 8.23* | 81.92 ± 8.18* | 32.52 ± 4.97 | 47.64 ± 4.95 | No |
| DCN (Tau-1, #/mm²) | 94.78 ± 5.94 | 118.4 ± 8.21 | 94.29 ± 5.67 | 122.3 ± 7.55 | 107.8 ± 5.71 | 79.17 ± 6.63 | 100.1 ± 5.23 | No |
| IC (Tau-1, #/mm²) | 56.6 ± 8.02 | 54.75 ± 6.91 | 26.65 ± 4.73* | 80.33 ± 5.09 | 55.46 ± 7.22 | 47.71 ± 7.07 | 54.93 ± 7.66 | 24 H (p < 0.05) |
| AC (Tau-1, #/mm²) | 7.58 ± 1.13 | 17.1 ± 1.66*** | 17.76 ± 1.68*** | 14.69 ± 1.82* | 10.56 ± 1.29 | 27 ± 1.94*** | 15.46 ± 1.43** | 21 D (p < 0.001) |

Note:
The numbers represent mean ± SEM; "NS" means no positive staining; "*, , *" means p < 0.05, 0.01, 0.001, respectively, compared to NCs; "Treatment effects" means comparison between blast-exposed (B) and blast-exposed treated (B/T).

Somatic accumulation of normal Tau protein is a hallmark of many acute and chronic neurodegenerative disorders in response to axonal microtubule destabilization (Kowall and Kosik, 1987; Wolfe, 2012). However, the qualitative and quantitative evaluations of somatic Tau-46 immunoreactivity patterns among SGNs in the untreated, blast-exposed rats revealed no detectable differences in total Tau levels from that observed in naïve controls at any time point after blast exposure (all p>0.05,). Tau-46 immunoreactivity in the SL was also measured and statistically analyzed at the terminal 21-day time point, and the results from this analysis revealed moderate elevations in the number of nerve fibers that were intensely-immunopositive for Tau-46 (1846±182.83/mm2 compared to 1462±158.66/mm2 in naïve controls (p<0.05). In the HPN-07/NAC-treated, blast-exposed rats, the Tau-46 positive nerve fiber density (1313.98±128.23/mm2) was significantly reduced compare to untreated, blast-exposed rats (p<0.01) and statistically-indistinguishable from naïve controls (p>0.05).

In a pathological state, toxic insults, including oxidative stress, can lead to imbalances in the activities of specific kinases and phosphatases, which results in the hyperphosphorylation of Tau at critical microtubule regulatory sites leading to increased levels of unbound, hyperphosphorylated Tau in the soma of neurons (Noble et al., 2013; Taniguchi et al., 2001). To discern whether SGNs were susceptible to this destabilizing stress response pattern in blast-exposed rats, Applicants immunolabeled cochlear tissues from these animals and naïve controls with an antibody, AT8, that specifically recognizes hyperphosphorylated Tau.

Figure 14:
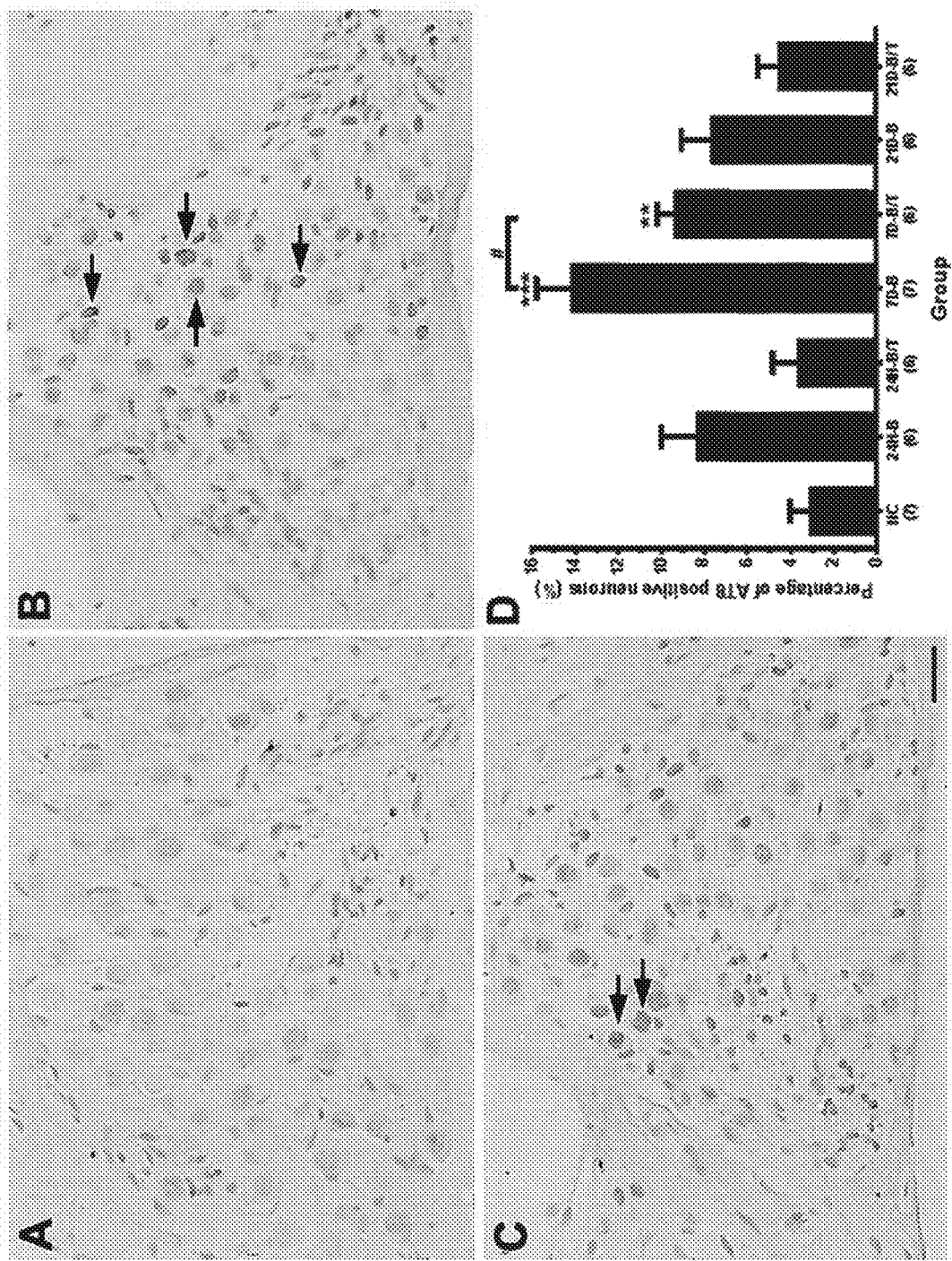
FIG. 14 shows that antioxidant treatment reduced the blast-induced accumulation of hyperphosphorylated Tau in the SG. Images in A-C are examples of AT8 immunostaining in the middle turn of the SG from normal control animals (A); untreated, blast-exposed rats at seven days post-blast (B); and antioxidant-treated rats at seven days after injury (C). The number of AT8-positive SGNs (arrows in B and C) was counted, and the percentage of AT8-positive neurons was calculated and used for statistical comparisons between experimental cohorts at each time point (D). Increased AT8 accumulation was observed in SGNs at seven days after blast exposure in untreated and treated rats (p<0.01 or 0.001,  or *). A significant HPN-07/NAC treatment effect was observed at this time point after blast exposure (p<0.05, #). Scale bar=20 µm in C for A-C. Numbers in parentheses represent the total number of animals evaluated in each cohort at each time point. Error bars in D represent SEM.

As shown in FIG. 14, the SG of naïve rats was largely unresponsive to immunolabeling with the AT8 antibody (FIGS. 14A and 14D). However, blast exposure induced both acute and chronic increases in somatic AT8 immunolabeling in SGNs, with peak immunoreactivity observed at the seven-day post-blast sampling interval (FIGS. 14B and 14D, Table 2). However, at 21 days after blast, the levels of these neurotoxic variants among SGNs had seemingly declined, suggesting that the deleterious effects of blast on this microtubule associated protein might be a transient phenomenon. The density of AT8-positive nerve fibers in the SL was also measured and statistically analyzed at seven days after blast exposure, a time point at which SGNs exhibited statistically-significant AT8 accumulation in untreated rats. However, the relative density of AT8-positive nerve fibers was not significantly increased in the SL of blast-exposed rats at this time point, irrespective of treatment, (227.53±22.20 and 253.93±24.90/mm2 for untreated and treated rats, respectively) in comparison to naïve controls (169.17±20.98, all p>0.05).

TABLE 2

AT8 staining in the auditory system after blast exposure and antioxidant treatment

| AT-8 | NC | 24 H-B | 24 H-B/T | 7 D-B | 7 D-B/T | 21 D-B | 21 D-B/T | Treatment effects |
|---|---|---|---|---|---|---|---|---|
| SG (%) | 3.18 ± 0.88 | 8.39 ± 1.63 | 3.74 ± 1.1 | 14.21 ± 1.57*** | 9.39 ± 0.79** | 7.69 ± 1.34 | 4.59 ± 0.91 | 7 D (p < 0.05) |
| AVCN (#/mm²) | 39.6 ± 8.58 | 40.82 ± 8.51 | 32.17 ± 8.07 | 45.87 ± 10.51 | 63.49 ± 11.02 | 34.84 ± 10.24 | 17.18 ± 5.38 | No |
| PVCN (#/mm²) | 29.12 ± 6.63 | 31.34 ± 7.89 | 30.64 ± 8.07 | 47.37 ± 8.19 | 51.91 ± 9 | 29.51 ± 9.64 | 25.18 ± 6.82 | No |
| DCN (#/mm²) | 26.12 ± 3.91 | 47.9 ± 7.23 | 27.12 ± 5.49 | 72.91 ± 6.79*** | 73.41 ± 8.41*** | 33.23 ± 6.24 | 29.38 ± 5.21 | No |
| IC | NS | NS | NS | NS | NS | NS | NS | |
| AC (#/mm²) | 3.23 ± 0.71 | 7.17 ± 1.42 | 6.75 ± 1.42 | 15.33 ± 2.36*** | 16.08 ± 3.02*** | 1.68 ± 0.42 | 3.04 ± 0.76 | No |

Hyperphosphorylation of Tau is often an etiopathological precursor of Tau oligomerization, as the phosphorylation events that initially destabilize its microtubule binding capacity result in a structural conformation that exhibits a propensity for self-association (Iqbal et al., 2013). This altered affinity pattern can lead to further Tau dysfunction, as physiological isoforms of Tau are recruited into dead-end pathological complexes with hyperphosphorylated isoforms, potentiating their neurodegenerative properties (Takashima 2013). To investigate whether our blast exposure model also induced an oligomerization effect on Tau in SGNs, Applicants immunolabeled SG sections from longitudinal time points post-blast with an antibody, T22, that specifically recognizes pathological Tau oligomers (Lasagna-Reeves et al., 2012). Similar to the observations with the AT8 antibody (FIG. 14A), the vast majority of naïve SGNs (>99%, FIG. 15D) were not immunoreactive with the T22 antibody (FIG. 15A). In contrast, novel and pervasive somatic T22 immunoreactivity was observed among SGNs from blast-exposed rats at all time points analyzed (FIGS. 15B and 15D, Table 3). The prevalence of this T22 immunolabeling pattern became more prevalent with time, contrasting with the trend observed with the AT8 antibody, the immunoreactivity of which declined after reaching peak levels at seven-days post-blast (FIG. 14D). The density of T22-positive nerve fibers in the SL was also measured and statistically analyzed at the time point of maximal T22 accumulation in SGNs (i.e. 21-days post-blast). Marked, statistically-significant increases in T22-positive nerve fibers were also observed in the SL of untreated, blast-exposed rats (516.99±58.17/mm2) at this time point compared to naïve controls (136.67±15.38/mm2, p<0.001). The perpetuation of this aberrant T22 SGN immunolabeling pattern in blast-exposed rats is indicative of sustained or progressive pathology in this auditory nerve center.

revealed by differential neurofilament staining could be extended to Tau dysfunction in the SG, Applicants immunolabeled relevant tissue sections from antioxidant-treated, blast-exposed rats at each sampling interval with AT8 and T22 antibodies for comparisons to naïve controls and untreated, blast-exposed cohorts. As depicted in FIG. 14 (panels C and D), acute post-injury intervention with a combinatorial regimen of HPN-07 and NAC reduced the manifestation of hyperphosphorylated Tau at all time points examined. Of particular note, significant reductions in the number of AT8-immunopositive neurons were observed in treated rats at the seven-day sampling interval when AT8 levels peaked in the untreated blast cohort (FIG. 14D and Table 2). However, antioxidant treatment did not reduce the number of AT8-positive neurons to the levels observed in naïve controls at this time point, perhaps underscoring a saturable or oxidative-stress-independent effect of blast on aberrant Tau phosphorylation in the SG.

Figure 15:
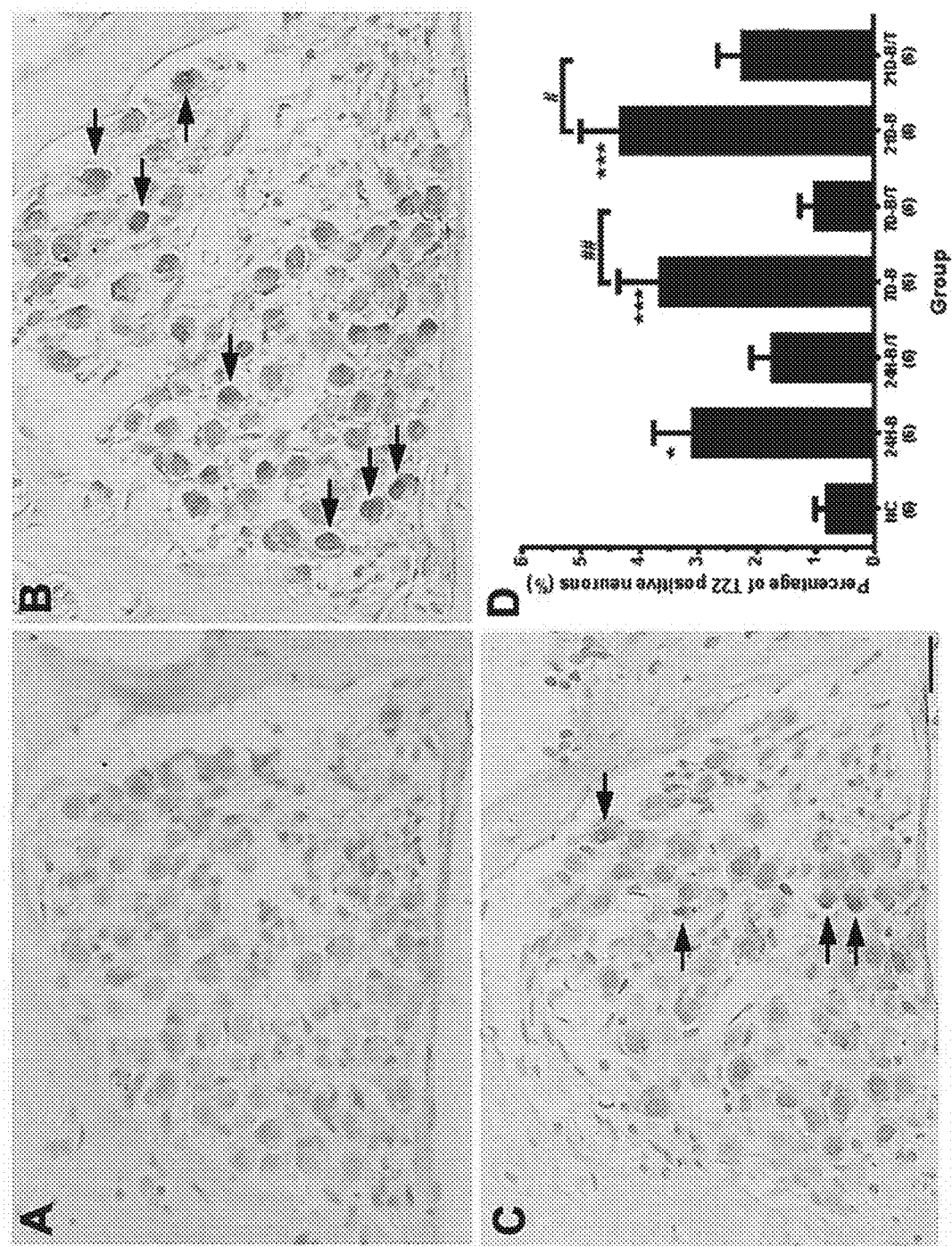
FIG. 15 shows that antioxidant treatment reduced the blast-induced accumulation of pathologic Tau oligomers in the SG. Images in A-C are examples of oligomeric Tau (T22) immunostaining in the middle turn of the SG of normal control rats (A); untreated, blast-exposed rats at seven days post-blast (B); and antioxidant-treated rats at seven days after injury (C). T22-positive neurons were observed in the untreated, blast-exposed animals (arrows in B) and in the antioxidant-treated, blast-exposed animals (arrows in C). The number of T22-positive neurons in the SG was quantified, and the percentage of T22-positive neurons in each cohort at each time point was calculated and statistically analyzed (D). An increased number of T22-positive neurons was observed in the SG of untreated, blast-exposed animals at all time points examined (p<0.05 or 0.001, * or ***). Significant treatment effects were observed for the seven and 21 day time points after blast exposure (p<0.05 or 0.01, # or ##), but not at the acute, 24 hour, time point after post-blast (p>0.05). Scale bar=20 µm in C for A-C. Numbers in parentheses represent the total number of animals evaluated in each cohort at each time point. Error bars in D represent SEM.

A complementary analysis with the oligomeric Tau antibody revealed an even more pronounced effect of HPN-07/NAC intervention among neurons in the SG of blast-exposed animals. Under these conditions, antioxidant intervention significantly and efficiently blocked the pathological increases in T22 immunolabeling observed in the cell bodies of untreated, blast-exposed rats throughout the entire time course of the study (FIG. 15, panels C and D, Table 3).

TABLE 3

T22 staining in the auditory system after blast exposure and antioxidant treatment

| | NC | 24 H-B | 24 H-B/T | 7 D-B | 7 D-B/T | 21 D-B | 21 D-B/T | Treatment effects |
|---|---|---|---|---|---|---|---|---|
| SG (%) | 0.85 ± 0.17 | 3.12 ± 0.64* | 1.77 ± 0.33 | 3.67 ± 0.69*** | 1.04 ± 0.22 | 4.34 ± 0.66*** | 2.27 ± 0.38 | 7 D (p < 0.01) and 21 D (p < 0.05) |
| AVCN | NS | NS | NS | NS | NS | NS | NS | No |
| PVCN | NS | NS | NS | NS | NS | NS | NS | No |
| DCN | NS | NS | NS | NS | NS | NS | NS | No |
| IC | NS | NS | NS | NS | NS | NS | NS | No |
| AC (#/mm$^2$) | 0.34 ± 0.14 | 0.46 ± 0.13 | 0.52 ± 0.19 | 34.16 ± 5.59*** | 31.42 ± 5.68*** | 13.89 ± 4.00 | 12.35 ± 2.22 | No |

Figure 16:
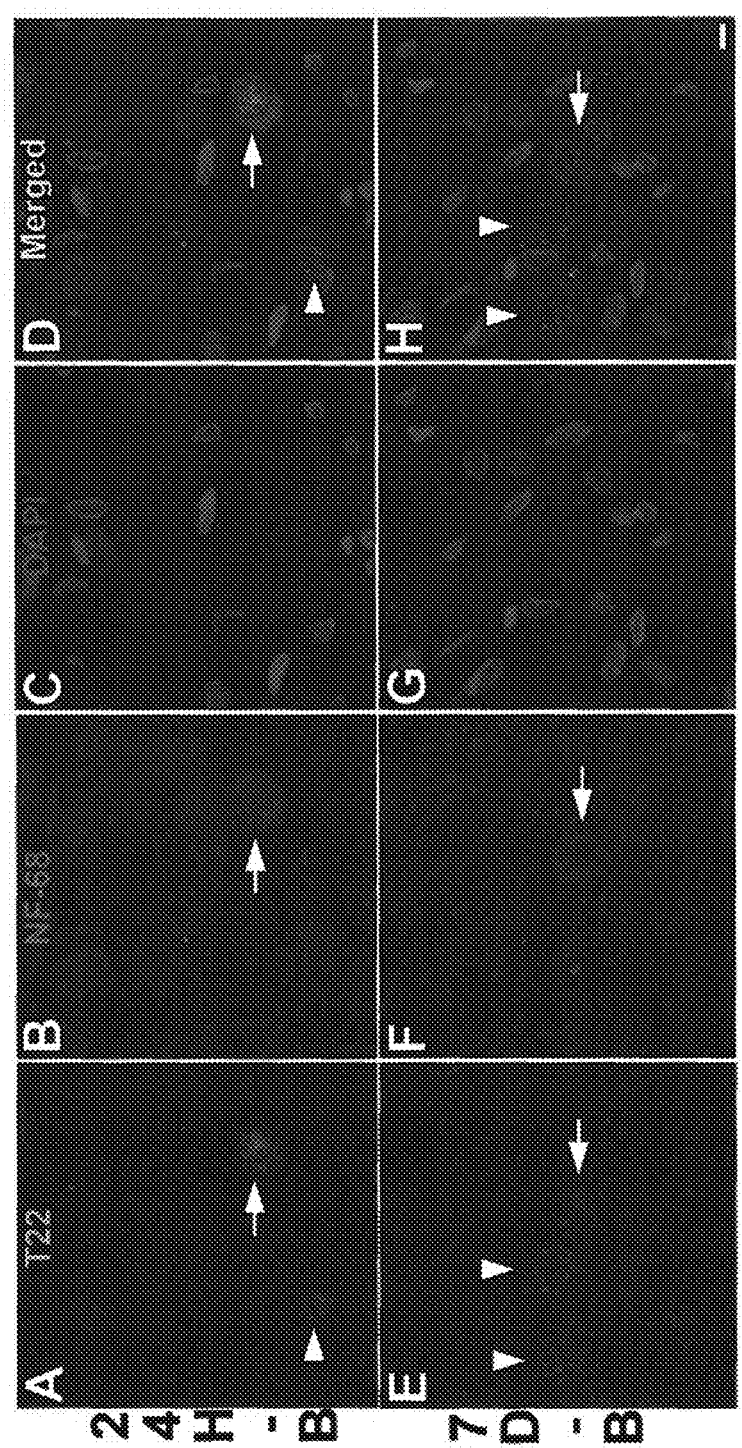
FIG. 16 shows blast exposure results in coincident somatic accumulation of oligomeric Tau and NF-68 fragments in SGNs. Images are examples of T22 and NF-68 double-labeling in the SG in the middle turn at 24 hours (A-D) or seven days (E-H) after blast exposure in untreated animals. SGNs immunopositive for both somatic NF-68 and nuclear and cytoplasmic T22 were uniquely observed in the SG in response to blast (green, arrows in A, B, D, E, F and H). Some T22-positive neurons without NF-68 labeling were also observed in the SG (red, arrowheads in A, E, D and H). Nuclei were stained by DAPI (blue). The scale bar in H=5 µm for A-H.

The T22 profile observed in blast-exposed rats was reminiscent of the NF-68 longitudinal immunolabeling pattern described above for this cohort. This prompted us to determine if these complementary trends were manifested as coincident pathophysiological responses in the same degenerating SGNs. To this end, SG tissue sections from blast-exposed rats were co-incubated with antibodies against NF-68 and oligomeric Tau and then evaluated for potential co-localization of these two pathological epitopes. An example of this immunofluorescence analysis is depicted in FIG. 16. Based on these analyses, it was evident that, although T22 immunolabeling was generally more prevalent than NF-68 at both acute and chronic sampling intervals, multiple T22-positive neurons at each time point were co-labeled with the NF-68 antibody (FIG. 16). The size and shape of these double-labeled neurons were consistent with type I SGNs. These results indicate that progressive, neurotoxic destabilization of Tau function and destabilization of neurofilaments are related events in degenerating SGNs in blast-exposed rats.

Antioxidant Treatment Reduces the Blast-Induced Accumulation of Neurotoxic Tau Variants in Spiral Ganglion Neurons To determine if the apparent therapeutic efficacy of HPN-07 and NAC intervention on cochlear neurodegeneration This positive treatment effect was also observed In the SL, where the T22-positive nerve fiber density (193.53±21.37/mm2) was significantly smaller than that of untreated, blast-exposed rats (516.99±58.17/mm2, p<0.001) and statistically-indistinguishable from naïve controls (p>0.05) at the terminal sampling interval. In conjunction with the positive treatment effects on the preservation of NF-200 staining in SGNs (FIG. 11) and the attenuation of pathologic NF-68 accumulation (FIG. 12), these results demonstrate that the previously-indicated therapeutic effects of this combinatorial antioxidant regimen in blast-exposed animals can be extended to include inhibition of neurodegeneration and progressive Tau dysregulation in the peripheral auditory system.

Antioxidants Reduce Somatic Tau Accumulation Among Neurons in the Auditory Cortex of Blast-Exposed Rats While combinatorial HPN-07/NAC treatment clearly ameliorated indications of ongoing, bTBI-related Tau dysfunction in the peripheral auditory system, the experiment sought to determine if repetitive blast exposure also induced pathologic changes on Tau in the central auditory system that were counteracted by therapeutic antioxidant intervention. To this end, tissue sections from the anterior ventral cochlear nucleus (AVCN), the posterior ventral cochlear nucleus (PVCN), the DCN, the IC, and the AC were evaluated for immunocytological evidence of Tau dysregulation in response to blast. In contrast to cochlear tissues, neurons within the central auditory pathway were diffusely immunoreactive with the conventional physiologic Tau-1 antibody in naïve control rats (FIG. 17A). This observation is consistent with Applicants' previous work on Tau immunoprofiling among hippocampal neurons (Du et al., 2016). In naïve controls, Tau-1-positive neurons distributed over all layers of the DCN and in all areas of the VCN and IC (Table 1), with very low frequencies of intense somatic immunoreactivity. In contrast to our previous evaluations of hippocampal neurons, blast exposure did not induce a significant change in somatic Tau-1 staining in the AVCN or DCN, and only a transient increase in somatic Tau-1 immunoreactivity was detected at the seven-day post-exposure sampling interval in the PVCN of untreated, blast-exposed animals ($p<0.05$, Table 1).

In the AC of naïve controls, Tau-1-positive neurons were primarily located in the deep neuronal layers. However, Tau-1-positive neurons were also observed in the middle layers after blast exposure. As graphically summarized in FIG. 17, significantly more Tau-1 positive somata were observed in neurons in the AC at all time points after blast exposure. This blast-induced effect was seemingly biphasic, as, after an initial plateau between 24 hours and seven-days post-blast, the number of neurons with dark somatic Tau-1 staining in the AC became further elevated at 21 days post-blast, perhaps reflective of both acute and progressive dysregulation of normal Tau function.

Examination of central auditory tissue sections with the AT8 antibody revealed no significant induction of blast-induced hyperphosphorylation in the AVCN, PVCN, or IC (Table 2). Minor transient increases ($p<0.05$, 2.8-fold increase) in somatic AT8 immunolabeling were observed in neurons of the DCN at seven days post-blast, with no detectable changes evident at the 24 hour or 21 day time points (Table 2). In the primary AC, a more pronounced ($p<0.01$, 4.76-fold increase), yet still transient, increase in AT8 immunoreactivity was observed at seven days post-blast relative to that detected in the DCN. However, this pathologic staining pattern was seemingly resolved by the 21-day sampling interval.

T22 immunolabeling exhibited a similar immunolabeling pattern to that observed with the AT8 antibody in the central auditory pathway in blast-exposed animals. No T22-reactive neurons were detected in the AVCN, PVCN, DCN, or IC in naïve animals (Table 3). Moreover, our model of bTBI failed to induce significant increases in somatic T22 immunoreactivity in these central auditory regions of the brain over the experimental time course of the study (Table 3). In contrast, the prevalence of T22-positive neurons in the AC was significantly ($p<0.001$, 100-fold increase) elevated at seven-days post-blast. However, this aberrant immunolabeling pattern was significantly reduced by the terminal (21-day) time point of the study (Table 3). Taken together, these results revealed that bTBI induced a sustained, if not progressive, somatic accumulation of physiologic Tau in neurons of the AC that was coupled with a transient, yet delayed (seven-days post-blast), accumulation of hyperphosphorylated and oligomeric Tau in this central auditory center.

Figure 17:
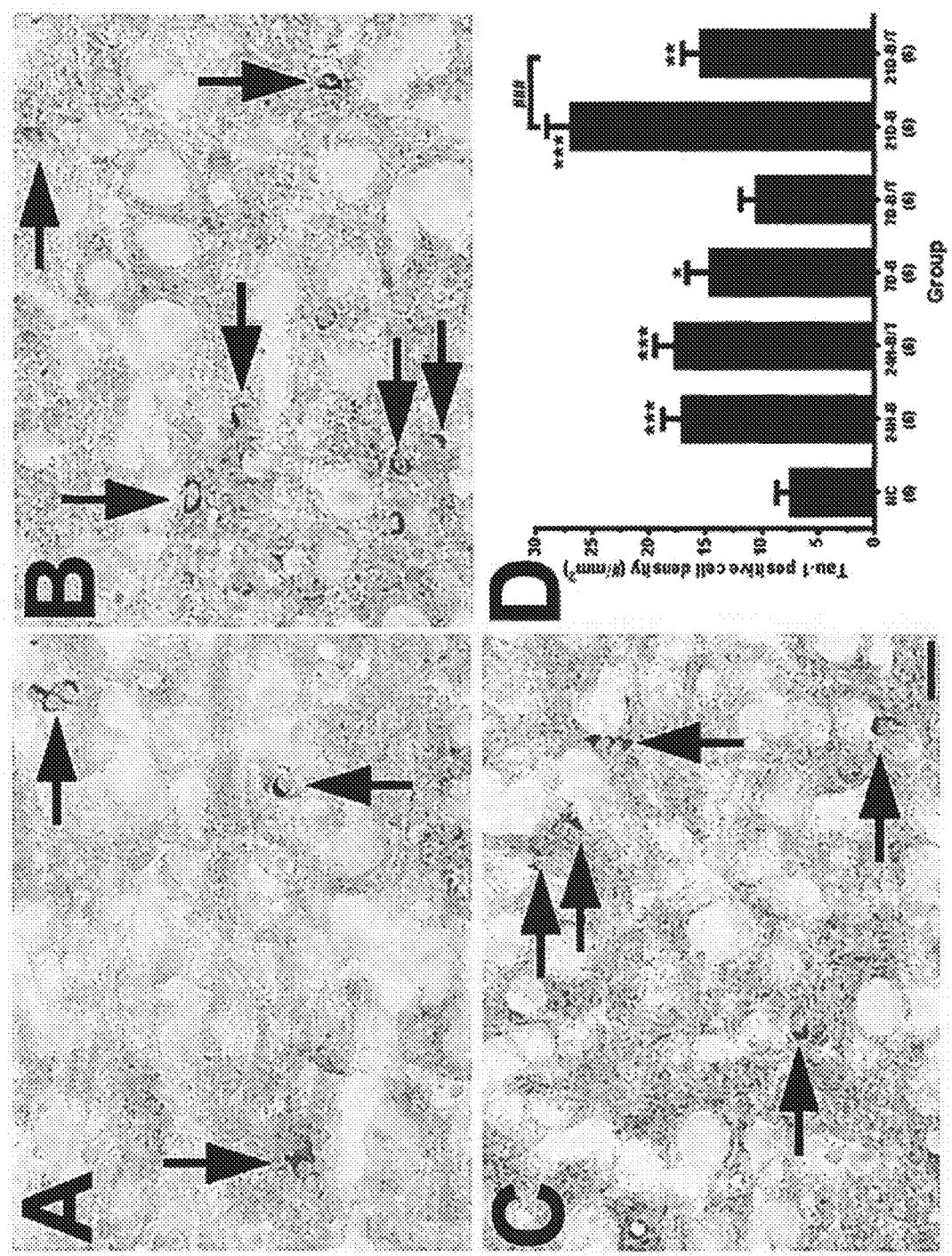
FIG. 17 shows that antioxidant treatment reduces the blast-induced somatic accumulation of Tau in the auditory cortex (AC). Images in A-C are examples of Tau-1 immunostaining in the deep layers of normal control rats (A); untreated, blast-exposed rats at seven days post-blast (B); and antioxidant-treated rats at twenty one days after injury (C). Tau-1 positive neurons were observed in the normal controls (arrows in A), untreated, blast-exposed animals (arrows in B) and in the antioxidant-treated, blast-exposed animals (arrows in C). The number of Tau-1 positive neurons in the AC was quantified, and the percentage of Tau-1 positive neurons in each cohort at each time point was calculated and statistically analyzed (D). An increased number of neurons with Tau-1-positive somata was observed in the AC at all time points post-injury in blast exposed animals (p<0.05, 0.001 or 0.001, *,  or *). Antioxidant treatment reduced this aberrant immunostaining pattern in blast-exposed rats at the seven- and 21-day sampling intervals, however statistical significance for positive treatment effect was only concluded among the 21-day cohorts (p<0.001, ###). Numbers in parentheses represent the total number of animals evaluated in each cohort at each time point. The scale bar in C=20 µm for A-C. Error bars represent SEM.

When rats were administered the combinatorial antioxidant (HPN-07/NAC) treatment regimen post-blast, the occurrence of somatic physiological Tau accumulation (i.e. somatic Tau-1 reactivity) was significantly reduced in neurons of the primary AC at both the seven and 21-day time points post-blast (FIG. 17, Table 1). The positive treatment effects were most prominent at the terminal 21-day time point, where the relative prevalence of somatic Tau-1-positive neurons was approximately two-fold less than that observed in untreated, blast-exposed rats, indicative of an unambiguous treatment-specific effect ($p<0.001$). However, in contrast to the observed effects on somatic Tau-1 accumulation, this treatment effect was not extended to the aberrant AT8 or T22 immunoreactivity patterns observed in the DCN and/or the AC, as antioxidant treatment appeared to have no discernible impact on the delayed, yet transient, increases in Tau hyperphosphorylation and oligomerization observed in these central auditory nuclei in blast-exposed animals (Tables 2 and 3). Therefore, the pathologic and treatment response patterns on neurotoxic Tau accumulation in neurons of the peripheral and central auditory pathways in blast-exposed rats are clearly distinct, perhaps reflective of their relative anatomical positions and contextual susceptibility to the propagative oxidative stress and neurodegeneration induced by blast.

Figure 18:
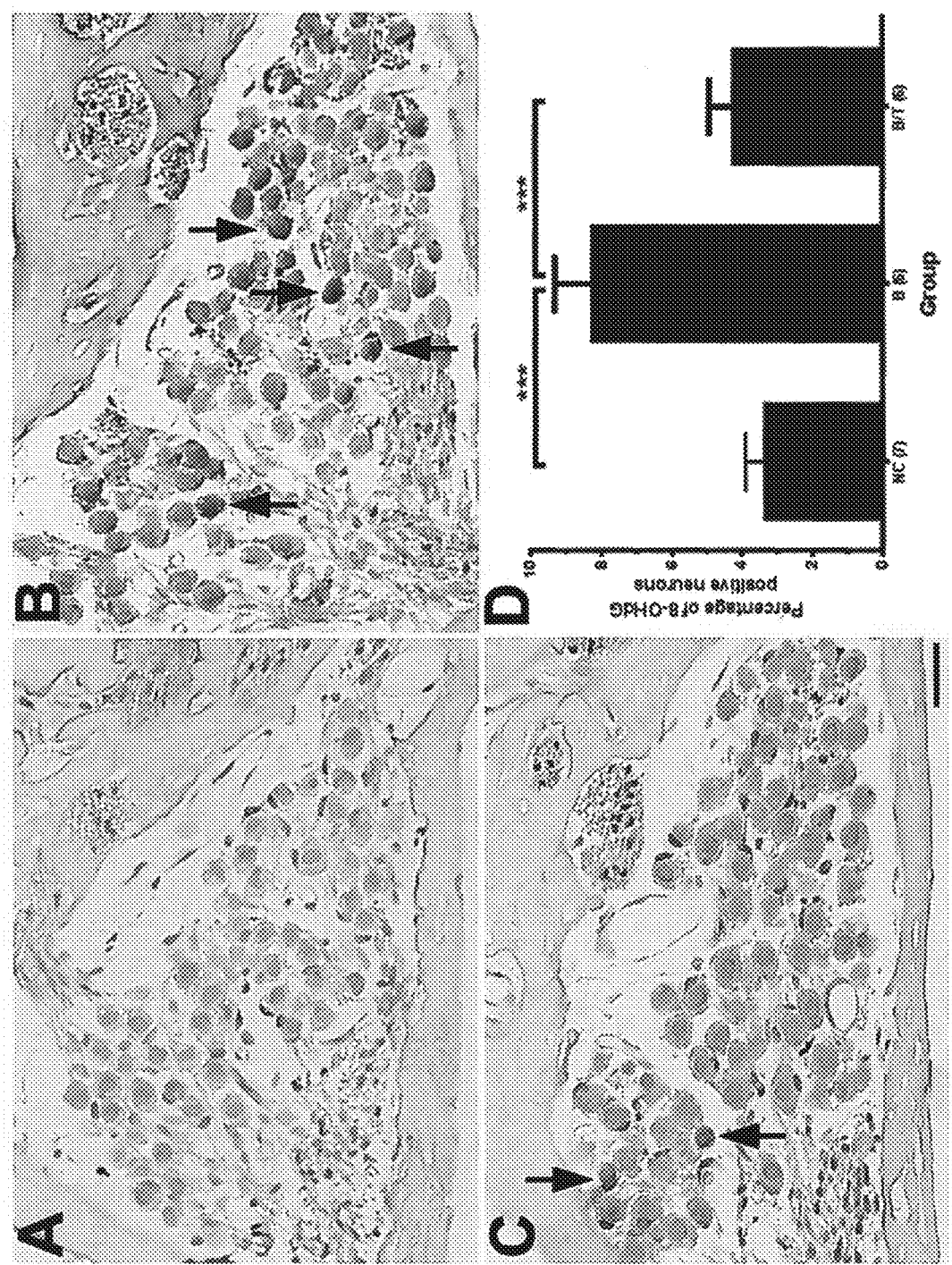
FIG. 18 shows that HPN-07/NAC treatment reduces blast-induced oxidative stress in the SG. Images are examples of 8-OHdG immunostaining in the SG in the basal turn of cochleae from naive (A); untreated, blast-exposed rats (B); and HPN-07/NAC-treated, blast-exposed rats (C) at 24 hours after blast exposure. The number of 8-OHdG-positive neurons in the SG was quantified and resultant percentiles of in each cohort were calculated and statistically analyzed (D). An increased number of 8-OHdG-positive neurons was observed in the SG of untreated, blast-exposed animals (p<0.001, *). HPN-07/NAC treatment significantly reduced this blast-induced stress response (p<0.01, *). Numbers in parentheses represent the total number of animals evaluated in each cohort. The scale bar in C=25 µm for A-C. Error bars represent SEM.

Antioxidants Reduce Oxidative Stress Among Neurons in the Spiral Ganglion of Blast-Exposed Rats To confirm that blast-induced oxidative stress did, in fact, contribute to the pathophysiological response associated with cochlear neurodegeneration, Applicants immunolabeled SGN tissues at 24 h post-blast with 8-OHdG, a biomarkera biomarker for oxidative DNA damage (Valavanidis et al., 2009). Intense 8-OHdG-positive staining was observed in the nuclei of SGNs of untreated, blast-exposed rats, indicative of damaging levels of oxidative stress in these neurons (FIG. 18B). As graphically summarized in FIG. 18D, a significantly greater number of 8-OHdG positive neurons was observed in the SG of these animals compared to naïve controls ($p<0.001$). In animals treated with the combinatorial antioxidant regimen, the prevalence of SGNs with intense 8-OHdG immunoreactivity was significantly reduced ($p<0.001$). These results provide direct evidence for oxidative stress as a contributing, if not predominant, factor in blast-induced neurodegeneration in the SG, and the positive therapeutic effects of antioxidant treatment on reducing the stress response.

Antioxidants Reduce Loss of Auditory Function in Blast-Exposed Rats

Figure 20:
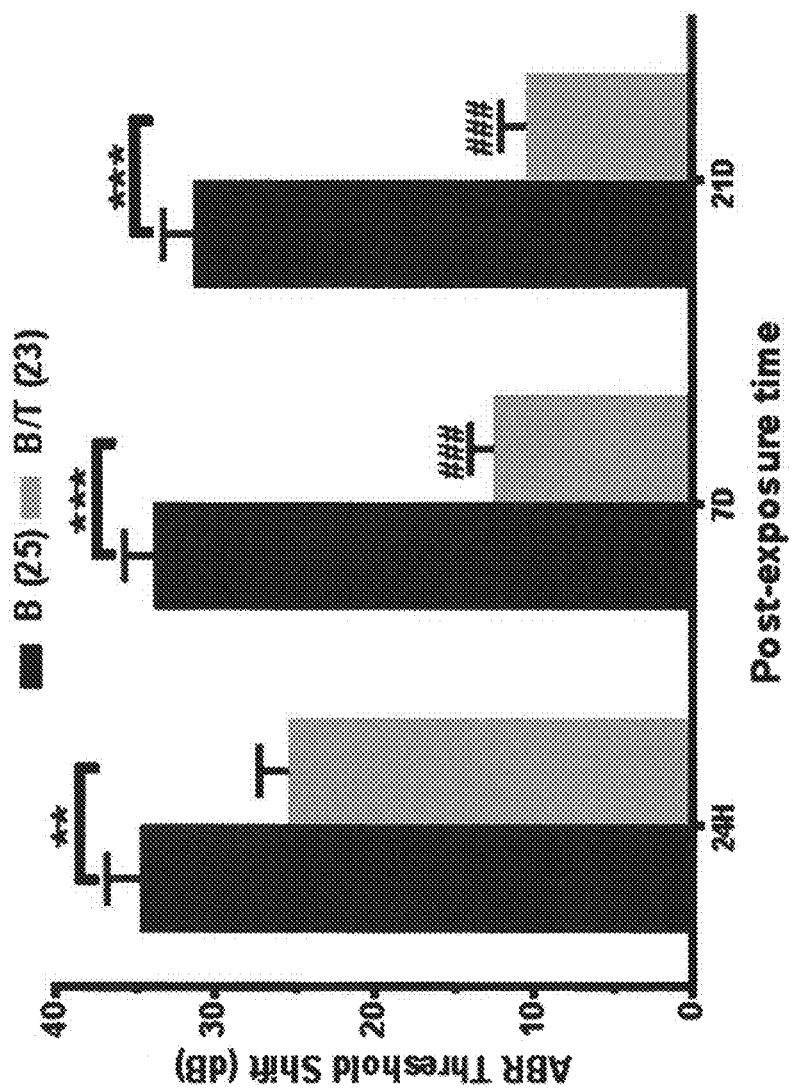
FIG. 20 shows that HPN-07/NAC treatment reduces blast-induced hearing loss. ABR threshold shifts averaged across 2-16 kHz comparing the treated and untreated animals at three time points after blast exposure. At each time point, the average ABR threshold shift of the HPN-07/NAC treated, blast-exposed animals (B/T) was significantly less than that of the untreated, blast-exposed controls (B). Numbers in parentheses represent the number of ears per group.

The ABR results from this study have been detailed in our previous report (Ewert et al., 2012) and are summarized in FIG. 20. In general, significant ABR threshold shifts were observed in untreated, blast-exposed animals at all time points after blast exposure. Compared to the untreated, blast-exposed group, ABR threshold shifts in the HPN-07/NAC treatment group were reduced by approximately 10 dB at 24 hours post-blast and 21 dB at 7- and 21-days post-blast (all $p<0.001$). Significant recovery in ABR threshold shifts in the antioxidant treated group was measured across all test frequencies (2-16 KHz) at both 7- and 21-days after blast exposure ($p<0.01$ or $0.001$). Consistent with the therapeutic efficacy observed for progressive SG neurodegeneration, these ABR results reflect the unambiguously positive attributes of HPN-07 and NAC for interrupting the ongoing pathophysiological response that results in progressive loss of auditory function in blast-exposed rats.

Further Analysis

While our blast model has been shown to induce significant and permanent ABR threshold shifts, indicative of diminished sensorineural function, only one to two percent IHC loss was observed in the middle and basal turns of untreated, blast-exposed rats at 21 days post-injury, which suggested a degree of under-appreciated neurodegeneration in these animals (Ewert et al. 2012; Du et al., 2013 and data not shown).

Indeed, beginning at seven days post-injury, we observed a significant decline in the number of neurites along the IHC innervation zone of the middle and basal turns of the OC in untreated, blast-exposed rats, and at the terminal, 21-day time-point of the study, an apparent loss of more than half of the original neurite population was measured in these regions (FIG. 19). These results correlated with significant blast-induced ribbon synapse loss among IHCs along the breadth of this region at the terminal 21-day time point post-trauma (FIGS. 8 and 9), indicative of markedly reduced peripheral auditory signaling to the brain. In these animals, the number of peripheral axons in the osseous SL was not significantly decreased until 21 days after blast (FIG. 10). These results are consistent with gradual, yet progressive, axonal retraction from lost IHC synapses in response to our blast exposure paradigm similar to what has been documented in mice exposed to an acute acoustic trauma (Jensen et al. 2015). Over this time period, pathologic NF-68 staining remained significantly elevated in SGN somata (FIG. 12), indicating sustained dysfunction. On the other hand, significant imbalances in normal NF-200 immunolabeling patterns of SGN somata was not observed until seven days after blast, with an apparent decline in the number of neurons bearing a type I-like immunoreactivity pattern first evident at 21 days post-injury (FIG. 11). These results seem to indicate that pathologic NF-68 accumulation is a more sensitive or epistatic pathologic marker for ongoing blast-induced neuropathy than loss of NF-200 immunoreactivity among SGNs.

The progressive pathophysiological response pattern observed in SGNs in response to our blast injury model is characteristic of neurodegeneration associated with mild blast-induced TBIs (mTBI) and other clinically-related neuropathies (Goldstein et al., 2012; Sajja et al., 2015; Walker and Tesco, 2013). The intensity of our blast overpressure (14 psi) model likely played a key role in the timing and extent of blast-induced neurodegeneration within the SG. In a related study in mice, Cho and colleagues demonstrated that, while no SG neuron loss was observed in animals exposed to either a 94 (13.63 psi) or 123 (17.84 psi) kPa blast, a 181 kPa (26.25 psi) blast induced significant SGN loss as early as seven days post-trauma (Cho et al., 2013). In the present study, the results of toluidine blue and NF-200 staining indicated that there was no significant neuron loss in the SG at the terminal experimental time point (21 days). Nonetheless, the sustained pathologic accumulation of both NF-68 and neurotoxic Tau variants in the SGN that we observed throughout the time course of our study is consistent with a degree of blast-induced neuropathy that may ultimately lead to a significant decline in this peripheral neuronal population. Consistent with this rationale, we observed statistically significant reductions in mean soma diameters among SGNs in untreated, blast-exposed rat cochleae at 21-days post-blast, indicative of ongoing neuronal atrophy in these animals (FIG. 13) (Raff et al., 2002). Moreover, the mTBI model employed herein is more likely to mimic that encountered by military personnel, thus providing potential insights into the progressive spatiotemporal neurodegeneration that is commonly observed among veterans (McKee and Robinson, 2014; Yankaskas, 2013).

mTBIs resulting from blast overpressure exposures are known to induce prolonged oxidative stress (Abdul-Muneer et al., 2013; Kochanek et al., 2013; Readnower et al., 2010). Therefore, we examined the therapeutic effects of post-traumatic intervention with an antioxidant formulation composed of the canonical antioxidant, N-acetylcysteine, and the free radical spin-trap agent, HPN-07, on the blast-induced pathophysiological response in the OC. We found that this therapeutic strategy significantly protected against direct manifestations of oxidative stress generated by the blast-physiological response to our blast-injury model (FIG. 18) and protected against both acute and chronic loss of NF-200-positive neurites in the IHC innervation zone and against nerve fiber loss in the SL in blast-exposed rats (FIG. 19 and FIG. 10). This therapeutic efficacy also translated to significant ribbon synapse preservation in the 16 kHz region of the OC and an indication of positive treatment effects in the 32 kHz region, as well (FIGS. 8 and 9). Moreover, HPN-07/NAC intervention also significantly reduced pathologic NF-68 accumulation and neuropathic imbalances in NF-200 immunostaining in the somata of SGNs and mitigated against blast-induced reductions in mean soma diameters among these neuronal populations (FIGS. 11-13). It is unclear whether these positive treatment effects were the result of direct effects of HPN-07 and NAC on reducing oxidative stress within neurons and neurites, an indirect protective effect through sustained HC viability, or a combination of both. However, as stated above, only 1-2% IHC loss was observed over the entire time course of our study (Ewert et al. 2012; Du et al., 2013). In light of the relatively early loss of IHC neurites in untreated, blast-exposed rats, the therapeutic effects observed in antioxidant-treated animals argues for direct protection of SGN neurites. Indeed, the more robust treatment effect observed for maintaining average peripheral axonal density along the breadth of the OC relative to preservation of ribbon synapse integrity may indicate that antioxidant intervention slows or arrests further axonal retraction, a therapeutic outcome that could enhance the efficacy of either inherent or therapeutic re-innervation strategies (Tong et al., 2013; Wan et al., 2014).

Aberrant phosphorylation and aggregation of the microtubule-associated protein, Tau, are both induced and potentiated by oxidative stress (Melov et al., 2007; Mondragón-Rodriguez et al., 2013). Moreover, in many instances, acute subjugation of Tau function can lead to chronic cytoskeletal destabilization that propagates in a transcellular fashion, as pathologic Tau oligomers from degenerating neurons conscript functional Tau into neurotoxic oligomers (Clavagura et al., 2013; Guo et al., 2011). Based on these observations and our previous studies on Tau in the CNS of blast-exposed rats (Du et al., 2016), we examined whether peripheral and central auditory pathways showed evidence of a tauopathic response that might contribute to sensorineural hearing loss.

Using our model of bTBI, we discovered that blast exposure induced acute Tau hyperphosphorylation in the somata of SG neurons in untreated rats that peaked at seven days post-trauma (Table 2 and FIG. 14). This pathologic response was mirrored by accumulation of oligomeric Tau inclusions that remained elevated throughout the experimental time course of our study (Table 3 and FIG. 15). Taken together, these results indicate that blast-induced Tau dysfunction is a coincident molecular sequela with neurofilament destabilization and neurodegeneration in the OC, indicative of a broad and sustained negative impact on cytoskeletal integrity among SG neurons.

Based on the fact that the pathologic response patterns for NF-68 and Tau staining in our blast model closely mirrored one another and the fact that neurofilament and Tau dysfunction are often inter-linked in neurodegenerative disorders, such as chronic traumatic encephalopathy, amyotrophic lateral sclerosis, and Alzheimer's disease, we examined whether these two pathologic markers co-existed within the somata of degenerating SGNs post-blast (Dekosky et al., 2013; Lin and Schlaepfer, 2006; Nguyen et al., 2001; Schmidt et al., 1990; Vickers et al., 1994). We discovered that NF-68 accumulation and Tau oligomerization were, indeed, co-localizable sequela in SGNs, yet based on their relative prevalence, Tau oligomerization may be an epistatic precursor to neurofilament destabilization in this pathologic context (FIG. 16).

Although oxidative stress is a governing factor for the induction and perpetuation of Tau hyperphosphorylation and oligomerization in the CNS, little is known regarding the precise physiological mechanisms that link these pathological responses (Alavi Naini and Soussi-Yanicostas, 2015). Nonetheless, our results demonstrated a clear therapeutic benefit for early intervention with HPN-07 and NAC on reducing these neurotoxic manifestations of Tau among SG neurons and their peripheral nerve fibers (FIGS. 14 and 15), consistent with the rationale that blast-induced oxidative stress may also drive this tauopathic response in the peripheral auditory system. It is particularly noteworthy that our combinatorial antioxidant formulation markedly reduced both acute and chronic oligomeric Tau accumulation in the SG following an acute blast exposure (FIG. 15). As Tau oligomers are widely believed to serve as the primary transmissible neurotoxic agents in many tauopathies, including Alzheimer's disease (Lasagna-Reeves et al., 2010 and 2012; Usenovic et al., 2015; Violet et al., 2015), the ability of early HPN-07 and NAC intervention to suppress their formation in SGNs may confer significant long-term protection against progressive neurodegeneration in the cochlea.

Like Tau, NF-68 is susceptible to oxidative stress-induced hyperphosphorylation and oligomerization, and there is evidence that aggregates of dysfunctional NF-68 can act as non-physiologic chaperones that promote Tau oligomerization (Ishihara et al., 2001). Previous in vitro studies demonstrated that both classical antioxidants (e.g. NAC) and HPN-07-related free radical spin-trap agents, such as alpha-phenyl N-tertiary-butyl nitrone (PBN), can protect native Tau and NF-68 from oxidative stress-induced aggregation (Kim et al., 2003 and 2004; Olivieri et al., 2001). The coincident ameliorative effects of HPN-07 and NAC on the somatic accumulation of NF-68 and neurotoxic Tau variants among the SGNs in our neuropathic blast study indicate that post-traumatic intervention with this therapeutic formulation holds the potential to also short-circuit these inter-related molecular stress response patterns in vivo.

Although blast exposure resulted in pathologic Tau immunostaining in both the peripheral and central auditory systems, we found that neurons in the SG and AC were more susceptible to this maladaptive response than those in the CN and IC (Valiyaveettil et al., 2012). However, antioxidant intervention was more effective in mitigating aberrant Tau modification in the peripheral auditory organ than in the central auditory system, where treatment effects were limited to the somatic accumulation of physiologic Tau, not hyperphosphorylated or oligomeric Tau accumulation (Tables 1-3 and FIG. 17). This discrepancy may reflect differences in the relative penetrance of HPN-07 and NAC across the blood brain barrier versus the blood cochlear barrier or differences in the manner in which the pathophysiological response originates in these tissues. It was demonstrated that the same combinatorial antioxidant regimen was sufficient for interrupting each of these tauopathic responses in hippocampal neurons, suggesting that, at least in this subcortical region of the brain, the drugs reached sufficient concentrations to mitigate blast-induced Tau dysfunction (Du et al., 2016). Thus, it possible that prolonged treatment or higher doses of these antioxidants are required to more effectively combat pathologic Tau accumulation in the central auditory system.

In summary, our results demonstrate that mTBIs caused by blast exposure induce progressive, retrograde neurodegeneration in the peripheral auditory system and that early intervention with HPN-07 and NAC provides significant protection against this outcome. Moreover, the ability of these antioxidants to prevent widespread Tau dysfunction and pathologic aggregation in SGNs in response to blast further underscores their long-term ameliorative benefits for limiting propagative neurotoxicity in the inner ear.

Example 3

It is discovered that noise-damaged animals treated with 2,4-disulfonyl α-phenyl tertiary butyl nitrone (HPN-07) exhibited significantly greater IHC neurite populations relative to untreated controls, and HPN-07 treatment uniquely induced a progressive degree of functional recovery in these animals, which is indicative of ongoing re-innervation. We therefore investigated whether HPN-07 is potent for inducing neuritogenesis and synaptogenesis.

HPN-07 was tested in three in vitro neuritogenic models (PC12 cells, and cochlear spiral ganglion explants, and co-cultures of SGN explants with hair cells (HCs) attached. Experimental data from theses analyses have demonstrated that (1) HPN-07 potentiates NGF-induced neuritogenesis in the PC12 cell line; (2) HPN-07 promoted neuritogenesis in spiral ganglion explants without hair cells; and (3) HPN-07 reversed excitotoxic ribbon synapse loss and increased neurite densities along the base of IHCs in SGN-HC co-cultures following excitoxic trauma induced by kainic acid (KA).

HPN-07 was extended to further characterize and optimize the pro-neuritogenic properties of HPN-07 in vitro and translate these findings into therapeutic outcomes in live animal experiments designed to test the efficacy of HPN-07 treatment for regenerating IHC-SGN synapses in vivo, using an acoustic overexposure paradigm that has been shown to induce minimal threshold shifts yet permanent de-afferentation of IHCs of the cochlea. Experimental results have shown that (1) HPN-07 potentiated both BDNF-induced and NT-3-induced neuritogenesis in SGN explants; (2) HPN-07 (formulated with NAC, HPN-07/NAC) prevented noise-induced hearing loss in rats; (3) HPN-07/NAC reversed noise-induced excitotoxic loss of IHC ribbon synapses in rats; and (4) HPN-07/NAC restored noise-induced ABR amplitude in rats.

We have confirmed HPN-07 potentiated both BDNF-induced and NT-3-induced neuritogenesis of Type I axons in spiral ganglion tissue explants in vitro in a dose-dependent manner. BDNF and NT-3 are inherent neurotrophic factors in the inner ear, which are essential for the development and survival of cochlear spiral ganglions (SGNs). As shown in FIGS. 24-27, exogenous BDNF and NT-3 induced significant neurite outgrowth at 10 µM (FIG. 24B and FIG. 26B) relative to untreated controls cultured in the same organotypic culture medium (NC, normal control, FIG. 24A and FIG. 26A). HPN-07 further increased the number and extent of nerve fibers in addition to BDNF or NT-3 (FIGS. 24C-D and FIG. 26C-D). Neurite length was not changed with any of the treatments compared to NC (FIG. 25 and FIG. 27).

An in vivo synaptogenesis experiment was designed as follows. Sprague Dawley rats weighing 250-300 g (Charles River) were divided into three groups: NC (no noise), Noise alone (treated with saline) and Noise+HPN-07/NAC (treated with HPN-07/NAC, 300 mg/kg). The rats were exposed to an octave-band noise (8-16 kHz) for 2 hours at 110 dB. Treatment started 24 hours after noise exposure, wherein 5 doses of treatment within 3 days were administered. Two weeks after treatment, cochlear samples were collected and analyzed (hair cell and synapse counting). Hearing was tested by ABR before noise, and retested 1 day and 15 days after noise.

Short-term hearing loss, as detected by a temporary threshold shift (TTS) measured 1 day after noise between untreated and treated was similar (FIG. 21A), which means noise caused similar damage in both groups. Ensuing HPN-07/NAC treatment prevented noise-induced permanent hearing loss (FIG. 21B) measured 15 days after noise exposure. TTS is the immediate hearing loss after exposure to noise which would recover over time. Not all TTS would disappear and the remaining final hearing loss is called permanent hearing loss. Hair cell loss after noise exposure was minimal and only appeared in the very basal region of the cochleae (FIG. 22). There were no significant differences among the three groups studied.

A one-time noise (8-16 kHz for 2 hours at 110 dB) caused 30%-40% loss of synapses at higher frequencies in Sprague Dawley rats. HPN-07/NAC treatment starting 24 hours post injury reversed the damage. Synapses are "connectors" that relay the sound information decoded by sensory hair cells to the brain (see red and green dots in FIG. 23). Loss of synapses has been suggested to cause difficulty in understanding speech in noisy environments, age-related hearing loss, tinnitus (ringing in the ear), etc.

As shown in FIG. 34, auditory brainstem response (ABR) wave I amplitudes and V/I amplitude ratios at 80 dB SPL 2 weeks after exposure were significantly decreased compared to pre-noise baseline in the non-treatment group. In comparison, ABR wave I amplitudes and V/I amplitude ratios did not change in the HPN-07/NAC treatment group. ABR wave V amplitudes did not change in either treated or untreated group. ABR test objectively measures auditory nerve reactions in response to sounds, which gives information about the inner ear (cochlea) and brain pathways for hearing. It is commonly used in both clinics and research. ABR wave I is thought to be generated at the peripheral or distal portion of auditory nerve. ABR wave V is thought to be generated in the lateral lemniscus and inferior colliculus of the brainstem. The wave I amplitude was decreased in the untreated group indicating reduced auditory input from the inner ear due to the loss of synapses, and hence wave V amplitude and V/I amplitude ratio were increased to compensate in the brainstem indicating increased neural activities in the central nervous system, which has been suggested to cause tinnitus (ringing in the ear). With HPN-07/NAC treatment, wave I amplitude was restored consistent with the recovery of synapse loss (see FIG. 34) and hence wave V was unchanged. Our results show HPN-7/NAC can restore hearing dysfunction caused by noise, and ABR wave amplitudes can be used to monitor synapse loss and treatment effects with medicine.

In summary, our results shows that HPN-07 represents a safe pharmacological means to regenerate lost ribbon synapses in the inner ear, providing a promising non-invasive alternative for treating cochlear synaptopathy and its associated prevalent clinical manifestations, such as difficulty understanding speech in noisy environments, presbycusis, hyperacusis and tinnitus.

Example 4—Established/Chronic Hearing Loss

A pilot study of established hearing loss was designed as shown in FIG. 28. Permanent threshold shift was established by open field blast insult. Treatment was initiated at 4 weeks post-injury, with HPN-07 plus NAC dosed at 300 mg/kg twice daily for 14 days. FIG. 28 further shows ABR threshold improvements 14 weeks post-injury (8 weeks post-treatment) versus pre-treatment.

As shown FIG. 29, NHPN-1010 treatment (HPN-07 plus NAC) restored IHC ribbon synapse numbers in established, chronic hearing loss model. NHPN-1010 treatment was initiated 4 weeks after injury and dosed daily for 14 days. Ribbon synapse counts were significantly restored 8 weeks post-injury.

As shown in FIG. 30, NHPN-1010 treatment resulted in recovery of ABR Wave I amplitudes in established chronic hearing loss model. The amplitudes in response to the 4 kHz and 8 kHz stimulus at both 80 and 70 dB SPL in the placebo group were reduced by blast exposure and continued to decrease as time progresses. Reduction in the amplitude responding to the 8 kHz stimulus at 80 dB SPL recovered completely to the pre-treatment level at 8 weeks post-NHPN-1010 treatment.

Further, as shown in FIG. 31, ribbon synapses were reduced after blast at 16, 32, 48 kHz and preserved/restored with NHPN-1010 treatment (HPN-07 plus NAC). In addition, as summarized in FIG. 32, NHPN-1010 treatment (HPN-07 plus NAC) can ameliorate blast effects on primary auditory afferent neurons-reduced retrograde neurodegeneration.

Example 5—Tinnitus Biomarkers

The blast (B) group received one shock tube blast (10 psi). The blast/treatment (B/T) group further received a total of 5 doses of HPN-07/NAC. Tissues were collected 8-9 weeks after blast exposure. Animals in each experimental group (6-8 rats/time point) were euthanized and intracardially perfused with saline followed by 4% paraformaldehyde in 0.1 M phosphate-buffered saline (PBS, pH 7.2). Cochleae, brains, and brainstems were removed and post-fixed in the same fixative (overnight for the cochleae and one week for the brain tissues). The fixed cochleae were washed with PBS and then decalcified for two weeks in 10% EDTA with solution changes two times each week. Cochleae were dehydrated, embedded in paraffin, and sectioned in a paramodiolar plane at a thickness of 6 and every 10th section was mounted on a slide (total of 10 slides per cochlea). The mounted sections were then processed for immunohistochemical analyses. The brain and brainstem from each animal was cryoprotected in 30% sucrose in PBS at 4° C. until the tissue settled to the bottom of the container, at which time they were embedded in Tissue-Tek (Sakura Finetek USA Inc. Torrance, Calif.) and serially sectioned in a coronal plane with a Thermo Cryotome (Thermo Fisher Scientific, Inc. Waltham, Mass.) at 18-20 µm. One section out of every ten from each brain and brainstem was mounted onto a gelatin pre-coated slide (total of 10 slides for each brainstem and 20 slides for each brain). These sections were then washed with PBS, blocked in 1% bovine serum albumin and either 1% normal horse serum or 1% normal goat serum in PBS, and permeabilized in 0.2% Triton X-100 in PBS (PBS/T). Blocked and permeabilized sections were then incubated with a primary antibody overnight at room temperature. After washing with PBS/T, a biotinylated secondary antibody (1:200, Vector Laboratories, Inc. Burlingame, Calif.) was applied to the slides for one hour at room temperature, and Vectastain ABC and DAB kits (Vector Laboratories, Inc. Burlingame, Calif.) were used for the immunolabeling visualization. Images were collected with a BX51 Olympus microscope for biomarker quantification. For fluorescent immunolabeling, the sections were incubated with appropriate Alexa Fluor® secondary antibodies (1:1000, Life Technologies, Co., Grand Island, N.Y.) for two hours at room temperature followed by DAPI labeling and mounting in anti-fade medium. Images were collected with a Zeiss LSM-710 confocal microscope.

Activity-regulated cytoskeleton-associated protein (ARC), also known as Arg3.1, is a plasticity protein. Decreased ARC in the central auditory system is associated with tinnitus. FIG. 35 shows ARC immunostaining in the central auditory system. The blast exposure down-regulated ARC in the AC, the IC, and the DCN. HPN-07/NAC treatment normalized ARC expression in the AC, the IC and the DCN, compared to the blast group without treatment.

Growth associated protein 43 (GAP-43) is a membrane associated phosphoprotein located in axonal growth cones. It is a marker for axonal outgrowth, synaptogenesis and synaptic remodeling. FIG. 36 shows GAP-43 immunostaining and western blot in the central auditory system. The blast exposure up-regulated GAP-43 in the AC, the IC and the DCN. HPN-07/NAC treatment normalized GAP-43 expression in the AC, the IC and the DCN, compared to the blast group without treatment.

GABAA Receptor is an ionotropic receptor and ligand-gated ion channel. Its endogenous ligand is γ-aminobutyric acid (GABA), the major inhibitory neurotransmitter in the central nervous system. FIG. 37 shows GABAA receptor α1 (GABAA Rα1) immunostaining in the DCN. FIG. 38 shows GABAA Rα1 (red) and GAD67 (green) co-labeling in the DCN. GAD67 is a biomarker for inhibitory neurons, indicating GABAA Rα1 positive cells are inhibitory neurons.

Glutamate receptor 2 (GluR2) is an ionotropic receptor of AMPA, which is a excitatory neurotransmitter in the central nervous system. Overstimulation of glutamate receptors causes neurodegeneration and neuronal damage through excitotoxicity. FIG. 39 shows GluR2 immunostaining in the DCN.

The blast exposure up-regulated the expression of both GABAA and glutamate receptors in the DCN, indicating re-organization of inhibition and excitation in the DCN. HPN-07/NAC treatment normalized the expression of GABAA and glutamate receptors in the DCN, compared to the blast group without treatment, restoring the balance between inhibition and excitation in the DCN.

Transient receptor potential cation channel subfamily V member 1 (TRPV1), also known as the capsaicin receptor and the vanilloid receptor 1, is activated by high temperature, acidic conditions, Capsaicin, and irritating compounds. Up-regulation of TRPV1 in the SG is associated with tinnitus. FIG. 40 shows TRPV1 immunostaining in the SG. The blast exposure up-regulated TRPV1 in the SG. HPN-07/NAC treatment normalized TRPV1 in the SG, compared to the blast group without treatment.

As used herein, the singular terms "a," "an," and "the" include plural referents unless the context clearly dictates otherwise. Thus, for example, reference to a compound can include multiple compounds unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scopes of this invention.

EQUIVALENTS

It is to be understood that while the disclosure has been described in conjunction with the above embodiments, the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement, and variation of the embodiments therein herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method for enhancing synaptogenesis and/or neuritogenesis in a subject suffering from cochlear synaptopathy or vestibular synaptopathy, comprising administering to said subject in need thereof an effective amount of 2,4-disulfonyl α-phenyl tertiary butyl nitrone (2,4-DSPBN) or a pharmaceutically acceptable salt thereof, wherein the administration of the 2,4-DSPBN or pharmaceutically acceptable salt thereof enhances regeneration of cochlear neurites or vestibular neurites in the subject.

2. The method of claim 1, wherein the 2,4-DSPBN or pharmaceutically acceptable salt thereof is administered as a pharmaceutical composition, which further comprises a pharmaceutically acceptable carrier.

3. The method of claim 1, wherein the 2,4-DSPBN or pharmaceutically acceptable salt thereof is administered to the subject orally, intravenously, subcutaneously, sublingually, subdermally, intrathecally, by inhalation, or locally within an ear.

4. The method of claim 1, which further comprises administering one or more compounds selected from the group consisting of N-acetylcysteine, Acetyl-L-Carnitine, glutathione monoethylester, ebselen, D-methionine, carbamathione and Szeto-Schiller peptides and their functional analogs.

5. The method of claim 1, which further comprises administering N-acetylcysteine.

6. The method of claim 1, wherein the subject suffers from a chronic auditory injury or chronic hearing loss.

7. The method of claim 6, wherein the chronic auditory injury or chronic hearing loss is caused by aging.

8. The method of claim 6, wherein the chronic auditory injury or chronic hearing loss is caused by exposure to blast or noise, either acute or chronic.

9. The method of claim 8, in which the 2,4-DSPBN or pharmaceutically acceptable salt thereof is administered to the subject at least one month after the exposure to blast or noise.

10. The method of claim 8, in which the 2,4-DSPBN or pharmaceutically acceptable salt thereof is administered to the subject at least one year after the exposure to blast or noise.

11. The method of claim 6, wherein the chronic auditory injury or chronic hearing loss is caused by infection.

12. The method of claim 11, in which the 2,4-DSPBN or pharmaceutically acceptable salt thereof is administered to the subject at least one month after the infection.

13. The method of claim 11, in which the 2,4-DSPBN or pharmaceutically acceptable salt thereof is administered to the subject at least one year after the infection.

14. The method of claim 6, wherein the chronic auditory injury or chronic hearing loss is caused by exposure to toxin.

15. The method of claim 14, in which the 2,4-DSPBN or pharmaceutically acceptable salt thereof is administered to the subject at least one month after the exposure to toxin.

16. The method of claim 14, in which the 2,4-DSPBN or pharmaceutically acceptable salt thereof is administered to the subject at least one year after the exposure to toxin.

17. The method of claim 1, wherein the subject also suffers from tinnitus.

18. The method of claim 1, wherein the subject also suffers from hyperacusis.

19. The method of claim 1, wherein the subject also suffers from presbycusis.

20. The method of claim 1, wherein the subject also suffers from balance disorder or Meniere's disease with synapse loss.

21. The method of claim 1, wherein number of viable nerve connections on inner hair cells in the subject is increased.

22. The method of claim 1, wherein number of synapses in tonotopic regions in organ of Corti in the subject is increased.

23. The method of claim 1, wherein the subject has not suffered a substantial loss of cochlear hair cells or vestibular hair cells.

24. The method of claim 1, wherein the subject has suffered a substantial loss of cochlear hair cells or vestibular hair cells.

25. The method of claim 1, wherein the 2,4-DSPBN or pharmaceutically acceptable salt thereof is administered to the subject at least one month after an auditory injury or hearing loss.

26. The method of claim 1, wherein the 2,4-DSPBN or pharmaceutically acceptable salt thereof is administered to the subject at least one year after an auditory injury or hearing loss.

* * * * *